(12) United States Patent
Maresca et al.

(10) Patent No.: US 8,728,820 B2
(45) Date of Patent: May 20, 2014

(54) METHOD OF NUCLEIC ACID RECOMBINATION

(75) Inventors: Marcello Maresca, Arlington, MA (US); Axel Steffen Erler, Haselbach (DE); Jun Fu, Dresden (DE); Philipp Martin Seibert, Dresden (DE); Adrian Francis Stewart, Dresden (DE); Youming Zhang, Saarbrucken (DE)

(73) Assignee: Gene Bridges GmbH (DE)

( * ) Notice: Subject to any disclaimer, the term of this patent is extended or adjusted under 35 U.S.C. 154(b) by 663 days.

(21) Appl. No.: 12/918,134

(22) PCT Filed: Feb. 20, 2009

(86) PCT No.: PCT/IB2009/000488
§ 371 (c)(1),
(2), (4) Date: Mar. 23, 2011

(87) PCT Pub. No.: WO2009/104094
PCT Pub. Date: Aug. 27, 2009

(65) Prior Publication Data
US 2011/0165630 A1    Jul. 7, 2011

(30) Foreign Application Priority Data
Feb. 20, 2008 (GB) .................................. 0803109.8

(51) Int. Cl.
*C12N 15/90* (2006.01)
*C12N 15/09* (2006.01)

(52) U.S. Cl.
USPC ............ 435/463; 435/455; 435/471; 435/490

(58) Field of Classification Search
None
See application file for complete search history.

(56) References Cited

U.S. PATENT DOCUMENTS

| 5,518,900 | A * | 5/1996 | Nikiforov et al. ............ 435/91.1 |
| 6,355,412 | B1 * | 3/2002 | Stewart et al. .................... 435/4 |
| 6,787,316 | B2 * | 9/2004 | Stewart et al. ................. 435/6.1 |
| 2003/0224521 | A1 * | 12/2003 | Court et al. .................... 435/455 |
| 2004/0029129 | A1 * | 2/2004 | Wang et al. ........................ 435/6 |

OTHER PUBLICATIONS

Zhang et al, DNA cloning by homologous recombination in *E.coli*, Dec. 2000, Nature Biotechnology, vol. 18: 1314-1317.*
Iyer et al. Classification and evolutionary history of the single-strand annealing protiens, RecT, Redbeta, ERF and RAD52. BMC Genomics, vol. 3, p. 8, Mar. 2002, printed as pp. 1/11 to 11/11.*
Khairnar et al. Involvement of periplasmic protein kinase in DNA strand break repair and homologous recombination in *Escherichia coli*. Molecular Microbiology, vol. 65, No. 2, pp. 294-304, Jul. 2007.*
Higuchi et al. Production of single-stranded DNA templates by exonuclease digestion following the polymerase chain reaction. Nucleic Acids Research, vol. 17, No. 14, p. 5865, 1989.*
Perkins et al. Sequence-dependent pausing of single lambda exonuclease molecules. Science, vol. 301, pp. 1914-1918, 2003, including supporting online material printed as pp. 1/18-18/18.*
Thomason et al. "Recombineering: Genetic Engineering in Bacterial Using Homologous Recombination" in Current Protocols in Molecular Biology, John Wiley & Sons, Inc. Supplement 78, pp. 1.16-1-1.16-24, Apr. 1, 2007.*
Zaccolo et al. The effect of high-frequency random mutagenesis on in vitro protein evolution: A study on TEM-1 beta-lactamase. Journal of Molecular Biology, vol. 285, pp. 775-783, 1999.*
Nakayma et al. Improvement of recombination efficiency by mutation of Red proteins. BioTechniques, vol. 38, No. 6, pp. 917-924, Jun. 2005.*
Fujioka et al. Targeted recombination with single-stranded DNA vectors in mammalian cells. Nucleic Acids Research, vol. 21, No. 3, pp. 407-412, 1993.*
Rauth et al. Transfection and homologous recombination involving single-stranded DNA substrateds in mammalian cells and nuclear extracts. Proceedings of the National Academy of Sciences, USA, vol. 83, pp. 5587-5591, Aug. 1986.*
Ellis et al., "High efficiency mutagenesis, repair, and engineering of chromosomal DNA using single-stranded oligonucleotides", PNAS, 2001, vol. 98, No. 12, 6742-6746.
Muyrers et al., "Techniques: Recombinogenic Engineering—New Options for Cloning and Manipulating DNA", Trends in Biochemical Sciences, vol. 26. No. 5, May 1, 2001. pp. 325-331.
Muyrers et al., "Rapid Modification of Bacterial Artificial Chromosomes by ET-Recombination", Nucleic Acid Research, Vol, 27, No. 6, Mar. 15, 1999, pp. 1555-1557.
Court et al., "Genetic Engineering Homologous Recombination", Annual Review of Genetics, vol. 36, Jan. 1, 2002, pp. 361-388.
Zhang et al., "Phase Annealing Proteins Promote Oligonucleotide-Directed Mutagenesis in *Escherichia coli* and Mouse ES Cells", BMC Molecular Biology, vol. 4, No. 1, Jan. 16, 2003.

(Continued)

*Primary Examiner* — Jennifer Dunston
(74) *Attorney, Agent, or Firm* — Kilpatrick Townsend & Stockton LLP

(57) ABSTRACT

The invention provides a method for inserting a single stranded replacement nucleic acid into a target nucleic acid, the method comprising the steps of: a) generating a single stranded replacement nucleic acid from a double stranded nucleic acid, wherein the double stranded nucleic acid is adapted at one or both of its 5' ends such that preferential degradation of one strand and/or strand separation generates the single stranded replacement nucleic acid, wherein the single stranded replacement nucleic acid comprises a 5' region that is identical to sequence on the target nucleic acid, a 3' region that is identical to sequence on the target nucleic acid and optionally a replacement region between the 5' and 3' regions that is not identical to sequence on the target nucleic acid, b) exposing the target nucleic acid to the single stranded replacement nucleic acid under conditions suitable for recombination to occur between the single stranded replacement nucleic acid and the target nucleic acid, and c) selecting a target nucleic acid whose sequence has been altered by inclusion of said single stranded replacement nucleic acid. Other methods for modifying target nucleic acids are also provided.

30 Claims, 25 Drawing Sheets

(56) References Cited

OTHER PUBLICATIONS

International Search Report and Written Opinion, PCT International Application No. PCT/IB2009/000488, mailed Oct. 30, 2009.
Datta et al., "Identification and analysis of recombineering functions from Gram-negative and Gram-positive bacteria and their phages", PNAS, 105(5), Feb. 5, 2008, pp. 1626-1631.

Maresca et al., "Single-stranded heteroduplex intermediates in λ Red homologous recombination", BMC Molecular Biology, 2010, 11:54, 15 pages.

* cited by examiner

Colonies on Cm plates from 50μl and on Km plates from 10ul (3 experiments)

|  | pBAD-neo*-erf | pBAD-neo*-recT | pBAD-neo*-redβ |
|---|---|---|---|
| Cm PCR product with denaturing | 5 | 21 | 560 |
| neo oligo to repair neo* | 520 | 570 | 540 |

Figure 5
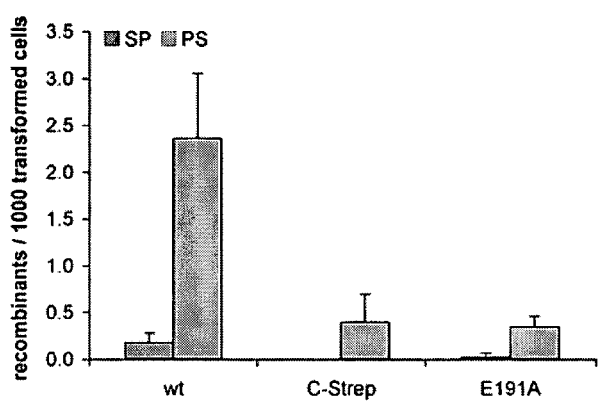
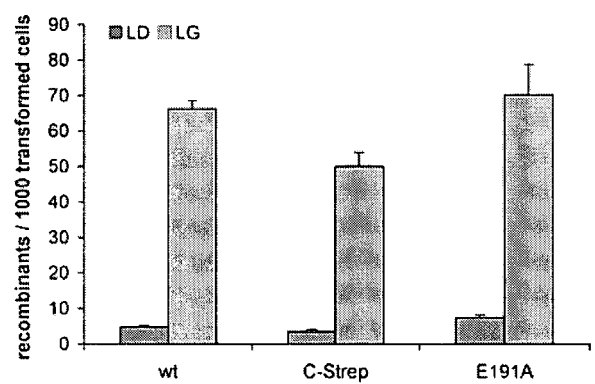

Figure 8B
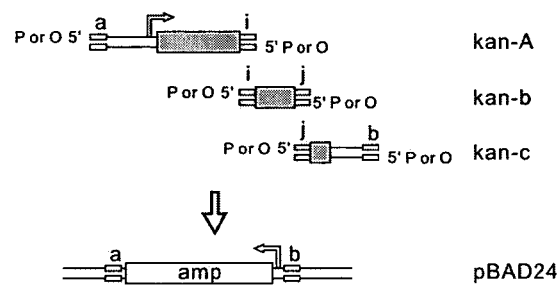
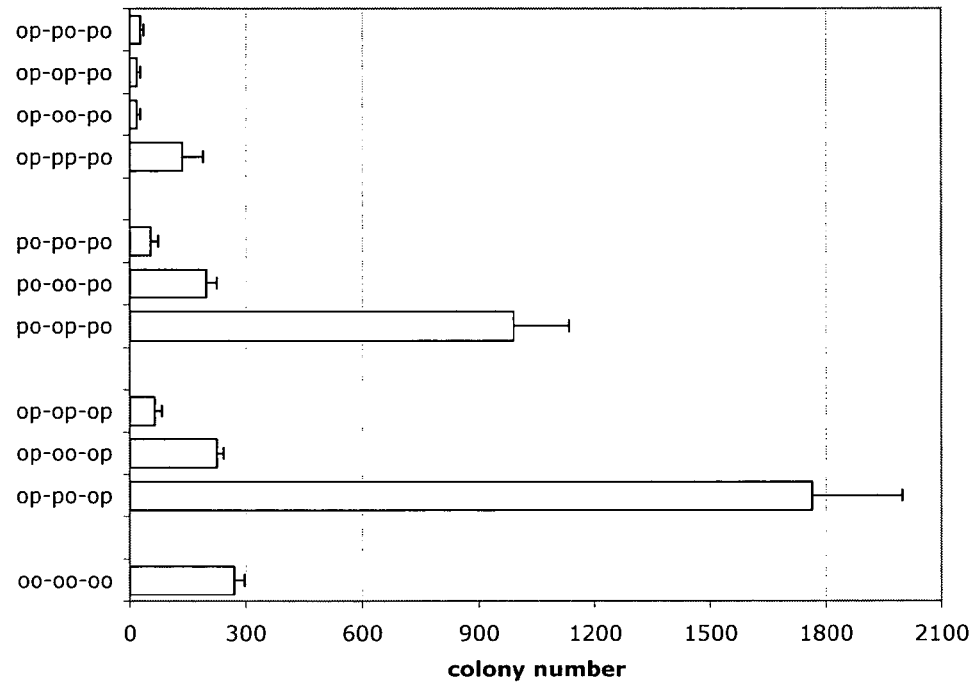

Figure 9

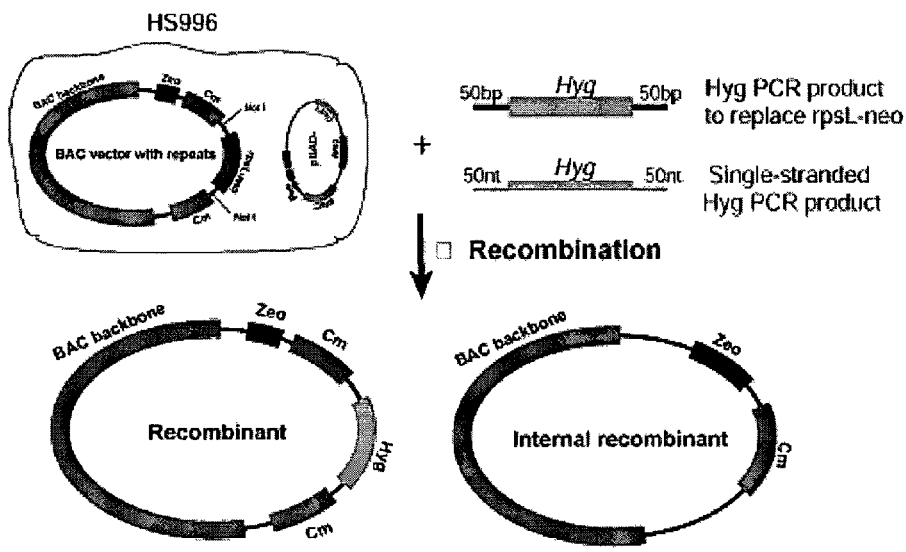

Colonies on 12.5µg/ml of Zeo, 15µg/ml of Cm and 50µg/ml of Str plates (2d culture)

|  | pBAD24 | pBAD-b | pBAD-a | pBAD-ba | pBAD-gba |
|---|---|---|---|---|---|
| PCR product | 119 | 161 | 107 | >3000 | >3000 |
| PCR product denatured | 105 | 172 | 113 | >3000 | >3000 |
| Un-induction | 115 | 146 | 106 | 237 | 225 |

Colonies on 12.5µg/ml of Zeo, 50µg/ml of Hyg and 50µg/ml of Str plates (20d culture)

|  | pBAD24 | pBAD-b | pBAD-a | pBAD-ba | pBAD-gba |
|---|---|---|---|---|---|
| PCR product | 0 | 5 | 0 | 47 | 689 |
| PCR product denatured | 0 | 140 | 0 | 112 | 485 |
| Un-induction | 0 | 1 | 0 | 2 | 7 |

Colonies on 10µg/ml of tetracyclin plates from 20d culture (10pg of pACYC184)

|  | pBAD24 | pBAD-b | pBAD-a | pBAD-ba | pBAD-gba |
|---|---|---|---|---|---|
| Induction | 210 | 128 | 204 | 149 | 82 |
| Un-induction | 246 | 246 | 250 | 237 | 210 |

SEQ ID NO:2

Red beta

MSTALATLAGKLAERVGMDSVDPQELITTLRQTAFKGDASDAQFIALLIVANQYGLNPWT
KEIYAFPDKQNGIVPVVGVDGWSRIINENQQFDGMDFEQDNESCTCRIYRKDRNHPICVT
EWMDECRREPFKTREGREITGPWQSHPKRMLRHKAMIQCARLAFGFAGIYDKDEAERIVE
NTAYTAERQPERDITPVNDETMQEINTLLIALDKTWDDDLLPLCSQIFRRDIRASSELTQ
AEAVKALGFLKQKAAEQKVAA

A 5' LR PCR screen

B 3' LR PCR screen

METHOD OF NUCLEIC ACID RECOMBINATION

CROSS REFERENCE TO RELATED APPLICATIONS

This application is the U.S. National Phase of PCT/IB2009/000488 filed on Feb. 20, 2009 which claims the benefit of British Application No. 0803109.8 filed on Feb. 20, 2008, both of which are incorporated herein by reference in their entireties.

The invention relates to a novel method for altering the sequence of a target genome by homologous recombination.

The engineering of genomes using homologous recombination is well established in several systems, for example in certain prokaryotes, yeasts, mouse embryonic stem cells and vertebrate cell lines in culture. Homologous recombination is the only way to specifically modify a native genome at a chosen target site. It is the most accurate and precise method available for genome engineering. However it can only be applied in a few, selected eukaryotic cellular systems and most eukaryotic genomes cannot be engineered using homologous recombination. Even in the amenable systems, the absolute frequency of homologous recombination is low and specialized methods to select the correct event are required (Glaser, S., Anastassiadis, K. and Stewart A. F. (2005) Current issues in mouse genome engineering, Nature Genetics, 37, 1187-93). Hence any improvement in the practice of homologous recombination has potential benefit for those systems which are currently amenable or intractable to engineering by homologous recombination.

A specific application of homologous recombination relates to its use for DNA engineering. In addition to the methodologies of restriction enzyme digestion, DNA ligation and PCR that comprise the major in vitro DNA engineering approaches, in recent times the use of homologous recombination in living *E. coli* cells has greatly expanded the repertoire of DNA engineering strategies (for review see Muyrers et al., Trends in Bioch Sci, (2001) May; 26(5):325-331). These approaches for DNA engineering by homologous recombination are collectively termed "recombinogenic engineering", or "recombineering" and have been practised in the common laboratory yeast, *Saccharomyces cerevisiae*, and the common cloning host, *Escherichia coli* (Muyrers, J. P. P., Zhang, Y. and Stewart A. F. 2001 Recombinogenic Engineering: new options for manipulating DNA Trends in Biochemical Sciences, 26, 325-31).

The engineering of genomes and DNA molecules is of fundamental importance to life science research. For example, gene targeting by homologous recombination in yeast has been crucial for many fundamental studies in eukaryotic cell biology; gene targeting in mouse ES cells is the cornerstone for the creation of mouse models of human disease (Glaser et al., 2005, supra); and the construction and precise manipulation of nucleic acid molecules is required in many studies and applications in the research fields of, for example, functional genomics (for review, see Vukmirovic and Tilghman, Nature 405 (2000), 820-822), structural genomics (for review, see Skolnick et al., Nature Biotech 18 (2000), 283-287) and proteomics (for review, see Banks et al., Lancet 356 (2000), 1749-1756; Pandey and Mann, Nature 405 (2000), 837-846).

Recombineering can be based on either the endogenous *E. coli* RecA pathway or on pathways mediated by phage proteins; for example, either Red alpha/Red beta from lambda phage or RecE/RecT from the rac prophage, preferably together with the Red gam protein. Gam inhibits the RecBCD nuclease, thereby protecting linear double stranded DNA ("dsDNA") from nuclease degradation by RecBCD. A 5' to 3' exonuclease activity (either RecBCD for the RecA pathway, Red alpha for the Red pathway or RecE for the RecE/T pathway) attacks a dsDNA end to resect the 5' ended strand, leaving a 3' ended, single stranded region (Carter, D. M. and Radding, C. M., 1971, J. Biol. Chem. 246, 2502-2512; Little, J. W. 1967, J. Biol. Chem., 242, 679-686), which becomes coated with an annealing protein (either RecA for the RecA pathway, Red beta for the Red pathway or RecT for the RecE/T pathway) (see Karakousis, G. et al., 1998, J. Mol. Biol. 276, 721-731; Li, Z. et al., 1998, J. Mol. Biol., 276, 733-744; Passy, S. I. et al. PNAS USA, 1999, 96: 4279-4284; Thresher, R. J. et al. J. Mol. Biol., 1995, 254: 364-371). In all cases, the evidence indicates that the loading of the annealing protein onto the growing single stranded DNA ("ssDNA") region is promoted by the partner exonuclease. The annealing protein/ssDNA complex initiates homologous recombination between two DNA regions in the annealing protein/ssDNA complex and their complementary regions on a second nucleic acid.

More recently, it was discovered that certain phage annealing proteins (Red beta and RecT) display activity to promote small recombination events independently of their exonuclease partners when provided with single stranded oligonucleotides. Furthermore, another annealing protein, Erf, from the P22 phage, was also shown to be able to mediate this activity, termed here "ssOR" (single stranded oligonucleotide repair). ssOR activity is described in a number of references including Muyrers, J. P. P. et al. (2001) "Phage annealing proteins mediate efficient oligonucleotide directed mutagenesis"; International patent publication No. WO 02/062988 (Gene Bridges GmbH); Swaminathan S. et al. (2001) "Rapid engineering of bacterial artificial chromosomes using oligonucleotides", Genesis, 29:14-21; Ellis H. M. et al., (2001) "High efficiency mutagenesis, repair, and engineering of chromosomal DNA using single-stranded oligonucleotides", Proc Natl Acad Sci USA, 98:6742-6; Court D. L. et al., (2002) "Genetic engineering using homologous recombination", Annu Rev Genet. 36:361-88; Zhang, Y. et al., (2003) "Phage annealing proteins promote oligonucleotide-directed mutagenesis in *E. coli* and mouse ES cells", BMC Mol Biol, 4 (1) 1; Yu, D. et al., (2003) "Recombineering with overlapping single-stranded DNA oligonucleotides: testing a recombination intermediate", Proc Natl Acad Sci USA, 100:7207-12; Costantino N. and Court D. L. (2003) "Enhanced levels of lambda Red-mediated recombinants in mismatch repair mutants", Proc Natl Acad Sci USA, 100:15748-53; Li X. T. et al., (2003) "Identification of factors influencing strand bias in oligonucleotide-mediated recombination in *Escherichia coli*", Nucleic Acids Res. 31:6674-87; Oppenheim A. B. et al., "In vivo recombineering of bacteriophage lambda by PCR fragments and single-strand oligonucleotides", Virology, 2004, February 20; 319(2):185-9; Huen, M. S. et al., (2006) "The involvement of replication in single stranded oligonucleotide-mediated gene repair", Nucleic Acids Res. 34:6183-94; U.S. Pat. No. 7,144,734 (NIH).

Detailed analysis of the ssOR activity led to a model based on annealing of the Red beta- or RecT-bound oligonucleotide complex to single stranded regions around the replication fork (Zhang, Y. et al., BMC Mol. Biol., 4(1), 1; Court, D. L. et al., (2002), Annu Rev. Genet., 36: 361-388). This model, termed "BARF" (Bias Annealing at the Replication Fork; Zhang, Y. et al., BMC Mol. Biol., 4(1), 1) involves the replacement of a target section of the lagging strand at a DNA replication fork with a short, central, section of the replacement single stranded oligonucleotide, which is directed to the lagging strand because the oligonucleotide can anneal to complementary sequence on the lagging strand template.

The BARF model explains two aspects of ssOR activity. First, it explains how recombination can occur without an accompanying exonuclease because the replication fork, not the exonuclease, is the agent that exposes the single stranded regions on the target to which the oligonucleotide anneals. Further, it is well known that larger regions of single strandedness are exposed during lagging strand synthesis than leading strand synthesis, thus providing a larger target area to which the oligonucleotide can anneal. Thus, it explains why ssOR shows strand preference on the target for annealing to the lagging strand template.

Hence recombineering exercises reported to date use either dsDNA or single stranded oligonucleotides as the initiating substrate. Currently explored applications of single stranded oligonucleotide technology have been limited either to partial gene construction or the introduction of small, site-directed mutations. In large part this is due both to the fact that single stranded (ss) oligonucleotides are easy to obtain but longer ssDNAs are not, and that engineering with ss oligonucleotides is efficient only to introduce very small mutations of less than 30 nucleotides in length. The introduction of new DNA sequence by homologous recombination with ssDNA longer than 30 nucleotides has been found to be extremely inefficient (illustrated in FIG. 4C). Beyond the use of single stranded oligonucleotides, both genome and DNA engineering using ssDNA recombination remain underexploited techniques. It is therefore the object of the invention to provide improved methods for engineering genomes and DNA more efficiently and with more strategic flexibility.

SUMMARY OF THE INVENTION

The invention provides a method for inserting a single stranded replacement nucleic acid into a target nucleic acid, said method comprising the steps of:
a) generating a single stranded replacement nucleic acid from a double stranded nucleic acid, wherein the double stranded nucleic acid is adapted at one or both of its 5' ends such that preferential degradation of one strand and/or strand separation generates the single stranded replacement nucleic acid, wherein the single stranded replacement nucleic acid comprises a 5' region that is identical to sequence on the target nucleic acid, a 3' region that is identical to sequence on the target nucleic acid and optionally a replacement region between the 5' and 3' regions that is not identical to sequence on the target nucleic acid,
b) exposing the target nucleic acid to the single stranded replacement nucleic acid under conditions suitable for recombination to occur between the single stranded replacement nucleic acid and the target nucleic acid, and
c) selecting a target nucleic acid whose sequence has been altered by inclusion of said single stranded replacement nucleic acid.

Also provided is a method for creating a mutation in a target nucleic acid, said method comprising the steps of:
a) exposing the target nucleic acid to a single stranded replacement nucleic acid in the presence of Red beta, or a functional equivalent thereof under conditions suitable for recombination to occur between said single stranded replacement nucleic acid and the target nucleic acid,
wherein the single stranded replacement nucleic acid comprises a 5' region that is identical to sequence on the target nucleic acid, a 3' region that is identical to sequence on the target nucleic acid and a replacement sequence between the 5' and 3' regions that is not identical to sequence on the target nucleic acid, wherein the replacement region is at least 61 bases in length, and
b) selecting a target nucleic acid whose sequence has been altered by inclusion of the single stranded replacement nucleic acid.

DETAILED DESCRIPTION OF THE INVENTION

In contrast to all expectation, a homologous recombination reaction that utilizes full length single stranded intermediates rather than symmetrically resected, partially single-stranded/partially dsDNA intermediates has been found. In naturally occurring endogenous systems, these full length single stranded intermediates are generated by the exonuclease activities of Red alpha or other endogenous 5'-3' exonucleases, or by endogenous helicases. Prior to the present invention, it had always been assumed that these enzymes work synchronously on both ends of a dsDNA molecule to produce recombination intermediates that are partially single stranded and partially double stranded.

Prior to the present invention, it was not known how Red alpha/beta or RecE/T mediate recombination with dsDNA. Whereas BARF explains recombination mediated by synthetic single stranded oligonucleotides to introduce short mutations, the mechanism involved in dsDNA-mediated genome and DNA engineering remained unresolved. For example, Court, D. L. et al (Annu Rev. Genet. 2002, 36, 361-388) proposed two complex models for dsDNA recombination and concluded that the mechanism employed by single stranded oligonucleotides cannot work for longer DNAs.

The mechanism elucidated by the present invention is mechanistically different from existing genome or DNA engineering approaches using dsDNA or single stranded oligonucleotides and is described herein as 'beta recombination'. The differences are shown schematically in FIG. 1. The existing model for the initiation of homologous recombination by dsDNA, and particularly by the Red proteins, is shown in FIG. 1A. In the first step, a 5'-3' exonuclease, such as Red alpha, symmetrically resects each end of a dsDNA to produce a reaction intermediate that is partly double stranded with terminal single stranded regions. The new mechanism elucidated by the present invention is shown in FIG. 1B, which illustrates that full length ssDNAs (also referred to herein as "single stranded replacement nucleic acid(s)") are produced from the dsDNA substrate either by the asymmetric action of an exonuclease to degrade one strand whilst leaving the other intact, or by a helicase to fully separate both strands.

The proposed reaction intermediate is illustrated in FIG. 1D in which a replication fork is shown proceeding from left to right. The two strands of the target DNA are shown as black and grey lines and the incoming single stranded recombination substrate DNA is a light grey line. In the middle of FIG. 1D are shapes depicting the two DNA polymerases connected by the rest of the holoenzyme and the helicase at the very centre (through which the lagging strand template is threaded). The leading strand is above with the polymerase proceeding continuously from left to right to synthesize the daughter black strand as complement of the parental grey strand. Below, the parental black strand is pulled through the helicase to extrude a single stranded region in which recombination occurs. In this single stranded region, Red beta (small dots in a chain) anneals the substrate DNA to the exposed single stranded DNA at places where the sequences are complementary. Even though there is a substantial interval of non-complementary DNA, a second region of complementarity secures the recombination intermediate. The 3' end of this intermediate serves as a primer for DNA polymerase to synthesize an Okazaki-like fragment, which will join up with the previous Okazaki fragment, here illustrated at the bottom left corner.

The mechanism of simple physical replication fork access (BARF) that has been proposed in the literature to explain the phenomenon of recombination effected by phage annealing proteins with ss oligonucleotides does not explain beta recombination in light of the following observations: First, RecT and Erf proteins can mediate efficient single stranded oligonucleotide directed mutagenesis (ssOR) but are very inefficient at beta recombination using long single stranded replacement nucleic acids (FIG. 3). Second, deletion of the mismatch repair pathway increases the efficiency of ssOR but not beta recombination (FIG. 4). Third, mutations of Red beta have been found that abolish beta recombination but not ssOR (FIGS. 5 and 6). Fourth, the inclusion of Red gamma has a very large beneficial effect on beta recombination but almost no effect on ssOR (FIG. 7). It is probable that, in addition to working by the BARF mechanism, Red beta is associated with a further property or properties that are required for beta recombination. Such properties may be, for example, a significantly greater co-operativity of polymerisation along a single stranded region of nucleic acid, or a unique ability to interact with a host factor.

This surprising observation has significant practical consequences for improved efficiencies of homologous recombination when engineering genomes and recombinant DNA as it makes it desirable to design methods for obtaining a greater yield of the full length single stranded intermediate, which will in turn promote higher efficiencies of homologous recombination. In practice, the simplest way to achieve this improvement is to modify the dsDNA substrate so that the intact ssDNA intermediate is generated during the homologous recombination reaction more efficiently. Former applications of genome or DNA engineering by homologous recombination have not incorporated this concept into the dsDNA substrate. Hence the invention is counterintuitive to current art for applied homologous recombination, which relies on a first step of 5'-3' exonuclease digestion, whereas here steps are taken to block these activities, either at one end or both. Thus, the surprising finding elucidated by the inventors leads to the development of improved methods for homologous recombination.

In particular, the invention provides a method for inserting a single stranded replacement nucleic acid into a target nucleic acid, said method comprising the steps of:
a. generating a single stranded replacement nucleic acid from a double stranded nucleic acid, wherein the double stranded nucleic acid is adapted at one or both of its 5' ends such that preferential degradation of one strand and/or strand separation generates the single stranded replacement nucleic acid, wherein the single stranded replacement nucleic acid comprises a 5' region that is identical to sequence on the target nucleic acid, a 3' region that is identical to sequence on the target nucleic acid and optionally a replacement region between the 5' and 3' regions that is not identical to sequence on the target nucleic acid,
b. exposing the target nucleic acid to the single stranded replacement nucleic acid under conditions suitable for recombination to occur between the single stranded replacement nucleic acid and the target nucleic acid, and
c. selecting a target nucleic acid whose sequence has been altered by inclusion of said single stranded replacement nucleic acid.

The surprising observation was made during studies with homologous recombination mediated by the Red system. Hence the invention is directly applicable to applications of the Red system to the engineering of genomes or recombinant DNA, termed 'recombineering'. Thus the steps of generating the single stranded replacement nucleic acid from the double stranded nucleic acid substrate and exposing the target nucleic acid to the single stranded replacement nucleic acid are preferably conducted in the presence of the phage annealing protein Red beta or a functional equivalent thereof. However the observation has relevance to the general use of homologous recombination to engineer genomes and thus can be applied to eukaryotic systems as well as prokaryotic systems. The skilled person will be able to determine which recombination enzymes should be used according to the particular host that the recombination is occurring in. For example, RecT or Erf or their functional equivalents may alternatively be used for ssOR. Likewise, the equivalent eukaryotic enzymes may be used. Examples of equivalent eukaryotic enzymes are the Herpes viral proteins, HSV-1 UL12, which is a 5'-3' exonuclease, and ICP8, which is a ssDNA binding protein, as well as related proteins such as those from Epstein-Barr virus (Mumtsidu E. et al. (2008), "Structural features of the single-stranded DNA-binding protein of Epstein-Barr virus", J Struct Biol. 161:172-87).

The generation of the single stranded replacement nucleic acid from the double stranded nucleic acid substrate prior to recombination may be mediated by any suitable means. In a preferred embodiment, the double stranded nucleic acid substrate is adapted such that one strand is preferentially degraded entirely to leave the other strand as the single stranded replacement nucleic acid. The degradation is preferably mediated by an exonuclease. The exonuclease may be a 3' to 5' exonuclease but is preferably a 5' to 3' exonuclease. Preferably, the 5' to 3' exonuclease is Red alpha (Kovall, R. and Matthews, B. W. Science, 1997, 277, 1824-1827; Carter, D. M. and Radding, C. M., 1971, J. Biol. Chem. 246, 2502-2512; Little, J. W. 1967, J. Biol. Chem., 242, 679-686) or a functional equivalent thereof. In an alternative embodiment, the exonuclease is RecBCD.

Alternatively and/or additionally, the single stranded replacement nucleic acid is generated from the double stranded nucleic acid substrate by a helicase. The helicase separates the dsDNA substrate into two single stranded nucleic acids, one of which is the single stranded replacement nucleic acid. The helicase may be either a 5'-3' or 3'-5' helicase. Preferably the helicase is RecBCD whilst it is inhibited by Red gamma. In other preferred embodiments, the helicase is any helicase of the RecQ, RecG or DnaB classes. In some embodiments, the single stranded replacement nucleic acid generated by the helicase is preferentially stabilised relative to the other single stranded nucleic acid generated by the helicase.

It has surprisingly been found that more recombinants are produced when the single stranded replacement nucleic acid is generated from a double stranded nucleic acid substrate, for example, by Red alpha digestion in the presence of Red beta, than when single stranded nucleic acid is used as the starting point, for example when boiled dsDNA is used and when Red alpha is not included and only Red beta is present. This is presumably due to the fact that during exonuclease resection of double stranded nucleic acid substrate, Red beta can processively bind onto the newly created single stranded regions as they emerge from the enzyme. Similarly, the binding of ssDNAs by Red beta is more efficient when any other exonuclease or helicase works in concert. Thereby Red beta binds the emerging ssDNA before it collapses on itself. Hence the binding of ssDNA by Red beta is more efficient when a 5'-3' exonuclease or helicase works in concert, than when Red beta has to bind ssDNA without the help of an enzyme that processively converts dsDNA into ssDNA. This difference in efficiency becomes increasingly more pronounced with increasingly longer DNA substrates.

Thus, the steps of generating the single stranded replacement nucleic acid from the double stranded nucleic acid substrate and exposing the target nucleic acid to the single stranded replacement nucleic acid are preferably conducted in the presence of the phage annealing protein (preferably Red beta or a functional equivalent thereof), and either its 5'-3' exonuclease partner (preferably Red alpha or a functional equivalent thereof) and/or a helicase (preferably RecBCD or a functional equivalent thereof).

The step of generating the single stranded replacement nucleic acid from the double stranded nucleic acid substrate may alternatively be conducted in the presence of Red beta or a functional equivalent thereof and Red gamma or a functional equivalent thereof in the absence of Red alpha or a functional equivalent thereof. Red gamma inhibits the major E. coli exonuclease RecBCD and so protects the double stranded nucleic acid substrate from degradation, which allows endogenous helicases to separate the two strands to generate the single stranded replacement nucleic acid. The inclusion of Red gamma has a very large beneficial effect on beta recombination, as shown in FIG. 7). The method is more efficient than when using Red beta alone with a single stranded replacement nucleic acid.

Even more preferably, the steps of generating the single stranded replacement nucleic acid from the double stranded nucleic acid substrate and exposing the target nucleic acid to the single stranded replacement nucleic acid are conducted in the presence of Red beta or a functional equivalent thereof, Red gamma or a functional equivalent thereof and Red alpha or a functional equivalent thereof.

In preferred embodiments, the step of generating the single stranded replacement nucleic acid from the double stranded nucleic acid substrate is carried out in a host cell in which the recombination occurs. Alternatively, the step of generating the single stranded replacement nucleic acid may be carried out in a separate host cell from the host cell in which the recombination occurs and may then be transferred to the host cell in which recombination occurs by any suitable means, for example, by transduction, transfection or electroporation. Alternatively, the step of generating the single stranded replacement nucleic acid from the double stranded nucleic acid substrate may be carried out in vitro. Thus, the requirement in the host cell in which recombination takes place for Red alpha or an alternative enzyme that preferentially degrades one strand of the double stranded nucleic acid substrate, or which separates the two strands, may be bypassed by providing the single stranded replacement nucleic acid to the host cell.

Advantageously, adapting one or both 5' ends of the double stranded nucleic acid increases the yield of the single stranded replacement nucleic acid. Preferably, this increase in yield is due to the effect of adapting the 5' end(s) on the enzymes that act to generate the single stranded replacement nucleic acid.

Preferably, the double stranded nucleic acid substrate is adapted so that it is asymmetric at its 5' ends. The asymmetry preferably causes one strand to be preferentially degraded. This preferably results in the other strand being maintained and so the production of a single stranded replacement nucleic acid is favoured, thereby improving the yield of the single stranded replacement nucleic acid.

By preparing a double stranded nucleic acid substrate with asymmetric 5' ends and bringing this into contact with a target nucleic acid in the presence of Red beta and a suitable degradation/separation enzyme (preferably Red alpha or a helicase), it is possible to increase engineering efficiencies to levels greater than any other configuration yet described for recombineering methodologies. Therefore, the method of the invention preferably utilises a double stranded nucleic acid substrate having asymmetry at its 5' ends wherein the method is conducted in the presence of Red alpha and/or a helicase and in the presence of Red beta. Red gamma is preferably also present as Red gamma inhibits RecBCD, which degrades double stranded DNA. Another efficient way to engineer DNA using Red-mediated homologous recombination employs a double stranded nucleic acid substrate that is adapted to have asymmetric 5' ends in the presence of Red beta and Red gamma, without Red alpha. A less efficient but still operable way to engineer DNA using Red-mediated homologous recombination employs a double stranded nucleic acid substrate that is adapted to have asymmetric 5' ends in the presence of Red beta, without Red gamma (or a functional equivalent thereof) and without Red alpha (or a functional equivalent thereof). Such a method is also encompassed within the scope of the invention.

Any suitable method of making a double stranded nucleic acid substrate asymmetric such that one strand is preferentially degraded whilst the other is maintained is envisaged by the present invention. The asymmetry may be conferred, for example, by one or more features present in only one strand of the double stranded nucleic acid substrate or by one or more features present in both strands of the double stranded nucleic acid substrate, wherein different features are present in different strands.

Preferably, the asymmetry is present at or in close proximity to the 5' ends of the two strands of the double stranded nucleic acid substrate, most preferably at the 5' ends. For example, the asymmetry is preferably present at the 5' end of the 5' identity regions of the double stranded nucleic acid substrate, or may be present in a region 5' of the 5' identity regions. The "identity regions" of the double stranded nucleic acid substrate correspond to the regions of the single stranded replacement nucleic acid that are identical to sequence on the target nucleic acid, or are complementary thereto. For example, the double stranded nucleic acid substrate may have one or more features at or in close proximity to the 5' end of one of its strands but not at or in close proximity to the 5' end of the other strand which make it asymmetric.

Preferably, the asymmetry is conferred by a modification to the nucleic acid sequence. Preferably, the modification affects the progression of exonuclease, preferably a 5'-3' exonuclease, preferably Red alpha exonuclease, on one strand but does not affect the progression of the exonuclease on the other strand. For example, the modification may inhibit the progression of exonuclease on one strand such that the exonuclease preferentially degrades the other strand. By "inhibit" the progression of exonuclease is meant that the modification inhibits the progression of the exonuclease on that strand relative to the other strand, for example, by at least 10%, at least 20%, at least 30%, at least 40%, at least 50%, at least 60%, at least 70%, at least 80%, at least 90%, at least 95%, most preferably 100%. For example, the modification may be the inclusion of a blocking DNA sequence, such as the Red alpha exonuclease pause sequence, more preferably, the Red alpha pentanucleotide pause sequence GGCGA, more preferably GGCGATTCT, more preferably, the left lambda cohesive end, also called the cos site (Perkins T T, Dalal R V, Mitsis P G, Block S M Sequence-dependent pausing of single lambda exonuclease molecules. Science 301:1914-8). The Red alpha exonuclease pause site may, for example, be placed at or in close proximity to the 5' end of one strand but not at or in close proximity to the 5' end of the other strand.

In a further preferred embodiment, the modification prevents the exonuclease from binding to one strand of the double stranded nucleic acid substrate such that only the other strand is degraded. In a further preferred embodiment, the modification does not prevent the exonuclease from binding but blocks it from degrading one strand or both of the double stranded nucleic acid substrate such that the strand that will anneal to the lagging strand template is stabilized upon separation from the dsDNA substrate by a helicase. In an alternative embodiment, the modification may promote the progression of exonuclease, preferably of 5'-3' exonuclease, more preferably Red alpha exonuclease, on one strand such that the exonuclease preferentially degrades that strand relative to the other strand. By "promote" the progression of exonuclease is meant that the modification promotes the progression of exonuclease activity on that strand relative to the other strand, for example, by at least 10%, at least 20%, at least 30%, at least 40%, at least 50%, at least 60%, at least 70%, at least 80%, at least 90%, at least 95%, at least 100%, at least 200%, at least 300%, or at least 400%. In embodiments in which the two strands of the double stranded nucleic acid substrate are separated by a helicase, the modification may serve to preferentially stabilise one strand, for example, by preventing an exonuclease or endonuclease from binding to that strand. In another embodiment, the modification prevents exonuclease degradation of both strands such that one strand is protected and can be released from the other by the action of a helicase.

In a preferred embodiment, the modification is one or more covalent modifications. Preferably, the covalent modification is present at or in close proximity to the 5' end of one strand but is not present at or in close proximity to the 5' end of the other strand. More preferably, the covalent modification is present at the 5' end of one strand but is not present at the 5' end of the other strand.

Preferred covalent modifications are the presence of a replacement nucleotide, such as the presence of a hydroxyl group or a phosphothioester bond. Such covalent modifications disfavour the action of exonucleases.

For example, in embodiments in which it is desired to protect the 5' end of the strand to be maintained, the covalent modification is preferably selected from one or more of the following:
 one or more phopshothioates in place of one or more phosphodiester bonds. Preferably, the phosphothioate(s) is present in place of the 5'-most bond in the 5' identity region, or are present in place of the first two bonds, or are present in place of up to each of the first six (e.g. 3, 4, 5, 6) or more bonds in the 5' identity region;
 one or more phosphoacetates in place of one or more phosphodiester bonds. Preferably, the phosphoacetate(s) is present in place of the 5'-most bond in the 5' identity region, or are present in place of the first two bonds, or are present in place of up to each of the first six (e.g. 3, 4, 5, 6) or more bonds in the 5' identity region;
 one or more locked nucleotides (preferably LNA; 2'-O and/or 4'-C-Methylen-beta-D-ribofuranosyl) in place of one or more nucleotides. Preferably, the one or more locked nucleotides are present in place of the first nucleotide in the 5' identity region, or are present in place of the first two nucleotides, or in place of up to the first six (e.g. 3, 4, 5 or 6) nucleotides;
 a hydroxyl group. Preferably, the 5' most nucleotide of the substrate is also the 5' most nucleotide of the region that is identical to sequence on the target nucleic acid and the hydroxyl group is at the 5' end of this region of sequence identity;
 a 5' protruding end. For example, the covalent modification may be 2 or more protruding nucleotides, 4 or more protruding nucleotides, 6 or more protruding nucleotides, preferably 11 or more protruding nucleotides, preferably a 5' end containing the Red alpha pause sequence, preferably the left lambda cohesive end known as cos;
 any other covalent adduct that renders resistance to 5'-3' exonucleases. For example, the 5' end may be modified to contain an attached adduct such as biotin deoxygenin or fluorophore such as FITC.

In embodiments in which it is desired to render one strand of the double stranded nucleic acid substrate sensitive to 5'-3' exonucleases such that the other strand is the strand to be maintained, the covalent modification is preferably selected from one or more of the following:
 a 5' phosphate group;
 a 5' end that is either flush or recessed with respect to the adjacent 3' end;
 a 5' end that carries a stretch of DNA sequence that is not identical to the target DNA. The stretch of DNA sequence may be, for example, 1-29 bps in length, more preferably 30-99 bps in length, more preferably 100-999 bps in length, even more preferably more than 1 kb in length;
 a 5' end that includes deoxy uridine nucleotides in place of deoxy thymidine nucleotides in the DNA strand;
 any other covalent adduct that conveys sensitivity to 5'-3' exonucleases.

Also encompassed within the scope of the invention are methods which use a double stranded nucleic acid substrate that contains one or more covalent modifications that protect the 5' end of the strand to be maintained and also one or more covalent modifications that render the other strand of the double stranded nucleic acid substrate sensitive to 5'-3' exonucleases. For example, the double stranded nucleic acid substrate may lack the 5' phosphate (i.e. presence of hydroxyl) on one strand whilst the other strand comprises the 5' phosphate.

Preferably, the double stranded nucleic acid substrate is adapted such that it comprises a 5' phosphothioate at one of its 5' ends but not at the other 5' end.

Any other chemical modification at or near the 5' end which inhibits or promotes exonuclease progression or blocks exonuclease binding is also encompassed within the scope of the invention.

As mentioned above, the asymmetry may be caused by the double stranded nucleic acid substrate having different extensions of single strandedness; that is different combinations of 5' protruding, blunt (or "flush") or 3' protruding ends. For example, the double stranded nucleic acid substrate may have only one 5' protruding end, only one 3' protruding end and/or only one blunt end. The asymmetry may be created by restriction cleavage to create different ends on the nucleic acid substrate. Restriction enzymes leave either 5' protruding, blunt or 3' protruding ends. The 5' protruding ends are least favoured for Red alpha digestion. Thus, in one embodiment, the double stranded nucleic acid substrate preferably has only one 5' protruding end. In embodiments in which the asymmetry is generated by different extensions of single strandedness, it is preferred that each strand of the double stranded nucleic acid substrate is a continuous nucleic acid strand.

The asymmetry may alternatively be caused by the double stranded nucleic acid substrate having different extensions of double strandedness. For example, one end may have no additional nucleic acid sequence beyond the end of the identity region, and the other may have additional non-identical sequences. The additional non-identical sequences may be as short as 4 base pairs, however, preferably will be longer than 10 base pairs, and more preferably longer than 100 base pairs.

As mentioned above, it has also been found that homologous recombination may also occur in the absence of the Reda exonuclease when a double stranded nucleic acid substrate is exposed to a target nucleic acid under conditions suitable for recombination to occur. It is hypothesised that a helicase acts to separate the two strands of the double stranded nucleic acid substrate and that the strand that is the single stranded replacement nucleic acid is then available for use in homologous recombination. Surprisingly, it has been found that adapting both of the 5' ends of the double stranded nucleic acid substrate leads to improved efficiencies of homologous recombination in such systems compared to systems in which the 5' ends are not adapted. Thus, in an alternative embodiment, the double stranded nucleic acid is symmetrically adapted at both of its 5' ends. In a preferred embodiment, the double stranded nucleic acid substrate is covalently modified at both of its 5' ends. Particularly preferred is the use of a double stranded nucleic acid substrate in which both 5' ends are covalently modified with a biotin molecule, or more preferably, with a phosphothioate. Preferably, in such embodiments, the recombination is carried out in the absence of Reda. Alternatively, the invention also envisages using a helicase to generate the single stranded replacement nucleic acid from a double stranded nucleic acid substrate that has 5' asymmetric ends, as described above.

The skilled person will understand the techniques required to adapt the double stranded nucleic acid substrate to make it asymmetric. For example, following cleavage by a restriction enzyme, the substrate may be dephosphorylated with alkaline phosphatase, and then cleaved with a second restriction enzyme. As restriction enzymes usually leave phosphates on the 5' end, this will generate an asymmetrically phosphorylated substrate.

Two oligonucleotides may be designed for use as the terminal identity regions as is usual for a recombineering exercise. These oligonucleotides may be chemically synthesized so that their 5' ends are different with respect to the presence of a replacement nucleotide at or in close proximity to the 5' end. These oligonucleotides can be used, for example, for oligonucleotide-directed mutagenesis after annealing, or PCR on templates to create the asymmetrically ended double stranded nucleic acid substrate or mixed with standard double stranded nucleic acid cassettes and co-introduced into a host for 'quadruple' recombination (see below).

The double stranded nucleic acid substrate may be made by any suitable method. For example, it may be generated by PCR techniques or may be made from two single stranded nucleic acids that anneal to each other. The double stranded nucleic acid substrate may in particular be generated by long range PCR. Long range PCR has been used in the art to generate double stranded fragments, for example of up to 50 kb (Cheng et al. (1994) Proc Natl Acad Sci 91: 5695-5699). The 5' ends of one or both of the primers used in this long range PCR may be adapted so that the PCR product is suitable for use as the double stranded nucleic acid substrate in the methods of the invention.

In some embodiments, the double stranded nucleic acid substrate is made from two or more double stranded nucleic acids or from one or more double stranded nucleic acids together with one or more single stranded oligonucleotides. The use of two double stranded nucleic acids to make the double stranded nucleic acid substrate is referred to herein as 'triple' recombination because there are two double stranded nucleic acid molecules which are used to make the double stranded nucleic acid substrate and there is one target nucleic acid. The use of three nucleic acids to make the double stranded nucleic acid substrate is referred to herein as 'quadruple' recombination because there are three nucleic acids which are used to make the double stranded nucleic acid substrate and there is one target nucleic acid. Any number of single stranded and/or double stranded nucleic acids may be used to make the double stranded nucleic acid substrate provided that the resulting double stranded nucleic acid substrate is adapted at one or both of its 5' ends such that preferential degradation of one strand and/or strand separation generates the single stranded replacement nucleic acid.

In all cases where more than one nucleic acid is used to make the double stranded nucleic acid substrate, a part of each of the more than one nucleic acids must be able to anneal with a part of its neighbouring nucleic acid. For example, for triple recombination, one end of each double stranded nucleic acid that is used to make up the double stranded nucleic acid substrate must be able to anneal to the target, whereas the other ends of each double stranded nucleic acid that is used to make up the double stranded nucleic acid substrate must be able to anneal to each other. The two double stranded nucleic acids that are used to make up the double stranded nucleic acid substrate are adapted such that one strand of each double stranded nucleic acid is preferentially maintained. Methods for adaptation that lead to preferential degradation are discussed above. Following degradation of one strand of each of the two double stranded nucleic acids, the remaining single strands anneal with each other to form the double stranded nucleic acid substrate of the invention. Triple recombination is discussed further in Example 8 and illustrated in FIG. 8A. Triple recombination is not normally very efficient but the use of asymmetric molecules to generate the double stranded nucleic acid substrate and also to generate the single stranded replacement nucleic acid advantageously increases efficiency.

A preferred embodiment for quadruple recombination involves the use of two single stranded oligonucleotides and one dsDNA (the 'double stranded cassette') as the three nucleic acids that are used to make the double stranded nucleic acid substrate. The two oligonucleotides are synthesized to both possess sequence identity with the target nucleic acid and with the double stranded cassette. For quadruple recombination, the double stranded cassette and the target nucleic acid preferably do not share any sequence identity of 20 or more continuous nucleotides. The two oligonucleotides used in this preferred embodiment of quadruple recombination may also have extra sequence in between their 5' and 3' identity regions to the cassette and the target. The two oligonucleotides are preferably adapted such that they both can anneal to the same strand on the cassette. One oligonucleotide contains a region of identity to the target at its 5' end and a region of identity at its 3' end to the cassette, whereas the other oligonucleotide contains a region of identity to the target at its 3' end and a region of identity at its 5' end to the cassette. Thereby the oligonucleotides provide the 5' and 3' identity regions to the same single stranded molecule. The cassette is advantageously rendered to have asymmetric ends so that the strand that is preferentially degraded has the same sequence as the synthesized oligonucleotides. In a further embodiment, the 5' oligonucleotide which will be present in the single stranded replacement nucleic acid that is generated from the double stranded nucleic acid substrate, preferably has a 5' phosphothioate bond. The asymmetry may alternatively or additionally be conferred by the use of an asymmetrically modified double stranded cassette. It is possible to obtain the double stranded cassette from a standard plasmid by restriction digest without needing to do PCR, which greatly speeds up the procedure relative to conventional methods. Quadruple recombination is discussed further in Example 8 and illustrated in FIG. 8B.

The single stranded replacement nucleic acid that is generated from the double stranded nucleic acid substrate comprises a 5' region that is identical to sequence on the target nucleic acid (the "5' identity region"), a 3' region that is identical to sequence on the target nucleic acid (the "3' identity region") and optionally a replacement region between the 5' and 3' identity regions that is not identical to sequence on the target nucleic acid. The skilled person will understand how to design the double stranded nucleic acid substrate such that the required single stranded replacement nucleic acid is generated. Preferably, the single stranded replacement nucleic acid corresponds to the full length of one of the strands in the double stranded nucleic acid substrate. However, the single stranded replacement nucleic acid may have lost some sequence from the 5' and/or 3' end of the strand that was present in the double stranded nucleic acid substrate, provided that it retains the 5' identity region, the 3' identity region and in embodiments in which the replacement region is required, the replacement region.

Preferably, the target nucleic acid is the lagging strand template of a DNA replication fork and the single stranded replacement nucleic acid has 5' and 3' identity regions that can anneal to the lagging strand template of the target DNA when it is replicating. The term "lagging strand", as used herein, refers to the strand that is formed during discontinuous synthesis of a dsDNA molecule during DNA replication. The single stranded replacement nucleic acid anneals through its 5' and 3' identity regions to the lagging strand template of the target nucleic acid and promotes Okazaki-like synthesis and is thereby incorporated into the lagging strand. The direction of replication for plasmids, BACs and chromosomes is known, and so it is possible to design the double stranded nucleic acid substrate so that the maintained strand is the one that will anneal to the lagging strand template.

A variation of the triple recombination described above is referred to herein as 'double' recombination. This embodiment of the invention involves two rounds of insertion of a single stranded replacement nucleic acid into the target nucleic acid. In one embodiment of double recombination, the single stranded replacement nucleic acid in steps a)-c) is a first single stranded replacement nucleic acid as defined in step a), specifically comprising a replacement region between the 5' and 3' regions, and the method comprises additional steps d)-f):

d) generating a second single stranded replacement nucleic acid from a second double stranded nucleic acid, wherein the second double stranded nucleic acid is adapted at one or both of its 5' ends such that preferential degradation of one strand and/or strand separation generates the second single stranded replacement nucleic acid, wherein the second single stranded replacement nucleic acid comprises:
  i) either a 5' region that is identical to a first sequence on the replacement region of the first single stranded replacement nucleic acid and a 3' region that is identical to a second sequence on the replacement region of the first single stranded replacement nucleic acid, or a 5' region that is complementary to a first sequence on the replacement region of the first single stranded replacement nucleic acid and a 3' region that is complementary to a second sequence on the replacement region of the first single stranded replacement nucleic acid; and
  ii) optionally a replacement region between the 5' and 3' regions that is not identical to sequence on the target nucleic acid,
e) exposing the selected target nucleic acid of step c) to the second single stranded replacement nucleic acid under conditions suitable for recombination to occur between the second single stranded replacement nucleic acid and the selected target nucleic, and
f) selecting a target nucleic acid whose sequence has been altered by inclusion of said second single stranded replacement nucleic acid.

The efficiency of this double recombination embodiment may be improved if the first single stranded replacement nucleic acid or the second single stranded replacement nucleic acid, preferably both, can anneal to the lagging strand of the target nucleic acid when it is replicating. The lagging strand can be identified from the direction of replication. This direction may be determined from the relative positions of the origin of replication and the recombination site in the target nucleic acid. The first and second single stranded replacement nucleic acids will anneal to the same strand if the second single stranded replacement nucleic acid comprises a 5' region that is identical (a 5' identity region) to the first sequence on the replacement region of the first single stranded replacement nucleic acid and a 3' region that is identical (a 3' identity region) to the second sequence on the replacement region of the first single stranded replacement nucleic acid.

Double recombination provides a method for inserting a first and a second single stranded replacement nucleic acid into the target nucleic acid. Unlike triple recombination, insertion of the first single stranded replacement nucleic acid is not dependent on the insertion of the second single stranded replacement nucleic acid.

However, insertion of the second single stranded replacement nucleic acid is dependent on insertion of the first single stranded replacement nucleic acid. The replacement region of the second single stranded replacement nucleic acid is inserted between the first and second sequences on the replacement region of the first single stranded replacement nucleic acid. The first single stranded replacement nucleic acid may therefore be considered as an "adaptor" that is inserted by steps a)-c) providing appropriate sequence for insertion of the second single stranded replacement nucleic acid. In other words, it is possible to use the first and second sequences in the replacement region of the first single stranded replacement nucleic acid for the insertion of the second single stranded replacement nucleic acid. In this way, following selection of the target nucleic acid in step c), it is possible to produce multiple nucleic acids comprising different insertions by carrying out steps d)-f) in parallel with different second single stranded replacement nucleic acids. Any second single stranded replacement nucleic can be inserted provided that it has the appropriate 5' and 3' regions identical or complementary to the first and second sequences on the replacement region of the first single stranded replacement nucleic acid. For example, these 5' and 3' regions may be included in the second replacement nucleic acid by producing the second double stranded nucleic acid substrate by PCR using stock PCR primers designed to contain the 5' and 3' regions in the primers, or by ligation of small dsDNA fragments with the sequence of the 5' and 3' regions onto dsDNA sequences which do not already comprise these regions.

Double recombination allows the replacement or excision of sequence between the first and second sequences on the replacement region of the first single stranded replacement nucleic acid. This is useful, for example, if there is a counter selectable marker between the first and second sequences. It is then possible to select for the loss of this marker in step f), thereby producing sequences which do not have a marker remaining in the target nucleic acid.

In a preferred embodiment of double recombination, the replacement region of the first single stranded replacement nucleic acid and/or the replacement region of the second single stranded replacement nucleic acid comprise a selectable marker. For example, this selectable marker may be an antibiotic resistance marker, such as blasticidin, ampicillin, kanamycin or other markers known in the art.

Preferably, in double recombination the 5' region of the first single stranded replacement nucleic acid is longer than 20 nucleotides, more preferably between 40 and 60 nucleotides. Similarly, it is preferred for the 3' region of the first single stranded replacement nucleic acid to be longer than 20 nucleotides, more preferably between 40 and 60 nucleotides. In the same way it is preferred for the 5' region of the second single stranded replacement nucleic acid to be longer than 20 nucleotides, more preferably between 40 and 60 nucleotides; and for the 3' region of the second single stranded replacement nucleic acid to be longer than 20 nucleotides, more preferably between 40 and 60 nucleotides.

Typically, in double recombination the target nucleic acid will be comprised within a genome or an episome, e.g. a BAC or plasmid.

The first and second double stranded nucleic acids used in double recombination may be obtained from any source. In preferred embodiments, the first double stranded nucleic acid is a PCR fragment, a synthetic oligomer or a fragment obtained by gene synthesis. The second double stranded nucleic acid may similarly be a PCR fragment, a synthetic oligomer or a fragment obtained by gene synthesis. In other embodiments, the second double stranded nucleic acid is a fragment obtained by digestion of a vector.

The skilled person will appreciate that preferred features described infra of the integers in steps a)-c) of the methods of the invention may be applied independently to the analogous integers in steps d)-f) of this embodiment.

Methods for designing replacement nucleic acids having at least two regions of sequence identity are well known in the art. By "identity" is meant that when the sequences of the replacement and target nucleic acid molecules are aligned, there are a number of nucleotide residues that are identical between the sequences at equivalent positions. Degrees of identity can be readily calculated (Computational Molecular Biology, Les, A. M., et al. ed., Oxford University Press, New York, 1988; Biocomputing, Informatics and Genome Projects, Smith, D. W., ed., Academic Press, New York, 1993; Computer Analysis of Sequence Data, Part 1, Griffin, A. M., and Griffin, H. G., eds. Humana Press, New Jersey 1994; Sequence Analysis in Molecular Biology, von Heinje, G., Academic Press, 1987; and Sequence Analysis Primer, Gribskov, M. and Devereux, J. eds., M Stockton Press, New York, 1991). Such regions of identity are preferably at least 4 nucleotides in length, for example, between 4 and 8 nucleotides in length, preferably at least 15 nucleotides in length, more preferably at least 20 nucleotides in length, more preferably at least 25 nucleotides in length, even more preferably at least 30 nucleotides in length, even more preferably at least 40 nucleotides in length. Particularly efficient recombination events may be effected using longer regions of identity, such as 50 nucleotides or more, 75 nucleotides or more, 100 nucleotides or more, 125 nucleotides or more, 150 nucleotides or more, 200 nucleotides or more, 300 nucleotides or more or 400 nucleotides or more. The 5' identity region may be the same length as the 3' identity region. Advantageously, the 3' identity region may be longer than the 5' identity region. The efficiency of recombination has surprisingly been found to correlate with an increased length of the 3' identity region. Thus, in a preferred embodiment, the 3' identity region is at least 30 nucleotides in length whilst the 5' identity region is at least 20 nucleotides in length, wherein the 3' identity region is 10 or more nucleotides longer than the 5' identity region. The 5' identity region may alternatively be longer than the 3' identity region.

Preferably, the degree of identity over the 5' and 3' identity regions is at least 95%, 98% or 99% or more identity, preferably 100% identity, as determined using BLAST version 2.1.3 using the default parameters specified by the NCBI (the National Center for Biotechnology Information) [Blosum 62 matrix; gap open penalty=11 and gap extension penalty=1]. The 5' and 3' identity regions may be interrupted by non-identical sequence regions, provided that sufficient sequence identity is retained to allow the beta recombination reaction to occur.

Similarly, methods for designing replacement nucleic acids having at least two regions of complementary sequence are well known in the art. In some embodiments, a second single stranded replacement nucleic acid comprises a 5' region that is complementary (a "5' complementarity region") to a first sequence on the replacement region of the first single stranded replacement nucleic acid and a 3' region that is complementary (a "3' complementarity region") to a second sequence on the replacement region of the first single stranded replacement nucleic acid and. By "complementary" within this context it is not meant that the sequences must be 100% complementary, although 100% complementarity may be preferred. By "complementary" it is meant that when a sequence that is 100% complementary to the 5' region is aligned with the first sequence (or similarly when a sequence that is 100% complementary to the 3' region is aligned with the second sequence), there are a number of nucleotide residues that are identical between the sequences at equivalent positions. As discussed above, degrees of identity can be readily calculated. Preferably, the degree of identity is at least 95%, 98% or 99% or more identity, preferably 100% identity, as determined using the BLAST methodology described above. Accordingly, the 5' and 3' regions may be interrupted by non-complementary sequence regions, provided that sufficient sequence complementarity is retained to allow the beta recombination reaction to occur. The complementary regions are preferably at least 4 nucleotides in length, for example, between 4 and 8 nucleotides in length, preferably at least 15 nucleotides in length, more preferably at least 20 nucleotides in length, more preferably at least 25 nucleotides in length, even more preferably at least 30 nucleotides in length, even more preferably at least 40 nucleotides in length. Particularly efficient recombination events may be effected using longer regions of complementarity, such as 50 nucleotides or more, 75 nucleotides or more, 100 nucleotides or more, 125 nucleotides or more, 150 nucleotides or more, 200 nucleotides or more, 300 nucleotides or more or 400 nucleotides or more.

The 5' and 3' identity regions may be located on the single stranded replacement nucleic acid molecule so that the 5' identity region is at the very 5' end of the molecule and the 3' identity region is at the very 3' end. Thus, the 5' and/or 3' identity regions preferably extend to the 5' and/or 3' ends respectively of the single stranded replacement nucleic acid. It is particularly advantageous for the 5' identity region to extend to the end of the single stranded replacement nucleic acid as this results in an increased efficiency of recombination compared to when the 5' identity region does not extend to the end of the single stranded replacement nucleic acid. However, one or both of the 5' and 3' identity regions may also be located internally. For example, there may be additional sequence 5' of the 5' identity region and/or 3' of the 3' identity region. Where such additional sequence is present, it is preferably between 1 nucleotide and several kilobases in length, for example, between 1 nucleotide and 3 kilobases in length. The 5' and 3' identity regions should thus be tailored to the requirements of each particular experiment.

In the same way, in embodiments that involve 5' and 3' complementarity regions, the 5' and 3' complementarity regions may be located on the single stranded replacement nucleic acid molecule so that the 5' complementarity region is at the very 5' end of the molecule and the 3' complementarity region is at the very 3' end. Thus, the 5' and/or 3' complementarity regions preferably extend to the 5' and/or 3' ends respectively of the single stranded replacement nucleic acid. Alternatively, one or both of the 5' and 3' complementarity regions may also be located internally. For example, there may be additional sequence 5' of the 5' complementarity region and/or 3' of the 3' complementarity region. Where such additional sequence is present, it is preferably between 1 nucleotide and several kilobases in length, for example, between 1 nucleotide and 3 kilobases in length. The 5' and 3' complementarity regions should thus be tailored to the requirements of each particular experiment.

There are no particular limitations relating to the location of the corresponding 5' and 3' identity regions on the target DNA molecule, except that for circular double-stranded DNA molecules, the beta recombination event should not abolish the capacity to replicate.

By including in the single stranded replacement nucleic acid 5' and 3' identity regions that span regions of non-identical sequence compared to the target nucleic acid molecule, one or more mutations along the length of the replacement sequence can be achieved. Similarly, in embodiments that involve 5' and 3' complementarity regions, the single stranded replacement nucleic acid may include 5' and 3' complementarity regions that span regions of non-identical sequence compared to the target nucleic acid molecule so that one or more mutations along the length of the replacement sequence can be achieved. The mutation may be any mutation, for example one or more substitutions (such as a point mutation), deletions or insertion mutations, but is preferably one or more insertion mutations. Combinations of these mutations may also be made. Thus, multiple mutations may be introduced into the target nucleic acid molecule in a single step.

In embodiments in which the replacement region between the 5' and 3' identity regions is not present and the 5' identity region is immediately adjacent to the 3' identity region, the single stranded replacement nucleic acid may be used to effect a deletion mutation. Similarly, in embodiments that involve 5' and 3' complementarity regions, if a replacement region between the 5' and 3' complementarity regions is not present and the 5' complementarity region is immediately adjacent to the 3' complementarity region, the single stranded replacement nucleic acid may be used to effect a deletion mutation. In embodiments in which the replacement region between the 5' and 3' regions is present, the sequence of the replacement region is preferably less than 50% homologous to the target sequence, e.g. less than 45%, less than 40%, less than 35%, less than 30%, less than 25%, less than 15%, less than 10%, or less than 5% homologous to the target sequence or shares no homology with the target sequence. In this way, large regions of the target nucleic acid may be manipulated in a single step. For example, the sequence coding for a protein domain may be deleted by replacement with a "stop" codon followed by non-coding sequence or substituted for sequence coding for an alternative domain of interest or alternatively "knocked out" by deletion of the entire region. Alternatively, a gene of interest may be "knocked out" by replacing the target nucleic acid with non coding sequence. Substitutions may result, for example, in point mutations and insertions and/or deletions may be made to create an altered reading frame. Preferably, the single stranded replacement nucleic acid is used to insert sequences into the target nucleic acid.

The length of the replacement region can be as short as one nucleotide, preferably at least 20 nucleotides in length. However the method is especially useful for lengths longer than 30 nucleotides, which are those lengths difficult to achieve using oligonucleotide-directed mutagenesis (see also FIG. 4C). Especially preferred are sequences of 40 or more nucleotides in length, or more than 60 nucleotides in length, or 150 or more nucleotides in length or 300 or more nucleotides in length (preferably much longer regions, for example, at least 500, at least 1000, at least 2000, at least 3000 or at least 5000 nucleotides in length). This is described in more detail below.

All current recombineering methodology for the use of ssDNA as the replacement nucleic acid is based on oligonucleotides. The prior art does not describe how to use ssDNA longer than very short chemically synthesized ssDNA molecules (termed "oligonucleotides"). Previous reports in the scientific literature of the use of phage annealing proteins to effect recombination with ssDNA were limited to the use of short oligonucleotides, which were usually shorter than 100 nucleotides (see Constantino, N. and Court, D. (2003) Proc Natl Acad Sci USA 100: 15748-15753; Li, X, T. et al. (2003) Nucleic Acids Res. 31:6674-6687). For example, single strand oligonucleotide directed mutagenesis (ssOR) has been used to direct the introduction of small mutations from one nucleotide up to tens of nucleotides, but this becomes very inefficient above thirty nucleotides, as shown in FIG. 4C. Longer synthetic oligonucleotides have been used (up to 180 nucleotides), but the reduction of oligonucleotide quality with increasing length makes this an undesirable option. These oligonucleotides have always been almost completely complementary to the target DNA with which they recombine. In all cases, the oligonucleotides have contained only a small, centrally located difference in DNA sequence to the target. This difference, which is introduced into the target DNA molecule by recombination, has always been less than one third of the oligonucleotide and has usually been less than 10%. Thus, only small insertions have been reported in E. coli in addition to point mutations and deletions. Operationally this means that existing methods for ssDNA recombination mediated by Red beta are limited to the introduction of less than 60 nts of change into the target molecule. Although more than one oligonucleotide could be used in a concerted process to get around this problem, such oligonucleotides must share at least 20 nucleotides of perfect complementarity and the physical limitations of co-transforming several oligonucleotides together effectively limits this option to 4 oligonucleotides at most (4×100 with 20 oligonucleotides overlap is equal to 340 nucleotides). However, this is a very optimistic appraisal and effectively the use of multiple oligonucleotides leads to a length of less than 260 nucleotides. Accordingly, within these limitations of length and complementarity, it is not possible to introduce new genes and current applications are limited to either partial gene construction or the introduction of small, site directed mutations.

Existing methods of ssDNA recombination do not permit the introduction of genetically selectable genes, such as antibiotic resistance genes, because they are too long. Consequently engineering with single stranded oligonucleotides relies on a physical method for the identification of recombination, such as PCR and cannot employ the experimentally simpler methods of genetic selection to identify the correct recombinants. A consequence of these current limitations is that DNA engineering using ssDNA recombination remains an obscure, specialist interest.

It has now surprisingly been found that Red beta alone, without its partner Red alpha, can efficiently recombine ssDNA longer than synthetic oligonucleotides. This second discovery follows from the first one discussed above that Red homologous recombination proceeds via a full length single stranded intermediate which is generated by Red alpha. The present invention advantageously enables the use of Red beta to mediate ssDNA recombination beyond conventional size limits which provides a new dimension of DNA engineering based on ssDNA. Furthermore it has been found that this ssDNA activity of Red beta is greatly promoted by the presence of Red gamma even without the presence of Red alpha. This phenomenon has a number of advantages over methodologies disclosed previously. In particular, beta recombination may be used for inserting substantial lengths of nucleic acid sequence into a target molecule.

In view of this surprising finding, a method is provided herein for creating a mutation in a target nucleic acid, said method comprising the steps of:
a) exposing the target nucleic acid to a single stranded replacement nucleic acid in the presence of Red beta and Red gamma, or a functional equivalent thereof under conditions suitable for recombination to occur between said single stranded replacement nucleic acid and the target nucleic acid,
   wherein the single stranded replacement nucleic acid comprises a 5' region that is identical to sequence on the target nucleic acid, a 3' region that is identical to sequence on the target nucleic acid and a replacement region between the 5' and 3' regions that is not identical to sequence on the target nucleic acid, wherein the replacement region is at least 61 bases in length, and
b) selecting a target nucleic acid whose sequence has been altered by inclusion of the single stranded replacement nucleic acid.

Furthermore, a method is provided herein for creating a mutation in a target nucleic acid, said method comprising the steps of:
a) exposing the target nucleic acid to a single stranded replacement nucleic acid in the presence of Red beta, or a functional equivalent thereof under conditions suitable for recombination to occur between said single stranded replacement nucleic acid and the target nucleic acid,
   wherein the single stranded replacement nucleic acid comprises a 5' region that is identical to sequence on the target nucleic acid, a 3' region that is identical to sequence on the target nucleic acid and a replacement region between the 5' and 3' regions that is not identical to sequence on the target nucleic acid, wherein the replacement region is at least 61 bases in length, and
b) selecting a target nucleic acid whose sequence has been altered by inclusion of the single stranded replacement nucleic acid.

Thus, the replacement region in the single stranded replacement nucleic acid for use in the invention is preferably at least 61 nucleotides in length, at least 110 nucleotides, at least 150 nucleotides in length, at least 200 nucleotides, at least 300 nucleotides, at least 500 nucleotides, at least 800 nucleotides, at least 1100 nucleotides, at least 1500 nucleotides, at least 2,000 nucleotides, at least 5,000 nucleotides or longer. This extends the application of single-stranded recombination to the insertion of entire genes, for example, in the construction of plasmids, for applications such as ES cell targeting; or for the construction of Bacterial Artificial Chromosomes (BACs) used, for example, in transgenesis, or endogenous prokaryotic and eukaryotic chromosome(s). Preferably, the replacement region is all or part of a gene. More preferably, it is a whole gene. Where the replacement region is all or part of a gene, the replacement region may optionally include one or more of the functional sequences that are required for expression of the gene. The gene may act as a selectable marker such as an antibiotic resistance gene. This liberates the researcher from the current requirement, in the vast majority of current ssDNA engineering applications, to use physical screening methods like colony PCR hybridization, and allows the experimentally simpler methods of genetic selection to identify correct recombinants. Further applications of the methods of the invention will be clear to the skilled person.

Thus, the inventors' finding results in a greater diversity of homologous recombination procedures because it ensures that there is no restriction to the type of mutation to which the present invention may be applied, although the most evident applications include those which are extremely difficult or time consuming using approaches that are currently available. Examples include the cloning, insertion or deletion of an entire gene of interest in any species, such as yeast chromosomes, mouse embryonic stem cell chromosomes, *C. elegans* chromosomes, *Arabidopsis* and *Drosophila* chromosomes, human cell lines, viruses and parasites, or exogenous molecules such as plasmids, YACs and HACs.

Any method to make the single stranded replacement nucleic acid will be suitable. The single stranded replacement nucleic acid may be generated in vitro or in vivo. Preferably, the single stranded replacement nucleic acid is generated from a double stranded nucleic acid substrate as described above. Most preferably, it is generated from a double stranded nucleic acid substrate that is adapted at one or both of its 5' ends such that preferential degradation of one strand and/or strand separation generates the single stranded replacement nucleic acid, as described above. Alternatively, the single stranded replacement nucleic acid may be produced using single strand phages such as M13. These phages amplify and package only one strand from a dsDNA template. Boiling dsDNA (for example, before electroporation) could be used to make the ssDNA but once the boiled DNA is single stranded, it may collapse on itself and become difficult for binding by Red beta. With short ssDNAs like oligonucleotides, this is much less of a problem than with longer ssDNAs. Using standard recombineering methodology, DNAs longer than a few hundred nucleotides do not appear to work, at least in part, because of this problem. This is why Court et al. (Annu Rev Genet, 2002, 36: 361-388) reported the failure of Red beta to mediate recombination with longer ssDNAs and consequently invoked complex explanations for recombination intermediates using DNAs longer than oligonucleotides.

Double recombination, as discussed above, may also be carried out using these methods of the invention. This embodiment involves creating two rounds of mutation in the target nucleic acid. In one embodiment of this double recombination, the single stranded replacement nucleic acid in steps a) and b) is a first single stranded replacement nucleic acid as defined in step a), and the method comprises additional steps c) and d):

- c) exposing the selected target nucleic acid of step b) to a second single stranded replacement nucleic acid in the presence of Red beta, or a functional equivalent thereof under conditions suitable for recombination to occur between said second single stranded replacement nucleic acid and the selected target nucleic acid, wherein the second single stranded replacement nucleic acid comprises:
  - i) either a 5' region that is identical to a first sequence on the replacement region of the first single stranded nucleic acid and a 3' region that is identical to a second sequence on the replacement region of the first single stranded nucleic acid, or a 5' region that is complementary to a first sequence on the replacement region of the first single stranded replacement nucleic acid and a 3' region that is complementary to a second sequence on the replacement region of the first single stranded replacement nucleic acid; and
  - ii) a replacement region between the 5' and 3' regions that is not identical to sequence on the target nucleic acid, wherein the replacement region is at least 61 bases in length,
- d) selecting a target nucleic acid whose sequence has been altered by inclusion of the second single stranded replacement nucleic.

As in the other embodiment of double recombination discussed above, the efficiency of this method may be improved if the first single stranded replacement nucleic acid or the second single stranded replacement nucleic acid, preferably both, can anneal to the lagging strand of the target nucleic acid when it is replicating. The lagging strand can be identified from the direction of replication as discussed above. The first and second single stranded replacement nucleic acids will anneal to the same strand if the second single stranded replacement nucleic acid comprises a 5' region that is identical (a 5' identity region) to the first sequence on the replacement region of the first single stranded replacement nucleic acid and a 3' region that is identical (a 3' identity region) to the second sequence on the replacement region of the first single stranded replacement nucleic acid.

The advantages and preferred sub-embodiments of this embodiment of double recombination are the same as the advantages and preferred sub-embodiments of the other embodiment of double recombination discussed above. The skilled person will also appreciate that preferred features described infra of the integers in steps a) and b) of the methods of the invention may be applied independently to the analogous integers in steps c) and d) of this embodiment.

Both embodiments of double recombination may be varied such that exposure to the first and second single stranded replacement nucleic acid occurs simultaneously. According to this variation, the invention therefore provides an embodiment of the methods of the invention wherein steps a)-c) are:

- a) generating
  - i) a first single stranded replacement nucleic acid from a first double stranded nucleic acid, wherein the first double stranded nucleic acid is adapted at one or both of its 5' ends such that preferential degradation of one strand and/or strand separation generates the first single stranded replacement nucleic acid, wherein the first single stranded replacement nucleic acid comprises a 5' region that is identical to sequence on the target nucleic acid, a 3' region that is identical to sequence on the target nucleic acid and a replacement region between the 5' and 3' regions that is not identical to sequence on the target nucleic acid, and
  - ii) a second single stranded replacement nucleic acid from a second double stranded nucleic acid, wherein the second double stranded nucleic acid is adapted at one or both of its 5' ends such that preferential degradation of one strand and/or strand separation generates the second single stranded replacement nucleic acid, wherein the second single stranded replacement nucleic acid comprises a 5' region that is complementary to a first sequence on the replacement sequence of the first single stranded nucleic acid, a 3' region that is complementary to a second sequence on the replacement sequence of the first single stranded nucleic acid and optionally a replacement region between the 5' and 3' regions that is not identical to sequence on the target nucleic acid,
- b) exposing the target nucleic acid to the first and second single stranded replacement nucleic acids under conditions suitable for recombination to occur between the first and second single stranded replacement nucleic acids and the target nucleic acid, and
- c) selecting a target nucleic acid whose sequence has been altered by inclusion of said first and second single stranded replacement nucleic acids.

The skilled person will appreciate that preferred features described infra of the integers in steps a)-c) of the methods of the invention may be applied independently to the analogous integers in steps a)-c) of this embodiment of the invention.

Similarly, the invention provides an embodiment of the other methods of the invention wherein steps a) and b) are:

- a) exposing the target nucleic acid to first and second single stranded replacement nucleic acids in the presence of Red beta, or a functional equivalent thereof under conditions suitable for recombination to occur between said first and second single stranded replacement nucleic acids and the target nucleic acid, wherein
  - i) the first single stranded replacement nucleic acid comprises a 5' region that is identical to sequence on the target nucleic acid, a 3' region that is identical to sequence on the target nucleic acid and a replacement region between the 5' and 3' regions that is not identical to sequence on the target nucleic acid, wherein the replacement region is at least 61 bases in length, and
  - ii) the second single stranded replacement nucleic acid comprises a 5' region that is complementary to a first sequence on the replacement region of the first single stranded replacement nucleic acid, a 3' region that is complementary to a second sequence on the replacement region of the first single stranded replacement nucleic acid and a replacement region between the 5' and 3' regions that is not identical to sequence on the target nucleic acid, wherein the replacement region is at least 61 bases in length, and
- b) selecting a target nucleic acid whose sequence has been altered by inclusion of the first and second single stranded replacement nucleic acids.

The skilled person will appreciate that preferred features described infra of the integers in steps a) and b) of the methods of the invention may be applied independently to the analogous integers in steps a) and b) of this embodiment of the invention.

The inventors have found that the efficiency of these embodiments of the variation of double recombination may be improved if the first single stranded replacement nucleic acid can anneal to the lagging strand of the target nucleic acid when it is replicating. The lagging strand can be identified from the direction of replication as discussed above.

In these variations of double recombination, the second single stranded replacement nucleic acid is capable of annealing to the first single stranded replacement nucleic acid by virtue of the complentarity between its 5' region (5' complementarity region) and the first sequence on the replacement region of the first single stranded replacement nucleic acid and its 3' region (3' complementarity region) and the second sequence on the replacement region. The efficiency of these embodiments may be improved if the replacement region of the second single stranded replacement nucleic acid does not anneal to the first single stranded replacement nucleic acid. Accordingly, in some embodiments, the replacement region of the second single stranded replacement nucleic acid is not complementary (particularly not 100% complementary) to sequence on the first single stranded replacement nucleic acid.

These variations of double recombination again make use of a first single stranded replacement nucleic acid "adaptor" that provides appropriate sequence for insertion of the second single stranded replacement nucleic acid. Any second single stranded replacement nucleic acid can be inserted provided that it has the appropriate 5' and 3' regions complementary to the first and second sequences on the replacement region of the first single stranded replacement nucleic acid. Once again, these 5' and 3' regions may be included in the second replacement nucleic acid by producing the second double stranded nucleic acid substrate by PCR using stock PCR primers designed to contain the 5' and 3' regions in the primers, or by ligation of small dsDNA fragments with the sequence of the 5' and 3' regions onto dsDNA sequences which do not already comprise these regions.

In a preferred embodiment, the replacement region of the second single stranded replacement nucleic acid comprise a selectable marker. For example, this selectable marker may be an antibiotic resistance marker, such as blasticidin, ampicillin, kanamycin or other markers known in the art.

Preferably, the 5' region of the first single stranded replacement nucleic acid is longer than 20 nucleotides, more preferably between 40 and 60 nucleotides. Similarly, it is preferred for the 3' region of the first single stranded replacement nucleic acid to be longer than 20 nucleotides, more preferably between 40 and 60 nucleotides. In the same way it is preferred for the 5' region of the second single stranded replacement nucleic acid to be longer than 20 nucleotides, more preferably between 40 and 60 nucleotides; and for the 3' region of the second single stranded replacement nucleic acid to be longer than 20 nucleotides, more preferably between 40 and 60 nucleotides.

Typically, the target nucleic acid will be comprised within a genome or an episome, e.g. a BAC or plasmid.

The first and second double stranded nucleic acids may be obtained from any source. In preferred embodiments, the first double stranded nucleic acid is a PCR fragment, a synthetic oligomer or a fragment obtained by gene synthesis. The second double stranded nucleic acid may similarly be a PCR fragment, a synthetic oligomer or a fragment obtained by gene synthesis. In other embodiments, the second double stranded nucleic acid is a fragment obtained by digestion of a vector.

It has now been found that an altered method, which reduces the stringency of selection steps compared to conventional methods, allows for elucidation of recombinants containing the long single stranded replacement nucleic acids. Thus, the present invention preferably uses less stringent selection for recombination than the method of Court et al (Annu Rev Genet, 2002, 36: 361-388). Conventional methods for selection use a concentration of antibiotic that is five times the lowest effective dose at which there is no growth of bacteria. However, the present invention preferably utilises the lowest effective dose of antibiotic, more preferably between 5-70% above the lowest effective dose, more preferably between 10-40% above the lowest effective dose, more preferably between 15-30% above the lowest effective dose, most preferably 20% above the lowest effective dose for the selection. Preferably, the host cell is incubated for 1 to 7 days, more preferably between 2 to 5 days, and then it is determined whether the sequence of the target nucleic acid has been altered by inclusion of said single stranded replacement nucleic acid. Thus, the selection step is preferably conducted over a longer period of time compared to conventional selection techniques.

Upon further enquiry, it has unexpectedly been found that the ability of Red beta alone to utilize longer ssDNAs as substrates for recombination is not simply an extension of its ability to utilize single stranded oligonucleotides. In addition to ssOR, Red beta possesses a further activity for the utilization of longer ssDNAs. For convenience, recombination with longer ssDNAs mediated by Red beta is referred to herein as beta recombination. The difference between the mechanism involved in beta recombination and the mechanism involved in ssOR, which was known in the art, is established from four lines of evidence:

(i) only Red beta can mediate recombination with longer ssDNAs. Neither RecT nor Erf can do this, although all three can recombine single stranded oligonucleotides (FIG. 3). Therefore beta recombination is not simply scaled up ssOR.

(ii) Red beta-mediated recombination with oligonucleotides is repressed by the mismatch repair pathway (Constantino and Court, 2003, PNAS USA, 100:15748-15753; Li et al. Nuc. Acids. Res., 31:6674-6687; Oppenheim et al. Virology, 2004, 319(2): 185-189; Huen et al., Nuc. Acids Res. 34: 6183-6194). However beta recombination is not (FIG. 4). This also shows that beta recombination is distinct from ssOR. Thus, beta recombination and thus the methods of the invention may be carried out under conditions in which the mismatch repair pathway is operative.

(iii) specific mutations at the C-terminus of Red beta abolish its ability to mediate recombination with asymmetrically phosphorylated dsDNA substrates but not with single stranded oligonucleotides (FIG. 5).

(iv) co-expression of Red gamma has a strong stimulatory effect on beta recombination but no effect on ssOR (FIG. 7).

Furthermore, during examination of ssOR and ssDNA (beta) recombination mechanisms, an improved version of Red beta was found, which forms one aspect of the present invention. Red beta mutated at amino acid 176 from a glutamate into an alanine shows improved recombination efficiencies in both ssOR and beta recombination assays (FIG. 6). In contrast Red beta mutated at amino acid 191 from a glutamate into an alanine fully retains the same ssOR efficiency as the wild type protein yet has almost completely lost its ability to mediate beta recombination (FIGS. 5 and 6). Hence, preferably mutagenesis with either ss oligonucleotides or ssDNAs is performed with Red beta having a mutation at E176. Preferably, the residue numbering is in accordance with the sequence of Red beta shown in FIG. 10. The mutation may be a deletion, insertion or substitution but is preferably a substitution. The substitution may be to a conservative substitution or to a non-conservative substitution. Preferred substitutions are selected from Gly, Thr, Pro, Ala and Ser, with Ala being preferred. Thus, the invention also provides a method for performing homologous recombination comprising using a Red beta having a mutation at position E176, as described above. Preferably, the homologous recombination is performed according to a method of the invention. The homologous recombination may be single stranded oligonucleotide repair. All of these mutant forms of Red beta form aspects of the present invention. Preferably such mutant forms exhibit greater recombination efficiency than wild type Red beta protein.

Engineering with ssDNA rather than dsDNA is useful because it permits experimental configurations which avoid problems caused by unwanted double strand breaks. Both homologous and illegitimate recombination begin with a double strand break in DNA and a double strand break repair (DSBR) mechanism. Double strand breaks occur naturally for several reasons, particularly as a consequence of failures at the DNA replication fork. Upon random occurrence of a double stranded break, the broken ends need to be processed by a DSBR mechanism to re-initiate replication, and hence cause recombination. In *E. coli*, this recombination is almost always homologous recombination, which can perfectly reset the replication fork so no mutation occurs. Alternatively, homologous recombination can occur between sequence repeats which lie either side of the break. The repeats do not have to be near the break but can be tens of thousands of base pairs apart. As opposed to the *E. coli* genome, cloned DNA often contains a much larger content of repeated sequences and so repeat directed deletion due to DSBR at random double strand breaks can be a major problem and is the major reason for instability of cloned sequences. It is also the reason why cloning hosts are generally recA deficient, because the absence of RecA incapacitates endogenous DSBR. When engineering with dsDNA and DSBR, the possibility of unwanted rearrangements in cloned DNA sequences via DSBR is reactivated. This can be particularly troublesome with highly repetitive sequences, such as certain sections of higher eukaryotic genomes, which often carry many repeats derived from transpositional events, as well as prokaryotic secondary metabolite pathways, such as polyketide and non-ribosomal peptide synthase pathways, which are based on several repeats of coding modules.

Advantageously, with long ssDNAs and Red beta and Red gamma, or Red beta only, it is possible to engineer without turning on a DSBR pathway (FIG. 9). In the presence of Red beta, DSBR requires Red alpha to prepare double strand breaks for Red beta to mediate recombination. Hence omitting Red alpha reduces recombination from randomly occurring double strand breaks. Thus, the method for creating a mutation is preferably carried out in the absence of Red alpha or a functional equivalent thereof. Because there is no natural source of linear ssDNA molecules, expressing Red beta does not activate a problematic endogenous mechanism. Therefore cloned DNA is inherently more stable and the ratio of intended to unwanted recombinants is significantly better. Thus, the invention provides methods in which recombination using long ssDNAs and Red beta in the absence of Red alpha may be carried out in a RecA background. These advantages of engineering with ssDNA also apply to engineering with single stranded oligonucleotides mediated by RecT or Erf in the absence of their respective exonucleases. However, as discussed above, engineering applications with single stranded oligonucleotides using RecT or Erf are limited to directed mutagenesis followed by physical screening and do not readily permit the introduction of new genes or the advantages of genetic selection as is possible with beta recombination. Thus, the method of the present invention provides numerous advantages over the prior art.

It has now surprisingly been found that recombination with a single stranded replacement nucleic acid mediated by Red beta is greatly enhanced by co-expression of Red gamma (see Example 5 and FIG. 6). This is surprising because Red gamma is thought to inhibit RecBCD, which is a dsDNA exonuclease and thus would not be expected to have any effect on ssDNA. Thus, although Red gamma expression is not essential when engineering with single stranded replacement nucleic acids, Red gamma is preferably also present in the methods of the invention as it leads to increased efficiency of recombination. Thus, in a preferred embodiment, the method of the invention is carried out in the presence of Red beta and Red gamma, wherein Red alpha is absent.

Furthermore, whilst exploring ssOR and beta recombination mechanisms, a mutation in the *E. coli* host was found that enhances both ssOR (for the lagging strand) and beta recombination. An *E. coli* host mutated for the exonuclease, sbcB, shows both greatly enhanced ss oligonucleotide directed mutagenesis, when the oligonucleotide anneals to the lagging strand template, and ssDNA directed mutagenesis. Hence a preferred embodiment for the invention is to perform ssOR and/or beta recombination in a host cell mutated for exonucleases, specifically an *E. coli* host mutated for sbcB. Thus, the invention also provides a method for performing single stranded oligonucleotide repair and/or beta recombination comprising performing the homologous recombination in a host cell in which the activity of its endogenous sbcB exonuclease, or the orthologue or functional equivalent thereof, has been inactivated or reduced. Also provided is a host cell in which the activity of its endogenous sbcB exonuclease, or the orthologue thereof, has been reduced or inactivated relative to its wild-type counterpart; such a host cell forms an aspect of the present invention. Preferably, the host cell is *E. coli*. SbcB or its orthologue or functional equivalent may be inactivated or the activity thereof may be reduced by way of a mutation. Preferably, the mutation inactivates the SbcB or its orthologue. Any suitable mutation is envisaged, for example, a deletion, insertion or substitution. For example, the entire gene encoding the exonuclease may be deleted or one or more point mutations may be used to inactivate the SbcB or its orthologue. The exonuclease may be inactivated in any other appropriate way, for example, by gene silencing techniques, by the use of exonuclease-specific antagonists or by degradation of the exonuclease.

Methods which utilise the mutant of the SbcB/orthologue/functional equivalent described above, may be a method according to the present invention. Also provided is the use of the SbcB mutants (and corresponding orthologues/functional equivalents) in broader aspects of homologous recombination technology. Thus, there is a provided a method of altering the sequence of a target nucleic acid comprising (a) bringing a first nucleic acid molecule into contact with a target nucleic acid molecule in the presence of a phage annealing protein, or a functional equivalent or fragment thereof, wherein said first nucleic acid molecule comprises at least two regions of shared sequence homology with the target nucleic acid molecule, under conditions suitable for repair recombination to occur between said first and second nucleic acid molecules and wherein the functional equivalent or fragment retains the ability to mediate recombination and wherein the activity of the host's endogenous sbcB exonuclease or orthologue or functional equivalent thereof has been inactivated or reduced; and (b) selecting a target nucleic acid molecule whose sequence has been altered so as to include sequence from said first nucleic acid molecule. Preferably, the phage annealing protein is Red beta or a functional equivalent thereof. The method may be carried out in the absence or presence of one or both of Red alpha and/or Red gamma or their functional equivalents.

A further advantage relates to the use of counterselection. Counterselection is a useful way to achieve a seamlessly mutated product without any remnant operational sequences of the engineering. Usually, engineering with homologous recombination requires insertion of a selectable gene. Often the continued presence of this gene is not optimal. It can be removed by either of two main strategies. If it is flanked by site specific recombination target sites (RTs) like loxP or FRT, then expression of the corresponding site specific recombinase will delete the gene. However this strategy leaves a 34 bp 'scar', which is the remaining RT. Counterselection can be used to replace the selected gene and leave no scar. In this case, the replacing DNA does not contain a selectable aspect, rather the removal of a counterselectable gene by homologous recombination with the replacing DNA provides the selection pressure.

Counterselectable genes include rpsL, which makes those *E. coli* hosts that are naturally resistant to streptomycin sensitive again. Its removal restores resistance. Another counter selectable gene is SacB, which conveys toxicity to sucrose.

Although counterselection is potentially powerful, the major problem relates to the elimination of the counterselection gene by intramolecular recombination through flanking repeats rather than by the intended homologous recombination. Most of this intramolecular recombination is due to DSBR. Therefore, recombination with ssDNA and Red beta without Red alpha can improve the utility of counterselection because it will not provoke DSBR and consequent undesired intramolecular recombination.

A number of different types of nucleic acid molecule may be targeted using the methods of the invention. The target nucleic acid molecule may be a circularised or linear molecule, and may thus be expressed transiently or permanently in the host cell in this aspect of the invention, for example, from the chromosome or from an extrachromosomal element. Accordingly, intact circular double-stranded nucleic acid molecules (DNA and RNA), such as plasmids, and other extrachromosomal DNA molecules based on cosmid, P1, BAC or PAC vector technology may be used as the target nucleic acid molecule according to the invention described above. Examples of such vectors are described, for example, by Sambrook and Russell (Molecular Cloning, Third Edition (2000), Cold Spring Harbor Laboratory Press) and Ioannou et al. (Nature Genet. 6 (1994), 84-89) and the references cited therein.

The target nucleic acid molecule may also be a host cell chromosome, such as, for example, the *E. coli* chromosome. Alternatively, a eukaryotic host cell chromosome (for example, from yeast, *C. elegans, Drosophila*, mouse or human) or eukaryotic extrachromosomal DNA molecule such as a plasmid, YAC and HAC can be used. Alternatively, the target nucleic acid molecule need not be circular, but may be linear. Preferably, the target nucleic acid molecule is a double stranded nucleic acid molecule, more preferably, a double-stranded DNA molecule.

Either the (resulting) single stranded replacement nucleic acid molecule or the target nucleic acid molecule should contain an origin of replication. In this way, the origin of replication may be incorporated into the target nucleic acid molecule by beta recombination, in order that the nucleic acid molecule may be propagated in the host cell. In the case that the replacement, but not the target nucleic acid molecule carries an origin plus selectable marker gene, the method of the invention may utilise the methods for nucleic acid subcloning as described by Zhang et al., Nature Biotech 18 (2000), 1314-1317; also see International patent application WO 01/04288.

The double stranded nucleic acid substrate and the single stranded replacement nucleic acid are preferably DNA, but may alternatively include RNA or one or more modified nucleotides.

It should be noted that the double stranded nucleic acid substrate or single stranded replacement nucleic acid molecule is not necessarily a single species of nucleic acid molecule. For example, it is possible to use a heterogeneous population of double stranded or single stranded nucleic acid molecules, for example, to generate a DNA library, such as a genomic or cDNA library.

The replacement nucleic acid molecule may be derived from any source. For example, the replacement nucleic acid molecule may be synthesized by a nucleic acid amplification reaction such as a PCR reaction, for example, in which both of the DNA oligonucleotides used to prime the amplification contain, in addition to sequences at the 3'-ends that serve as a primer for the amplification, one or the other of the two sequence identity regions. Using oligonucleotides of this design, the nucleic acid product of the amplification can be any nucleic acid sequence suitable for amplification and will additionally have a sequence identity region at each end.

The sequence of Red beta is well known in the art (e.g. Iyer, L. M. et al., BMC Genomics, 2002, 3(1):8). Preferably, the Red beta for use in the invention comprises or consists of the sequence shown in FIG. 10, or is a variant thereof as discussed below.

The invention also includes the use of functional equivalents of Red beta, Red alpha and Red gamma, provided that the functional equivalents retain the ability to mediate beta recombination, as described herein. Examples of functional equivalent molecules include Red beta, Red alpha and Red gamma proteins that comprise amino acid substitutions, insertions and/or deletions from the wild type sequence, provided that these changes do not adversely affect the function of the protein in mediating beta recombination as described herein. It is recognized that the genes encoding Red beta, Red alpha and Red gamma may be considerably mutated without materially altering the beta recombination function of Red beta, Red alpha or Red gamma. The genetic code is well-known to be degenerate, and so different codons may encode the same amino acid. Further, the introduction of an amino acid mutation may result in a conservative mutation that has no material impact on the essential functions of Red beta, Red alpha or Red gamma. Methods for effecting conservative substitutions are well known in the art. Additionally, part of the Red beta, Red alpha or Red gamma polypeptide chain may be deleted without impairing or eliminating the beta recombination function. The skilled person will be able to test for functional equivalence of any variant using standard methods known in the art. Likewise, insertions or additions may be made in the Red beta, Red alpha or Red gamma polypeptide chain, for example, adding epitope tags, without impairing or eliminating its essential functions. Such functional equivalents will preferably possess a nucleotide sequence identity of at least 40%, at least 50%, at least 60%, at least 70%, at least 80%, at least 90%, at least 95%, at least 98%, at least 99% with the wild type Red beta, Red alpha or Red gamma sequence. For example, using standard tools to search for protein similarities, Iyer et al identified many new Red beta-like proteins (Iyer L M, Koonin E V, Aravind L. (2002), "Classification and evolutionary history of the single-strand annealing proteins, RecT, Red beta, ERF and RAD52", BMC Genomics. 3(1):8). As genome sequences are added to the databases, many more similar proteins are being added.

For example, Red beta proteins having one or more mutations (for example, 2, 3, 4, 5, 6, 7, 8, 9, 10, 11, 12, 13, 14 or 15 or more mutations) relative to the sequence provided in FIG. 10 may be used in the invention. The mutations may be insertions, deletions or substitutions. Examples of mutations are A255T, A255S, and/or A246V.

As mentioned above, mutagenesis with either ss oligonucleotides or ssDNAs is advantageously performed with Red beta having a mutation at E176. The mutation may be a deletion, insertion or substitution but is preferably a substitution. The substitution may be to a conservative substitution or to a non-conservative substitution. Preferred substitutions are to an amino acid selected from Gly, Thr, Pro, Ala and Ser, with Ala being preferred.

Also included as functional equivalents are fragments of the Red beta, Red alpha or Red gamma proteins, such as truncated variants, and fusion proteins, of which the sequence of the Red beta, Red alpha or Red gamma protein forms a part, that retain the ability to mediate beta recombination (for example, see Muyrers et al., Genes Dev 14 (2000), 1971-1982). It is considered that the identification of such functional equivalents is within the ability of the skilled addressee.

Also included as functional variants are variants of Red beta, Red alpha or Red gamma that have been optimised and/or evolved, through, for example DNA shuffling (Stemmer, W. P. Nature, 370, 389-391, (1994).

However, as mentioned above, only Red beta can mediate recombination with longer ssDNAs. The other single stranded phage annealing proteins RecT and Erf cannot do this. Thus, functional equivalents of Red beta for use in methods of the invention that use long ssDNAs as the single stranded replacement nucleic acid preferably do not encompass RecT or Erf.

The method of the invention may be effected, in whole or in part, in a host. Suitable hosts include cells of many species, including viruses and parasites, prokaryotes and eukaryotes, although bacteria, such as gram negative bacteria, are preferred. More preferably, the host cell is an enterobacterial cell, such as a *Salmonella, Klebsiella, Bacillus, Photohabdus, Neisseria* or *Escherichia coli* cell (the method of the invention works effectively in all strains of *E. coli* that have been tested). Particular examples of prokaryotic host cells in which the activity described herein has been demonstrated to occur include strains WS991 (Invitrogen), DK1 (New England Biolabs) and DH10B (Gibco BRL).

It should be noted, however, that the method of the present invention is also suitable for use in eukaryotic cells or organism such as fungi, plant or animal cells, as well as viral and parasitic cells and organisms. Suitable eukaryotic cells for the method of the invention include those in which DNA engineering by homologous recombination is known to be feasible, including, for example, most *S. cerevisae* strains, mouse ES cells (such as E14 and R1; see Joyner, Gene Targeting, a practical approach, (2000) target edition, Oxford University Press Inc, New York) and certain somatic cell lines such as DT-40. Moreover, any cells or species which contain functional pathways for DNA repair (which include most cells, for example, see Stucki et al. Prog. Nucleic Acid Res Mole Biol 65 (2000) 261-298; Hansen and Kelley, J. Pharmacol. Exp. Ther. 295 (2000) 1-9) are likely to be suitable.

Preferably, the host cell used for beta-recombination can be any cell in which Red beta, or a functional equivalent or fragment thereof is expressed. For example, the host cell may comprise the Red beta gene located on the host cell chromosome or on a non-chromosomal nucleic acid molecule, such as a vector, optionally expressed from a promoter, such as the regulatable arabinose-inducible BAD or lac promoters or the strong constitutive promoter EM-7. Alternatively, Red beta may be expressed from a mRNA which is introduced with the replacement and, potentially, the target nucleic acid molecule. The beta recombination reaction faithfully integrates the sequence from the single stranded replacement nucleic acid. For example, in *E. coli*, all recombined molecules are proof-read by the endogenous replication and repair systems. As a result, the fidelity of sequence reproduction is extremely high.

In the system that is described here, the expression of Red beta may be controlled by a regulatable promoter. In this manner, the recombinogenic potential of the system is only elicited when required and, at other times, possible undesired recombination reactions are limited. Since many undesired recombination reactions occur through homologous recombination by double strand break repair (Muyrers et al., Genes Dev 14 (2000), 1971-1982; Zhang et al. Nature Biotech, 18 (2000), 1314-1317), and therefore require the expression of both components of a phage protein pair (Muyrers et al., Genes Dev 14 (2000), 1971-1982), the risk of such unwanted recombination is greatly lowered in the presence of the annealing protein only. Moreover, given the independence of the system described here on the presence of RecA, this risk is further reduced by carrying out the method in a host cell in which no RecA is expressed.

The method of the invention may comprise the contacting of the single stranded replacement nucleic acid and target nucleic acid molecules in vivo. In one embodiment, the double stranded nucleic acid substrate or single stranded replacement nucleic acid may be transformed into a host cell that already harbours the target nucleic acid molecule. In a different embodiment, the replacement and target nucleic acid molecules may be mixed together in vitro before their co-transformation into the host cell. Of course, one or both of the species of nucleic acid molecule may be introduced into the host cell by any means, such as by transfection, transduction, transformation, electroporation and so on. For bacterial cells, the preferred method of transformation or cotransformation is electroporation.

The invention may be initiated entirely in vitro, without the participation of host cells or the cellular recombination machinery. Phage annealing proteins such as Red beta are able to form complexes in vitro between the protein itself, a single stranded replacement nucleic acid and a double-stranded target nucleic acid molecule (Noirot and Kolodner, J. Biol. Chem. 273 (1998), 12274-12280). One example of such a complex is that formed between Red beta, a single stranded replacement nucleic acid and an intact circular plasmid. Such complexes lead to the formation of complexes that are herein termed "joint molecules" (consisting, in this example, of the plasmid and the single stranded replacement nucleic acid). Such joint molecules have been found to be stable after removal of the phage annealing protein. The formation of stable joint molecules has been found to be dependent on the existence of shared identity regions between the single stranded replacement nucleic acid and the plasmid.

In vitro, the formation of joint molecules between a single stranded replacement nucleic acid and a homologous target sequence is dependent only on the presence of the annealing protein. No other exogenous components are required for the reaction, and no specific cellular manipulation is necessary for the method to proceed. For example, RecBCD need not be inactivated; the method still works effectively in a RecBCD+ background (see International patent application WO 02/062988). This system is immensely powerful and may be used to introduce substitutions, deletions and insertions into nucleic acid molecules, as desired.

It is also proposed that a single-stranded replacement nucleic acid molecule that is coated by a Red beta protein, herein referred to as a "coated molecule", is able to recombine with higher efficiency compared to a "naked", uncoated nucleic acid molecule. One embodiment of the invention therefore provides the use of an isolated complex of Red beta, or a functional equivalent or fragment thereof and a single stranded replacement nucleic acid as a template for beta recombination processing, leading to the formation of recombinant molecules in a host cell that does not need to express any phage annealing protein whatsoever. Delivery of coated or joint molecules to the host cell (which in many cases contains the target molecule) can be of several types: transformation, transfection, electroporation, etc. (also eukaryotic delivery techniques), or by using Red beta that carries a tag which allows it to cross the cell wall, such as the TAT (Nagahura et al., Nature Med. 4 (1998), 1449-1452; Schwarze et al. Science 285 (1999), 1569-1572) or kFGF tag (Delli Bovi et al., Cell 50 (1987), 729-737; Yoshida et al., Proc. Natl. Aad. Sci. USA 84 (1987), 7305-5309; Peters et al., Proc. Natl. Acad. Sci. USA 86 (1989) 5678-5682).

It is a great strength of the method of the invention that no complex selection steps are necessary to select for recombined molecules. After contacting the replacement and target nucleic acid molecules under conditions which favour beta recombination between the two molecular species, one or more nucleic acid molecules must be selected that represent species in which beta recombination between replacement and target nucleic acid molecules has occurred. This procedure can be carried out by several different methods, as will be clear to the skilled reader. Preferably, selection is using PCR, although hybridisation reactions, using techniques of blotting, or using assays, may also be used (see Sambrook and Russell; loc. cit.). Despite the high efficacy of the method of the invention, there may be occasions when selectable gene steps may be included in the methodology in order to enhance the efficiency of the method, including methods of antibiotic selection, and selection using site-specific recombinases. Examples of suitable selection methods are described, for example, in International patent application No. WO 99/29837.

The invention will now be described in detail with reference to the following specific examples. It will be appreciated that modification of detail may be made without departing from the scope of the invention.

BRIEF DESCRIPTION OF THE FIGURES

FIG. 5: Mutant versions of Red beta can still mediate ssOR but are defective for beta recombination;

FIG. 6 is based on the same assay as FIG. 5, but six more mutations were examined, as indicated in panel A; panel B is a bar graph showing recombination efficiencies for the wild type (wt) and mutant versions evaluated in the ssOR assay for both strands (LD—the oligonucleotide anneals to the leading strand template; LG—the oligonucleotide anneals to the lagging strand template), and the ssDNA recombination assay using two identical dsDNA substrates except for opposite, asymmetrical phopshothioloate (S) or 5' phosphate (P) as indicated; in the bar graph shown in panel C, the results of panel B (preferred strand) were plotted for ssOR (y-axis) and ssDNA (x-axis); panel D shows a plot showing ssDNA recombinants (ssPS) (x-axis) relative to ssOR recombinants (syLG) (y-axis);

FIG. 9: Reduced intramolecular recombination after recombineering with Red beta and long ssDNAs without Red alpha.

EXAMPLES

Example 1

The Single Stranded Replacement Nucleic Acid

Figure 1:
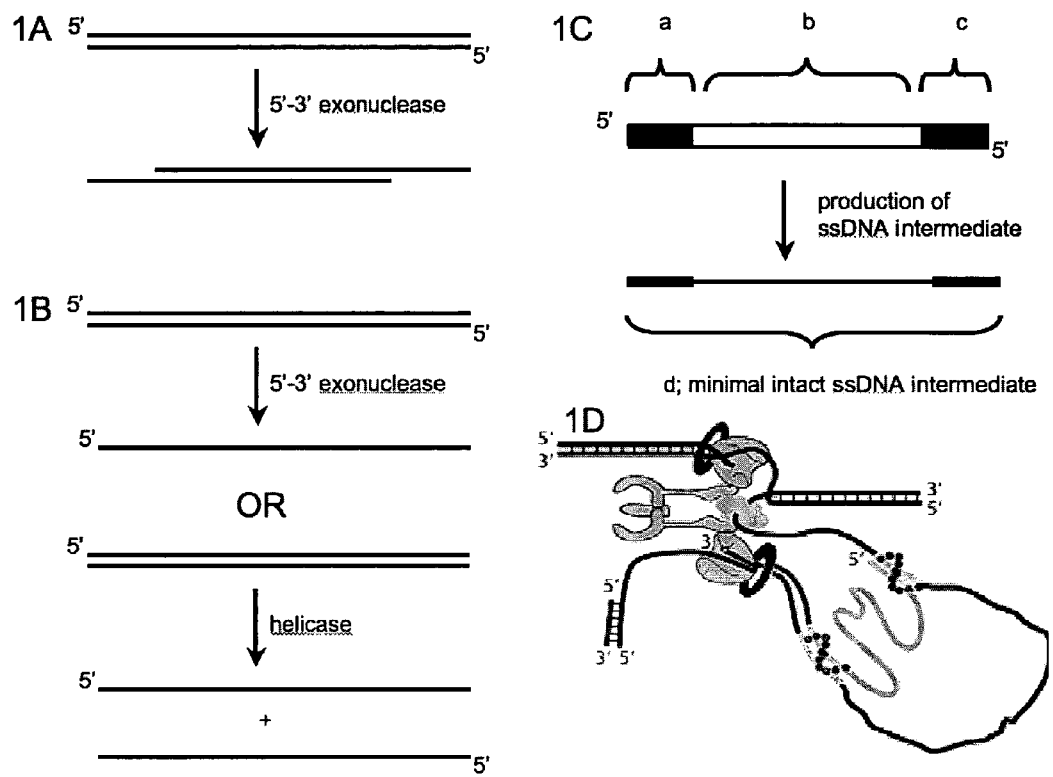
FIG. 1: New insight into a single stranded mechanism for homologous recombination and a specification of functional regions in the double stranded nucleic acid substrate; panel A shows the existing model for the initiation of homologous recombination by dsDNA; panel B shows the new mechanism elucidated by the present invention in which full length ssDNAs are produced from the dsDNA substrate; panel C shows a schematic diagram of an example of a double stranded nucleic acid substrate for use in the invention; panel D shows the proposed reaction intermediate in which a replication fork is shown proceeding from left to right.

A schematic diagram of an example of a double stranded nucleic acid substrate for use in the invention is provided in FIG. 1C, where the double stranded nucleic acid substrate is illustrated at the top showing three features from 5' to 3', denoted (a). (b) and (c) in the top strand and (a'), (b') and (c') running 5' to 3' in the bottom strand, respectively. The top strand in this example represents the strand that will become the single stranded replacement nucleic acid. Section (a) represents the 5' region that is identical to sequence on the target nucleic acid. Section (c) represents the 3' region that is identical to sequence on the target nucleic acid. Sections (a) and (c) anneal to their complementary sequences on the target nucleic acid, preferably on the lagging strand template at the replication fork. Sections (a) and (a') are preferably at the 5' end of their respective strands, but there may be additional sequence 5' to sections (a) and (a'). Sections (c) and (c') are preferably at the 3' ends of their respective strands, but there may be additional sequence 3' to sections (c) and (c'). Such additional 5' and 3' sequences may be as short as one nucleotide or may be up to several kilobases in length. Where additional 5' and/or 3' sequences are present in the double stranded nucleic acid substrate, these are preferably also present in the resulting single stranded replacement nucleic acid although embodiments are also envisaged in which the additional 5' and/or 3' sequences are lost prior to recombination taking place. The one or both 5' adaptions are preferably at the 5' ends of one or both of sections (a) and (a'), but may alternatively be at the 5' end of the additional sequence or sequences 5' to one or both of sections (a), and (a'). Preferably, the double stranded nucleic acid substrate is asymmetrically adapted at its 5' ends. Section (b), between the 5' and 3' regions, represents the replacement region. This region may be any length from zero nucleotides up to hundreds of kilobase pairs.

Example 2

Asymmetrically Ended Double Stranded DNA Substrates Function More Efficiently for Red Mediated Recombination Example 2 was conducted to show that Red alpha/Red beta recombination proceeds through a full length ssDNA intermediate. Two assays were conducted (see FIG. 2), both employing the same DNA fragment as a dsDNA substrate, which is used in four versions illustrated in FIG. 2. This dsDNA substrate was approximately 500 bps long and encoded the blaticidin resistance gene (bsd) flanked at each end by 50 by identity regions to regions on either pBelo-BAC11 or the E. coli chromosome. The four versions only differ according to the presence of a 5' phosphate (P) or hydroxyl group (0). These four fragments were recombined into a BAC (bacterial artificial chromosome; top panel) or into the E. coli chromosome (bottom panel). The targets in the BAC or chromosome were either in one configuration or inverted (bla and bla-inv respectively). This alters the target with respect to the origin of replication, which changes the leading strand to the lagging strand.

In all cases, the asymmetrically phosphorylated substrate which, after digestion by Red alpha of the 5' phosphorylated strand, leaves the strand that can anneal to the lagging strand template and prime Okazaki fragment synthesis, is the most efficient. It is more efficient than its counterpart or the symmetrically phosphorylated (PP) or unphosphorylated (OO) substrates. Thus, asymmetrically ended double stranded DNA substrates function more efficiently for Red mediated recombination.

Example 3

Red Beta but not Erf or RecT can Mediate Beta Recombination

Figure 3A:
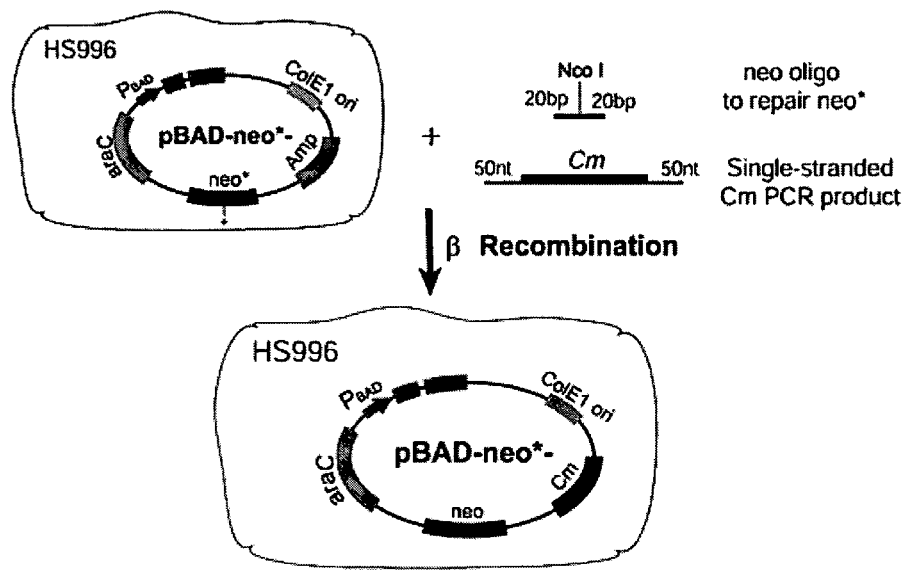
FIG. 3: Red beta but not Erf or RecT can mediate beta recombination with long ssDNAs; panel A shows in the top part a schematic representation of an assay based on recombination of a plasmid target, pBAD-neo*, in $E.$ $coli$ HS996 in the presence of either Red beta, Erf or RecT proteins expressed from the same plasmid; panel A shows in the bottom part the table showing the results of the assay; panel B shows a schematic representation of a further assay, in which BACs were used as the target; panel C shows a histogram indicating that all three proteins can mediate ssOR with the expected reference for the oligonucleotide which annealed to the lagging strand template (Lg)

In order to test whether beta recombination may be carried out by Erf or RecT in addition to Red beta, the inventors carried out an assay based on recombination of a plasmid target, pBAD-neo*, in E. coli HS996 in the presence of either Red beta, Erf or RecT proteins expressed from the same plasmid (see FIG. 3A, upper panel). The cells were co-transformed with a single stranded oligonucleotide to repair the neo* gene to generate kanamycin resistance, which serves to measure ssOR, and a ssDNA substrate prepared by boiling a PCR product made from the gene for chloramphenicol (Cm) resistance. The PCR product includes terminal regions of sequence identity to the amp gene in the plasmid, so that single stranded DNA recombination will replace ampicillin resistance with chloramphenicol resistance. The results are shown in the table in FIG. 3A. Whereas ssOR worked for all three, recombination with the long ssDNA substrate (beta recombination) was only efficient with Red beta.

Figure 2:
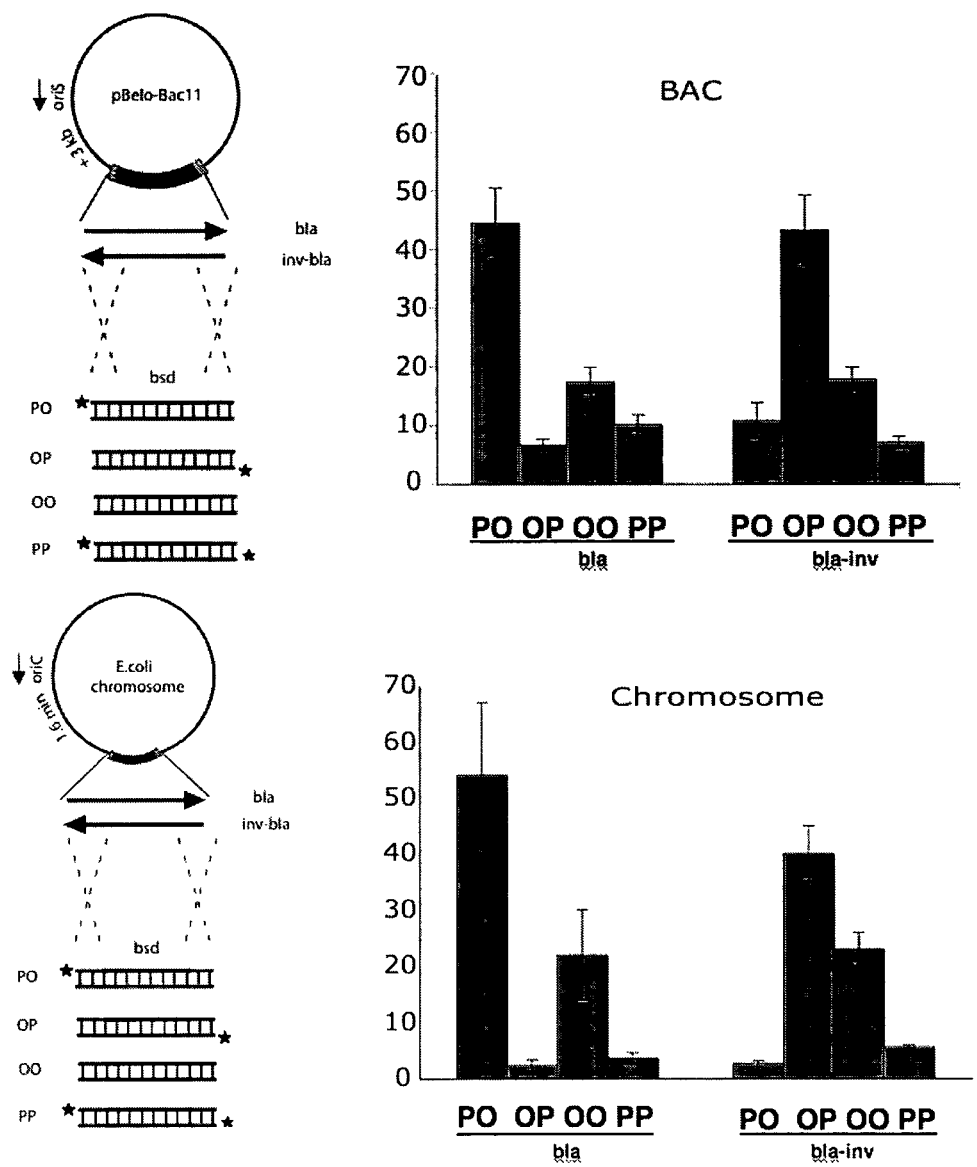
FIG. 2: Asymmetrically ended double stranded nucleic acid substrates function more efficiently for Red mediated recombination.
Figure 3B:
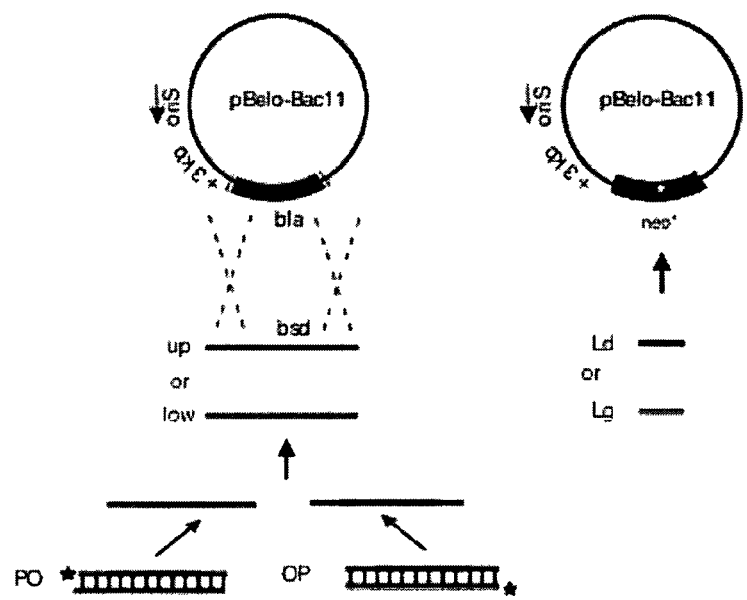
Figure 3C:
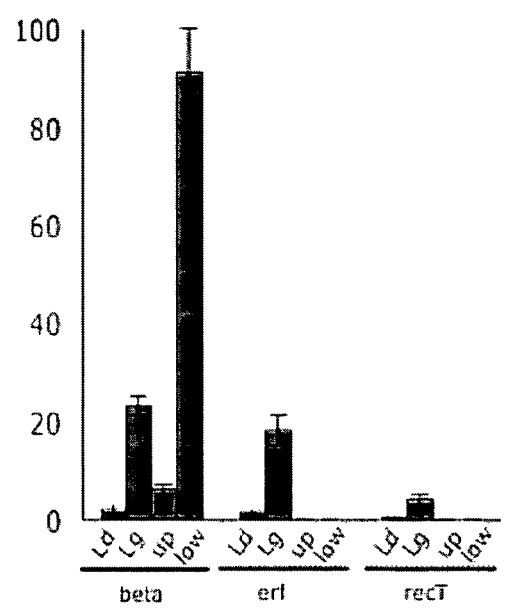

A further assay was conducted in which BACs were used as the target (see FIG. 3B). One BAC is the same target as shown in FIG. 2 and the other contains the neo* gene which can be repaired by ssOR as above. The longer ssDNA substrates were prepared by digesting asymmetrically phosphorylated dsDNA substrates with Red alpha in vitro before electroporating them into E. coli containing the BAC target. The histogram in FIG. 3C shows that all three proteins can mediate ssOR with the expected preference for the oligonucleotide which annealed to the lagging strand template (Lg). However only Red beta can utilize the longer ssDNA substrates (up, low). The ssDNA which annealed to the lagging strand template (low) delivered more recombinants than its complement which annealed to the leading strand template (up).

Example 4

Figure 4A:
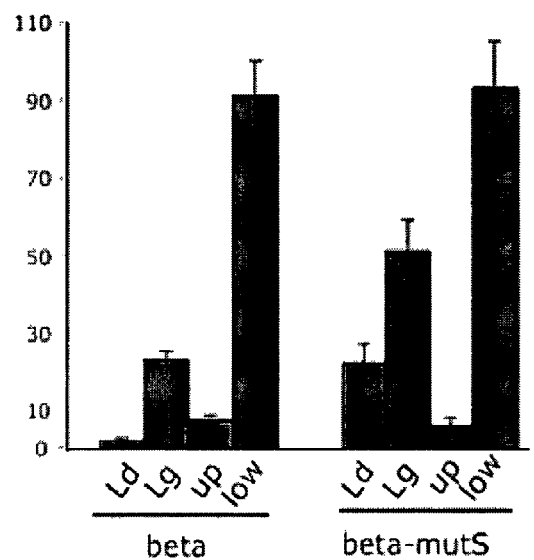
FIG. 4: Differential effects of host mutations on ssOR and beta recombination; panel A shows a bar graph comparing recombination efficiencies in $E.$ $coli$ strains HS996 and HS996 mutS; panel B is a bar graph showing the same data as in panel A, but in addition, the data from an $E.$ $coli$ strain mutated for sbcB is also shown; panel C shows a line plot illustrating the relationship between oligonucleotide directed mutagenesis and the size of the non-homologous nucleotide sequences that can be incorporated; different oligonucleotides were obtained that contained different lengths of non-homology between the 5' and 3' homology regions, as shown on the x-axis; the y-axis shows the number of correct recombinants obtained in the presence of either Red beta, Plubeta and RecT.
Figure 4B:
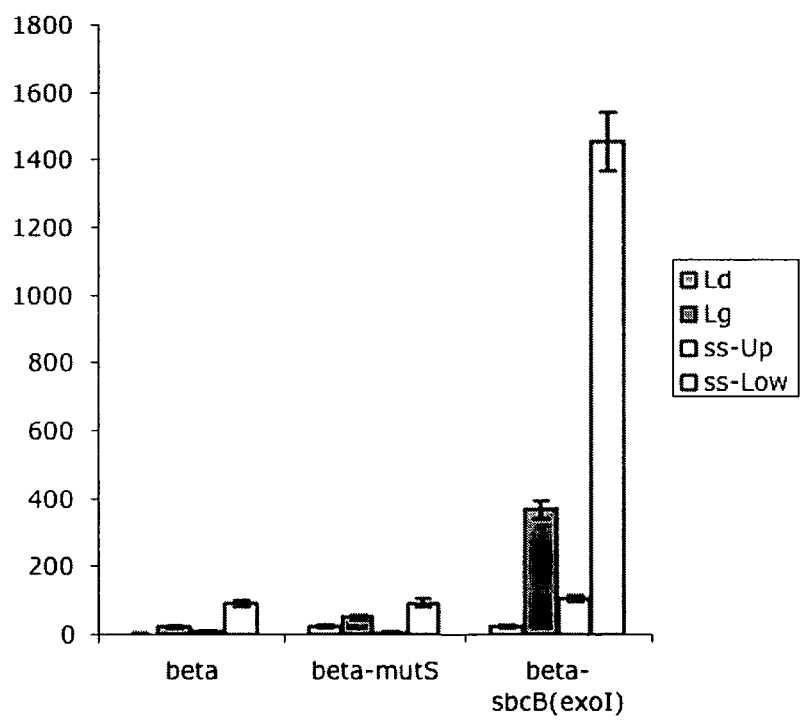
Figure 4C:
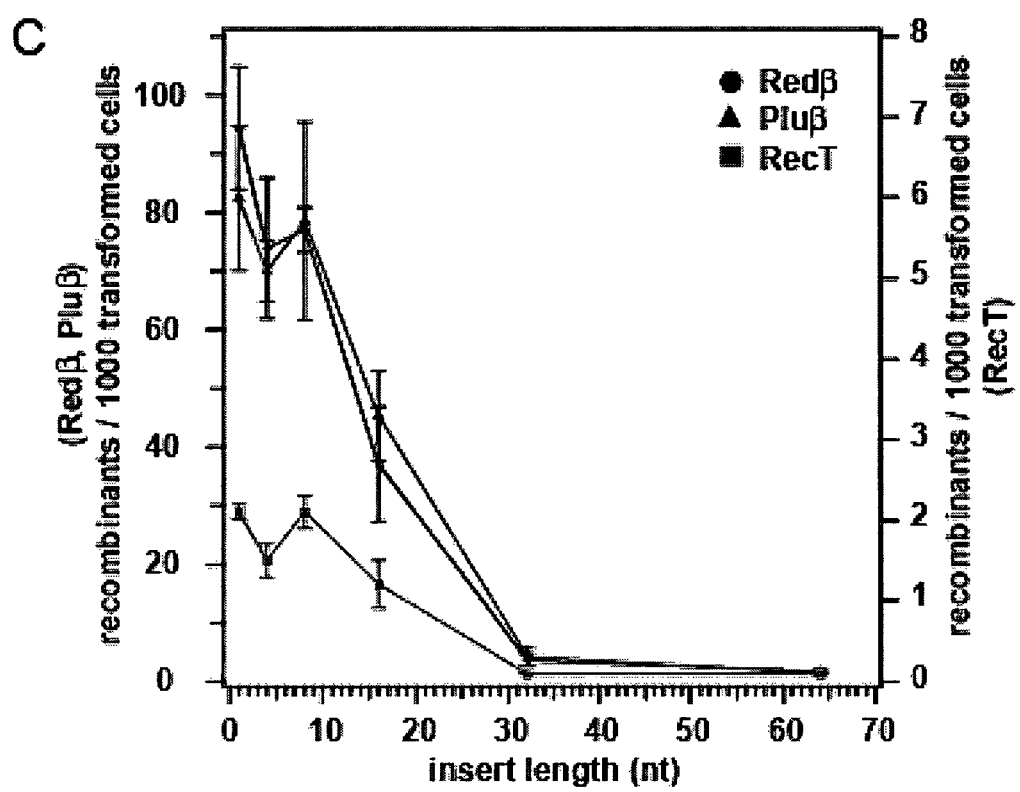

Differential Effects on ssOR and Beta Recombination of (a) Mutating the Mismatch Repair Pathway; (b) Mutating sbcB; (c) the Length of the Included Non-Homologous Nucleotide Sequence FIG. 4 is based on the same assay as described in Example 3 and shown diagrammatically in FIG. 3B. In FIG. 4A, recombination efficiencies were compared in E. coli strains HS996 and HS996 mutS. It is known from the literature that mutations in the mismatch repair (MMS) pathway increase ssOR efficiencies, especially on the leading strand (compare Ld, Lg). However this mutation had no effect on recombination with the longer ssDNA substrate (compare up, low). Thus, beta recombination is not affected by the mismatch repair pathway. In FIG. 4B, the same data as in A is shown except data from an E. coli strain mutated for sbcB is also shown. It can be seen that loss of sbcB leads to strongly increased beta recombination (ss-Up; ss-Low) and also for Lg by ssOR but not for Ld. In FIG. 4C, the relationship between oligonucleotide directed mutagenesis and the size of the non-homologous nucleotide sequences that can be incorporated is presented. Different oligonucleotides were obtained that contained different lengths of non-homology between the 5' and 3' homology regions, as shown on the x-axis. The y-axis shows the number of correct recombinants obtained in the presence of either Red beta, Plubeta (which is a Red beta like protein that was found in the genome sequence of Photohabdus luminscens) and RecT. As can be seen, recombination efficiency is greatly reduced by insertions of 30 nucleotides of non-homology. Below this size is the region of ssOR and almost all oligonucleotide directed DNA engineering exercises to date. At greater lengths of non-homology, which is the subject of this invention, Red beta delivers significantly greater numbers of correct recombinants.

Example 5

Mutant Versions of Red Beta can Still Mediate Ssor but are Defective for Beta Recombination FIG. 5 is based on the same assay as described in Example 3 and shown diagrammatically in FIG. 3B. The two mutant forms of Red beta were c-Strep, which has a strep-tag fused onto the C-terminus, and E191A, which is an exchange of amino acid 191 from glutamate to alanine. The results in FIG. 5 show that these mutant versions of Red beta can still mediate ssOR (lower panel; note again that the oligonucleotide that anneals to the lagging strand template (LG) works better than its complement (LD)). However these mutant versions are defective for beta recombination when compared to wt Red beta (upper panel).

Example 6

Figure 6:
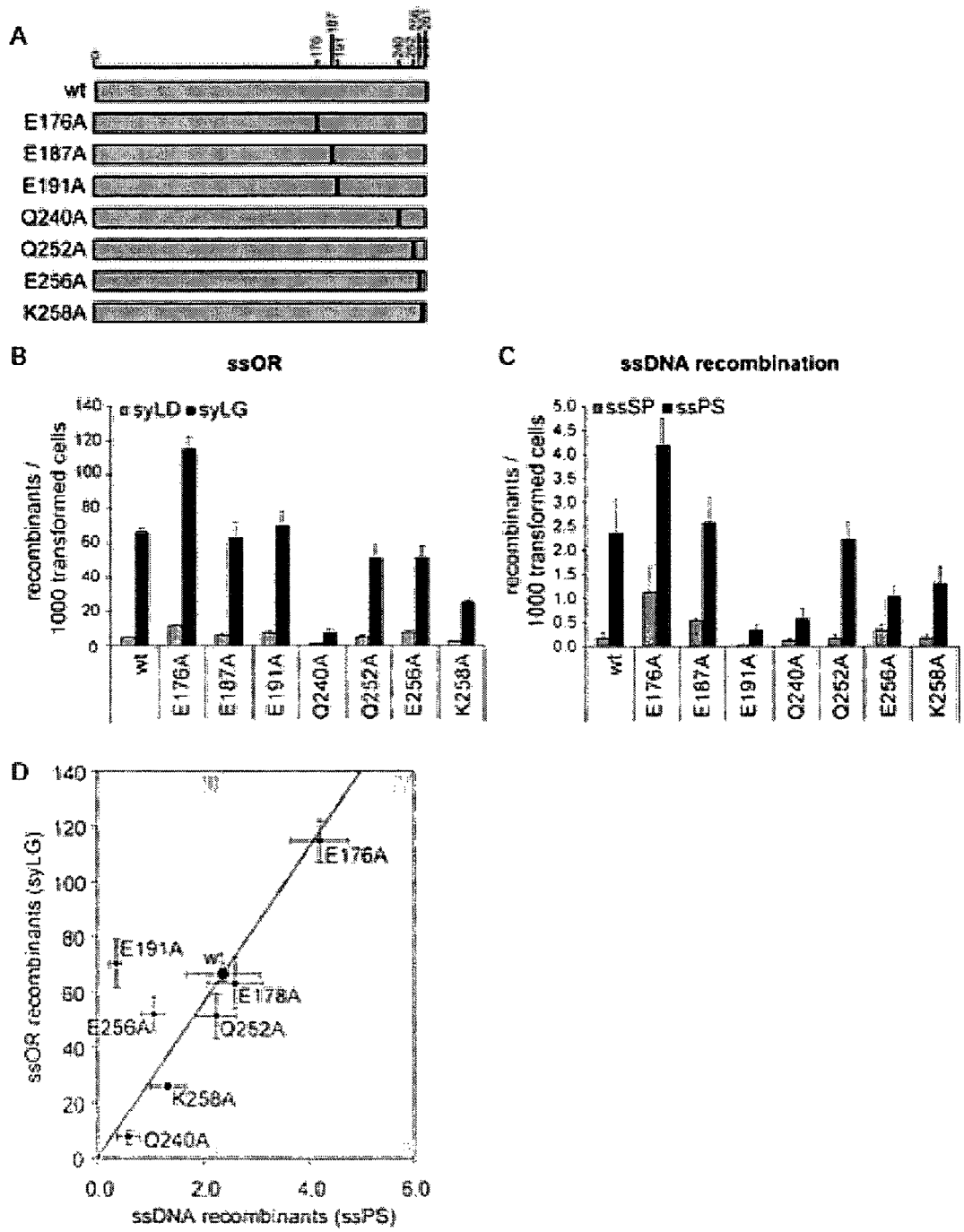
FIG. 6: Analysis of several Red beta mutations reveals a mutation showing improved performance with both ssOR and beta recombination, as well as a mutation showing selective loss of beta recombination.
Figure 7A:
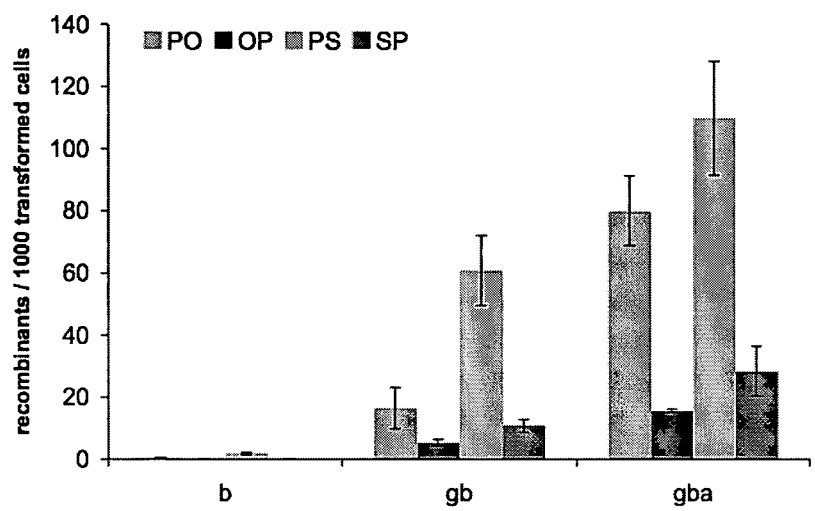
FIG. 7: Recombination mediated by Redβ is greatly enhanced by co-expression of Redγ whether Redα is present or not; and Redγ enhances beta recombination but not ssOR. Assymetrically phopshothiolated substrates function more efficiently for Red mediated recombination; panel A shows a bar graph illustrating the results of the experiment, in which the substrates were introduced as double stranded DNA; panel B shows a bar graph with the same data for Red beta only as does panel A, except with an amplified abscissa; panel C shows a bar graph illustrating the results of the experiment, in which only the asymmetrically phosphothioloated/phosphorylated substrates were used, either after predigestion in vitro with Red alpha to create a single stranded substrate (SP-ss or PS-ss), or directly as dsDNA substrates (SP-ds or PS-ds) and the results are presented in this order, left to right in the figure according to expression of Red beta only, Red gamma and Red beta, or Red gamma, Red beta and Red alpha; Panel D shows a bar graph illustrating the results of an ssOR assay, which demonstrates that Red gamma expression has little effect on oligonucleotide directed mutagenesis.
Figure 7B:
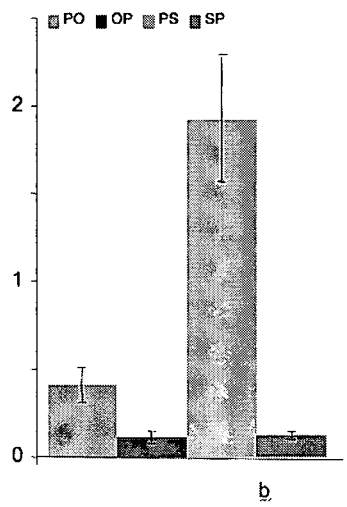
Figure 7C:
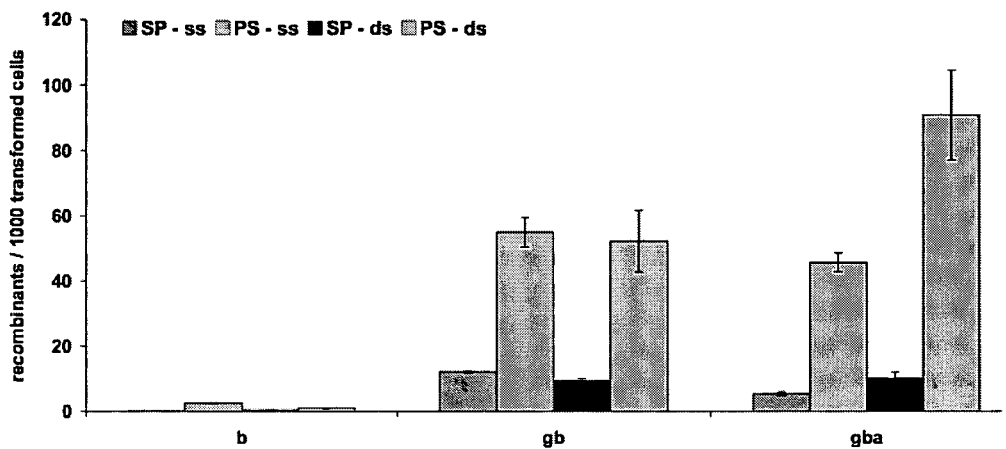
Figure 7D:
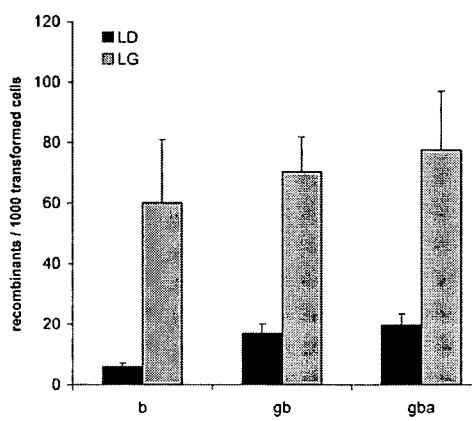

Further Data on Mutant Versions of Red Beta, Including a Mutation that Improves Recombination FIG. 6 is based on the same assay as FIG. 5 and includes the same data. Additionally six more mutations were examined as indicated in panel A. In panel B, recombination efficiencies for the wild type (wt) and mutant versions were evaluated in the ssOR assay for both strands (LD—the oligonucleotide anneals to the leading strand template; LG—the oligonucleotide anneals to the lagging strand template); and the ssDNA recombination assay using two identical dsDNA substrates except for opposite, asymmetrical phopshothioloate (S) or 5' phosphate (P) as indicated. As can be seen, one strand is favoured over the other in all conditions. In panel C, the results of panel B (preferred strand) were plotted for ssOR (y-axis) and ssDNA (x-axis) to illustrate (i) the E176A mutation is uniformly better than wt in both assays, whereas Q252A, 1 (258A and Q240A are all uniformly worse than wt in both assays (because these data lie on the diagonal through wt); (ii) the E191A, and to a lesser extent, E256A, mutations retain ssOR activity but are selectively impaired for ssDNA recombination. Hence beta recombination is functionally distinguishable from ssOR.

Example 7

Recombination Mediated by Redβ is Greatly Enhanced by Co-Expression of Redγ Whether Redα is Present or not and Redγ Enhances Beta Recombination but not ssOR. Assymetrically Phosphothiolated Substrates Function More Efficiently for Red Mediated Recombination The experiments of FIG. 7 show that ssDNA recombination mediated by Redβ (b) is greatly enhanced by co-expression of Redγ (g), whether Redα (a) is present or not (panels A and C). They also show that assymetrically phosphothiolated dsDNA substrates deliver further enhancements in efficiency for beta recombination (panels A and B). The experiments also show that Redγ (g) has little effect on Red beta mediated ssOR (single stranded oligonucleotide directed mutagenesis; panel D).

FIG. 7 is based on the same assay as described in Example 3 and shown diagrammatically in FIG. 3B. The Red proteins were expressed from pSC101 by the arabinose-inducible promoter, BAD. The assymetrically ended substrates were made with either 5' phosphothioate linkage (S), 5' phosphate (P) or 5' hydroxyl (O) ends as indicated. They were introduced into cells containing Red beta only (b), Red gamma and Red beta (gb) or Red gamma, Red beta and Red alpha (gba).

In the experiment of panel A, the substrates were introduced as double stranded DNA. As can be seen, recombination mediated by Red beta alone is much less efficient than that mediated by Red beta in the presence of either Red gamma or Red gamma and Red alpha. In all three cases, however, strand specific effects were observed with phopsphothiolate protection of the same strand delivering the best results, followed by hydroxy protection of the same strand. Note, panel B shows the same data for Red beta only as does panel A, except with an amplified abcissa.

In the experiment of panel C, only the asymmetrically phosphothioloated/phosphorylated substrates were used, either after predigestion in vitro with Red alpha to create a single stranded substrate (SP-ss or PS-ss), or directly as dsDNA substrates (SP-ds or PS-ds) and results are presented in this order, left to right in the figure according to expression of Red beta only, Red gamma and Red beta, or Red gamma, Red beta and Red alpha. Again the expression of Red gamma delivers a significant benefit. Beyond this benefit, Red alpha expression makes an additional contribution only when dsDNA was used.

Panel D shows the results of an ssOR assay, which demonstrates that Red gamma expression has little effect on oligonucleotide directed mutagenesis. Hence oligonucleotide mutagenesis and beta recombination are mechanistically different.

Example 8

Figure 8A:
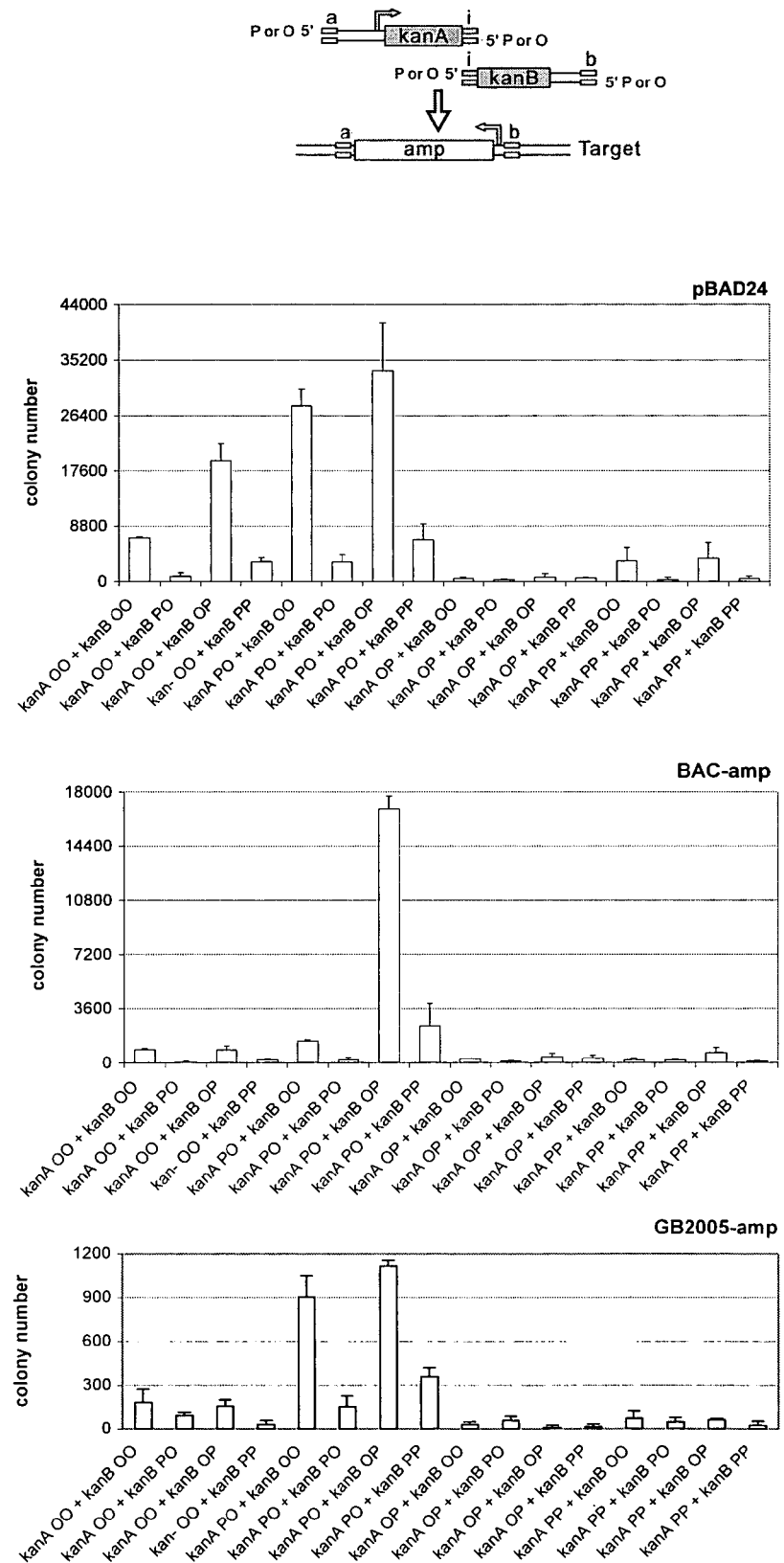
FIG. 8: Applications of asymmetrically phosphorylated substrates to triple and quadruple recombination; panel A relates to the application of asymmetrically phosphorylated substrates to triple recombination; the two substrate DNAs, which are two halves of the gene for kanamycin resistance, are schematically shown at the top of the panel; the target is present either on a high copy plasmid (pBAD24, experimental results shown in the top bar graph), a BAC (BAC-amp, experimental results shown in the middle bar graph) or the *E. coli* chromosome (GB2005-amp, experimental results shown in the lower bar graph); panel B relates to the application of asymmetrically phosphorylated substrates to quadruple recombination and illustrates the same assay as panel A, except that the kanamycin gene was divided into three pieces; panel C relates to the same assay as panels A and B, except that the cassette shared no sequence identity with the target.
Figure 8C:
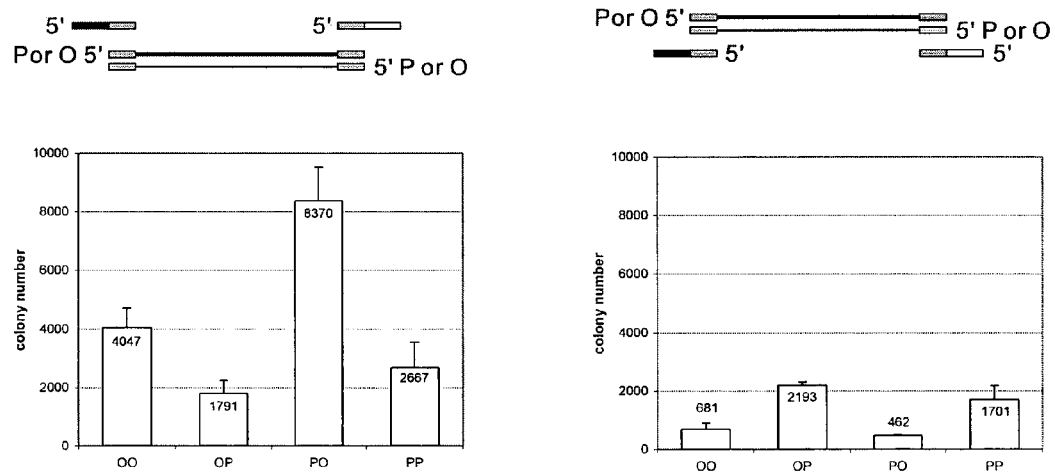

Application of Asymmetrically Phosphorylated Substrates to Triple and Quadruple Recombination The example shown in FIG. 8A relates to the application of asymmetrically phosphorylated substrates to triple recombination. The two substrate DNAs, which are two halves of the gene for kanamycin resistance, are shown at the top. The two substrate DNAs share a region of sequence identity (i) which must recombine to generate kanamycin resistance. They must also recombine into the target through the two regions of sequence identity marked "a" and "b", which replaces a gene on the target encoding ampicillin resistance with the gene for kanamycin resistance. The target is present either on a high copy plasmid (pBAD24, top panel), a BAC (BAC-amp, middle panel) or the E. coli chromosome (GB2005-amp, lower panel). The substrate DNAs were prepared with different combinations of phosphorylated and unphosphorylated ends as shown. The assay was performed in HS996 or GB2005-amp with Red alpha, beta and gamma expressed from a plasmid. The results in FIG. 8A show that the most efficient configuration is the same PO/OP combinations in all cases. Hence a complex task like triple recombination benefits from asymmetrically ended substrates.

In order to investigate the application of asymmetrically phosphorylated substrates to quadruple recombination, the same assay was conducted as described above and shown in FIG. 8B (pBAD24 plasmid target) except that the kanamycin gene was divided into three pieces. The annealing combinations derived from asymmetric substrates were found to work better than any other configuration.

In order to investigate the application of asymmetry for quadruple recombination with a cassette and flanking oligonucleotides, the same assay was applied except that the cassette shared no sequence identity with the target. Rather two oligonucleotides were ordered which contained (i) 50 nucleotides of sequence identity to (a) and (b) flanking the ampicillin gene in the target, shown as black and white regions at the 5' or 3' ends of the two oligonucleotides respectively; and (ii) 40 nucleotides of sequence identity to the cassette, shown as grey regions at the 3' or 5' ends of the two oligonucleotides respectively. The oligonucleotides were both complementary to either one strand or the other (left and right panels respectively). The cassette was either asymmetrically phosphorylated (OP or PO; where O means 5' hydroxylated and P means 5' phosphorylated) or not (OO or PP). As can be seen, one asymmetric configuration is significantly more efficient than any other.

Example 9

Reduced Intramolecular Recombination after Recombineering with Red Beta and Long ssDNAs without Red Alpha In order to investigate the advantages of recombineering with long ssDNAs using Red beta without Red alpha, an assay was conducted in which a hygromycin resistance gene (Hyg) was used as the substrate. The hygromycin gene was either double stranded or was made single stranded by boiling. Hygromycin resistance, which arises from recombination into the target to replace the rpsL counterselectable gene and hence also restore streptomycin resistance, gives a measure of intended recombination. The target BAC DNA contained two half copies of the chloramphenicol resistance gene which share a short region of sequence identity. Recombination between these two short regions will generate chloramphenicol resistance, which gives a measure of unwanted internal recombination. Different combinations of Red proteins were expressed from the pBAD plasmid as indicated in FIG. 9 ((a) pBAD24, no Red protein; (b) pBAD-b, Red beta only; (c) pBAD-a, Red alpha only; (d) pBAD-ba Red beta and alpha; and (e) pBAD-gba, Red gamma, beta and alpha).

The upper table of FIG. 9 shows results from unwanted internal recombination. In all cases, some unwanted recombination was found. As expected, unwanted recombination was greatly stimulated by co-expression of Red alpha and beta, with or without gamma.

The middle panel of FIG. 9 shows colony numbers obtained for the intended recombination. No recombination was obtained without Red beta and numbers obtained by Red beta alone were improved by denaturation. As expected, the most colonies were obtained when Red alpha, beta and gamma were co-expressed using dsDNA substrate. However, this also corresponds with greatly increased levels of unwanted recombination (see upper table of FIG. 9).

The lower table of FIG. 9 was a control for transformation efficiency. Un-induction is a control based on the presence of all aspects except the arabinose induction of the pBAD encoded proteins.

Example 10

Recombination and Electroporation with Freshly Prepared Cells

In this example, the *E. coli* host contains a BAC which conveys chloramphenicol (cm) resistance plus an expression plasmid for the Red proteins, gamma, beta and alpha— pSC101-BAD-gbaA-tet. It conveys tetracycline resistance. The small protocol variation for a high copy plasmid conveying ampicillin (amp) resistance is show in brackets.

1. Incubate the cells in 1.5 ml Eppendorf tubes at 1000 rpm in an Eppendorf thermomixer.
Antibiotic concentrations are given in micrograms per ml.
2. Inoculate a single colony in cm10 (or amp100) plus tet5 in LB at 30° C. for 16 hrs.
3. Inoculate 40 µl of the O/N culture into a 1.4 ml cm 10 (or amp 100) plus tet3 in YenB and incubate at 30° C. for 2 hr.
4. Add 20 µl 10% L-arabinose and grow for 40 min at 37° C.
5. Spin down in an Eppendorf cooling centrifuge at 4° C. at 10,500 rpm for 30 seconds then get rid of the supernatant.
6. Add 1 ml ice chilled 10% glycerol, resuspend by vortexing.
7. Repeat steps 5 and 6 twice.
8. Resuspend in about 30 µl of residual liquid.
9. Add about 200 ng of PCR products purified by column and eluted in double distilled water, leave the yellow tip in the tube.
10. Use the same tip, transfer the cells plus PCR products into ice cooled 1 mm electroporation cuvette, shock in Eppendorf electroporator at 1350 volt.
11. Add 1 ml SOC into the cuvette, pipette up and down two times, transfer it into the Eppendorf tube.
12. Incubate 37° C. for 1 hr.
13. Strike out 100 µl (for HC plasmid) or 1 ml (for BAC, spin down, resuspend to 100 µl) on a selection LB plate. Put into 37° C. incubator for growing O/N to 7 days.

Instead of YenB and SOC, LB may alternatively be used with a workable efficiency.

Example 11

Recombination and Electroporation with Batches of Cells

Recombineering experiments were done in three phases: First, preparation of batches of electrocompetent cells; second, DNA transformation by electroporation, growth recovery and plating on selective agar plates; and third, colony counting and data analysis.

Preparation of Electrocompetent Cell Batches

In order to prepare electrocompetent cells/batches for standard recombineering experiments a 60 ml culture was inoculated from an overnight culture to a starting $OD_{600=0.05}$. In dependence of the expression plasmid origin requirements, the culture was grown either at 30° C. (pSC101 ori) or at 37° C. (pBR322 ori). Protein expression was induced for 45 min at $OD_{600}$=0.2 by L-arabinose (L-ara, f.c.: 0.2%) and growth temperature was either shifted to or maintained at 37° C. upon induction. Cells were harvested, washed twice in ice cold 10% glycerol and the cell density was adjusted to an $OD_{600}$=20 ($1.6*10^7$ cells/µl). Competent cells were either transformed immediately or were quickly frozen in liquid nitrogen and stored at minus 80° C.

DNA Transformation by Electroporation

*E. coli* cells were transformed generally by electroporation. For single electroporations a mixture of $4.8*10^8$ electrocompetent cells and DNA was prepared and subsequently transferred into a single cuvette with 0.1 cm gap width (Molecular BioProducts). The cuvette was placed into an Electroporator 2510 (Eppendorf) and electrically pulsed using a field strength of 12.5 kV/cm (pulse length>5 msec). The cell suspension was flushed out of the cuvette with 970 µl LB-medium. Growth recovery was allowed for 60 min at 37° C. followed by plating on selective agar plates after appropriate dilution.

Colony Counting and Data Normalization

Bacterial colonies grown on agar plates were counted semi-automated using the Molecular Imager Gel Doc XR System (Bio-Rad) in combination with the Colony Counting Quick Guide feature of the Quantity One® 1-D analysis software version 4.6.2 (Bio-Rad). Agar plates were photographed, recorded and detection thresholds as well as the contrast were adjusted to enhance counting accuracy. Optimal counting parameters were set up by comparisons of semi-automated counts to manual counts. The following counting settings were used: was used with the following setting: a) counting sensitivity: 1.0-4.0 and b) average over 3-5 colonies. Since colony sizes varied between individual experiments in dependence of the respective incubation time, the colony size cut-off was adapted to each experiment separately. The counted number of colonies was first normalized to number of colonies per transformation and second either to number of cells, which survived electroporation or to the number of cells, which were transformed with a control plasmid (size<5.0 kb).

Example 12A

Double Recombination by Co-Transformation

Figures 10, 11:
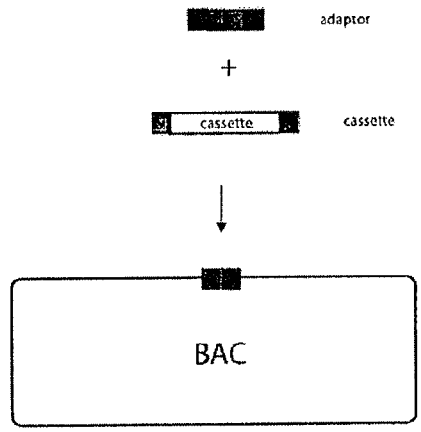
FIG. 10: A preferred sequence of Red beta.
FIG. 11: Double recombination.
Figure 12:
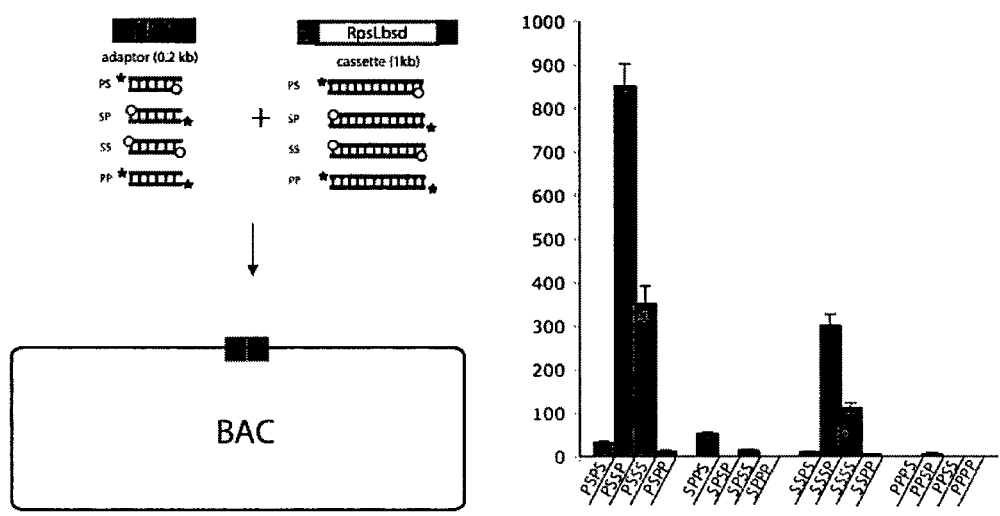
FIG. 12: Double recombination by simultaneous insertion of two single stranded replacement nucleic acids.

FIG. 11 illustrates substrates that may be used in double recombination. In FIG. 12, the use of asymmetrically phosphorylated substrates is shown. Two substrate DNAs (a first double stranded nucleic acid "adaptor" and a second double stranded nucleic acid "cassette") were used to alter the sequence of a target DNA (a BAC) by insertion into the target.

The adaptor had an external pair of arms that were identical to sequences on the target nucleic acid, indicated by the dark rectangles L and R. The adaptor also had an internal pair of arms, indicated by the rectangles S and D, which were identical to sequences flanking the cassette.

An experiment was performed involving the generation of ssDNA intermediates in vivo using asymmetrical modifications at the 5' ends of the substrate dsDNAs. On the left hand side of FIG. 12, the double recombination substrates and reactions are schematically presented. The adaptor was 200 bps long and made from synthetic oligonucleotides that had been stitched together in a PCR reaction. Four variations of the adaptor were made corresponding to 5' phosphorylation (P) or terminal phosphothioate bonds (S) at the either end. Similarly, four variations of the cassette were made corresponding to 5' phosphorylation (P) or terminal phosphothioate bonds (S) at the either end. The four version of the adaptor were individually combined with each of the four versions of the cassette to generate the 16 combinations shown in FIG. 12, and co-transformed in cells expressing the Red system and containing the BAC.

The results are presented in the histogram of FIG. 12. On the x-axis, the first two letters (either P or S) refer to the adaptor and the second two refer to the cassette. the ordinate shows the relative homologous recombination efficiency. These results show that (i) the double recombination reaction proceeded through single stranded intermediates; and (ii) there was a very large difference between the optimum configuration of asymmetries on the substrate dsDNAs (PSSP), which promoted the best ssDNA intermediates, and the symmetrical configurations. This was especially true for the PPPP configuration, which is the normal state of restriction digested dsDNA.

Figure 13:
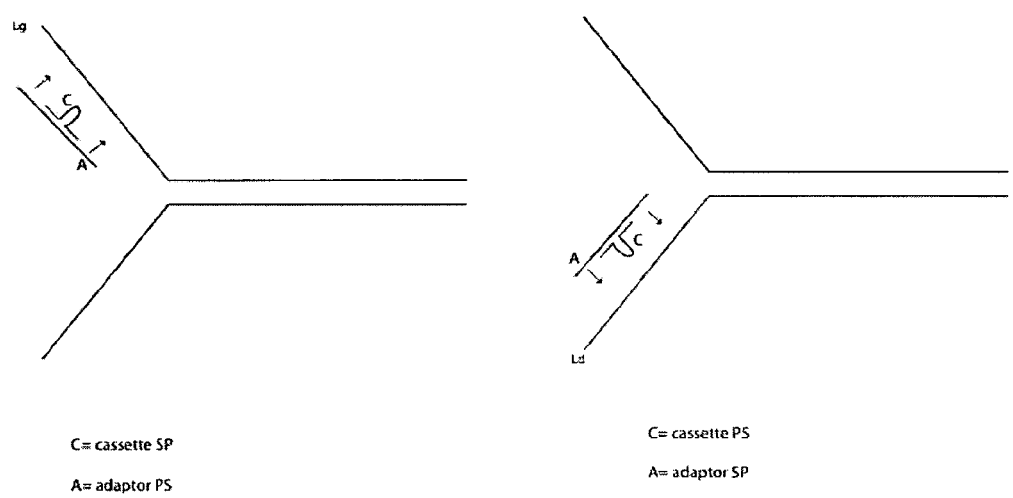
FIG. 13: Possible mechanism for double recombination by simultaneous insertion of two single stranded replacement nucleic acids.

FIG. 13 proposes a model for this double recombination reaction. The recombination substrates are converted into ssDNA intermediates, which anneal to the replication fork as illustrated. The most efficient outcome is achieved when the adaptor ssDNA intermediate anneals to the lagging strand of the target DNA at the replication fork. This situation is illustrated on the left of FIG. 13 and is thought to correspond to the PSSP experiment in FIG. 12. The less efficient situation in which the adaptor ssDNA intermediate anneals to the leading strand of the target DNA is shown on the right; this situation is thought to correspond to the SPPS experiment in FIG. 12.

Example 12B

Double Recombination by Sequential Transformation

Double recombination can also be achieved in two steps of consecutive transformation whereby the first introduced double stranded nucleic acid is the adaptor and the second double stranded nucleic acid is the cassette. An adaptor was made by PCR containing a selectable marker between the internal pairs of arms. The selectable marker was an antibiotic resistance marker. In the first step of recombination, the adaptor was transformed in cells expressing the Red system and containing the target nucleic acid, such that the adaptor inserted into the target BAC. Insertion was selected for by the expression of the selectable marker. In the second recombination step, the cassette was inserted into the target nucleic acid using the internal arms of the adaptor inserted during the first recombination step.

Figure 14:
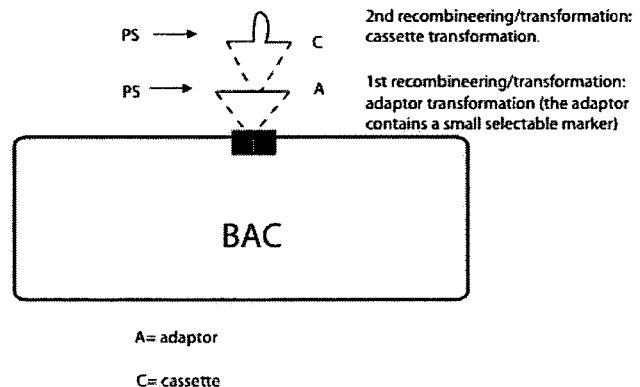
FIG. 14: Double recombination by sequential insertion of two single stranded replacement nucleic acids.

FIG. 14 proposes a model for this two-step double recombination reaction. In the first step, the adaptor is inserted. In the second, the cassette is inserted into the target via the internal arms of the adaptor. In both steps, the most efficient recombination intermediate is the ssDNA strand that can anneal to the lagging strand of the target molecule. Here, the preferred combination of asymmetries on the adaptor and cassette is different from the co-transformation double recombination discussed in Example 12A. PSPS (or POPO, PSPO or POPS) is the most efficient because it results in the ssDNA strand annealing to the lagging strand during both steps.

(Synthetic) Example 13

Preparation of Adaptor and Cassette Fragments

The double stranded nucleic acid adaptor used in examples 12A and 12B was generally made using synthetic oligonucleotides with the relevant asymmetries (preferably P and S). These synthetic oligonucleotides were used as primers in a PCR reaction and the PCR product was used directly for recombination.

The preparation of the double stranded nucleic acid cassette was more complicated because it was often too long for PCR amplification, or the mutagenic risk of PCR amplification had to be avoided. Consequently it was usually not possible to attach the 5' asymmetries to the cassette using synthetic oligonucleotides and PCR. In this case, the cassette was cut with an enzyme that cleaved at one end only. The cassette was then subjected to treatment with a phosphatase enzyme such that the exposed 5' phosphates groups were removed. Following this step, the other end of the cassette was cleaved with a different restriction enzyme to expose a 5' phosphate group. This generated an asymmetric PO or OP cassette.

Example 14

Recombination of Mouse ES Cells

Generation of a Double Stranded Nucleic Acid Substrates by Long Range PCR

Figure 15:
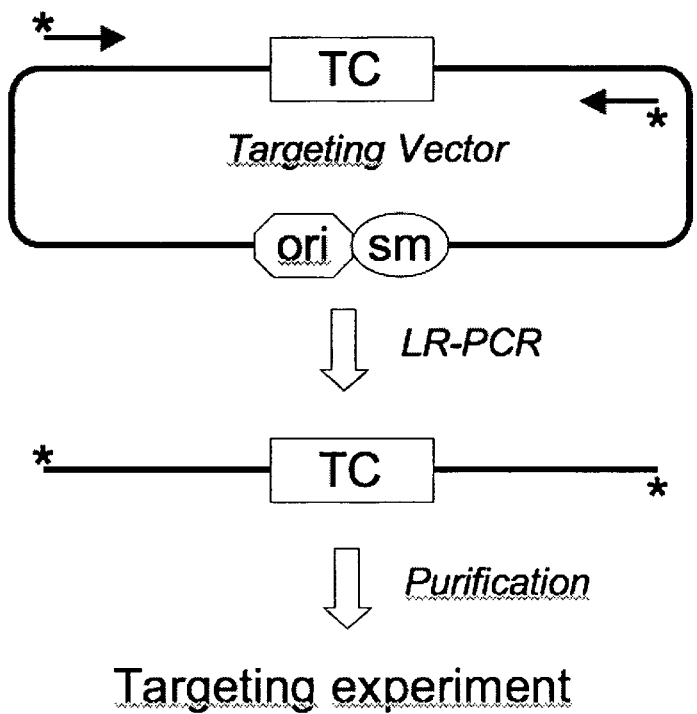
FIG. 15: Generation of double stranded nucleic acid substrates by long range PCR.
Figure 16:
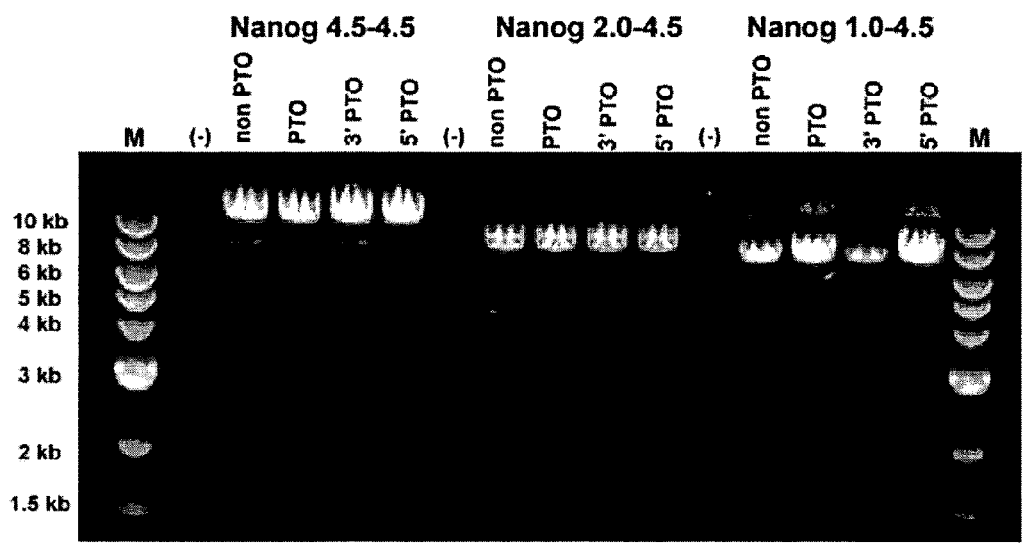
FIG. 16: Double stranded nucleic acid substrates with differently deployed phosphothioates.

A double stranded nucleic acid substrate for use in the invention may be generated by long range PCR, e.g. of a targeting construct (TC) in a plasmid or episome (FIG. 15). A series of substrates were generated in this way using a long range PCR kit (Roche) and synthetic oligonucleotides which carried modified 5' ends. The Nanog gene, present in a plasmid, was amplified using different oligonucleotides carrying two phosphothioate (PTO) bonds at their 5' ends or not, as indicated in FIG. 16. In this way, the resulting substrates included differently deployed phosphothioates at their 5' ends. The oligonucleotides primed the Nanog DNA sequences either side of a central selectable "cassette" to produce a 5' homology arm of 4.5, 2.0 and 1.0 kbs (as indicated in FIG. 15), and a 3' homology arm of 4.5 kb in all cases.

Recombination

Figure 17:
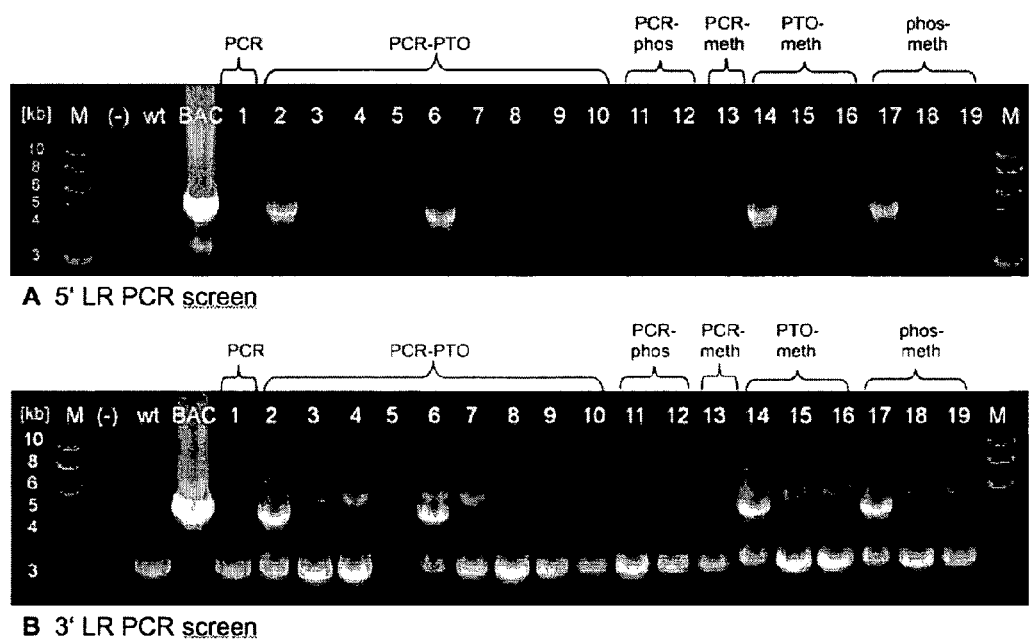
FIG. 17: Successful recombination using phosphothioated substrates; panel A relates to a 5' long range (LR) PCR screen; panel B relates to a 3' LR PCR screen.

Successful recombination using the double stranded nucleic acid substrate is shown in FIG. 17. Recombination was carried out using mouse ES cells according to standard procedures. Candidate colonies were screened by long rang PCR to distinguish between homologous recombinants and random integrations. FIG. 17 shows that colonies 2, 6, 14 and 17 resulted from correct recombination events at both 5' and 3' sides.

Accordingly, phosphothioated substrates generated by long range PCR are functional in a mammalian system. The phosphothioated substrates were more efficient than their unphosphothioated counterparts.

Example 15

Figure 18:
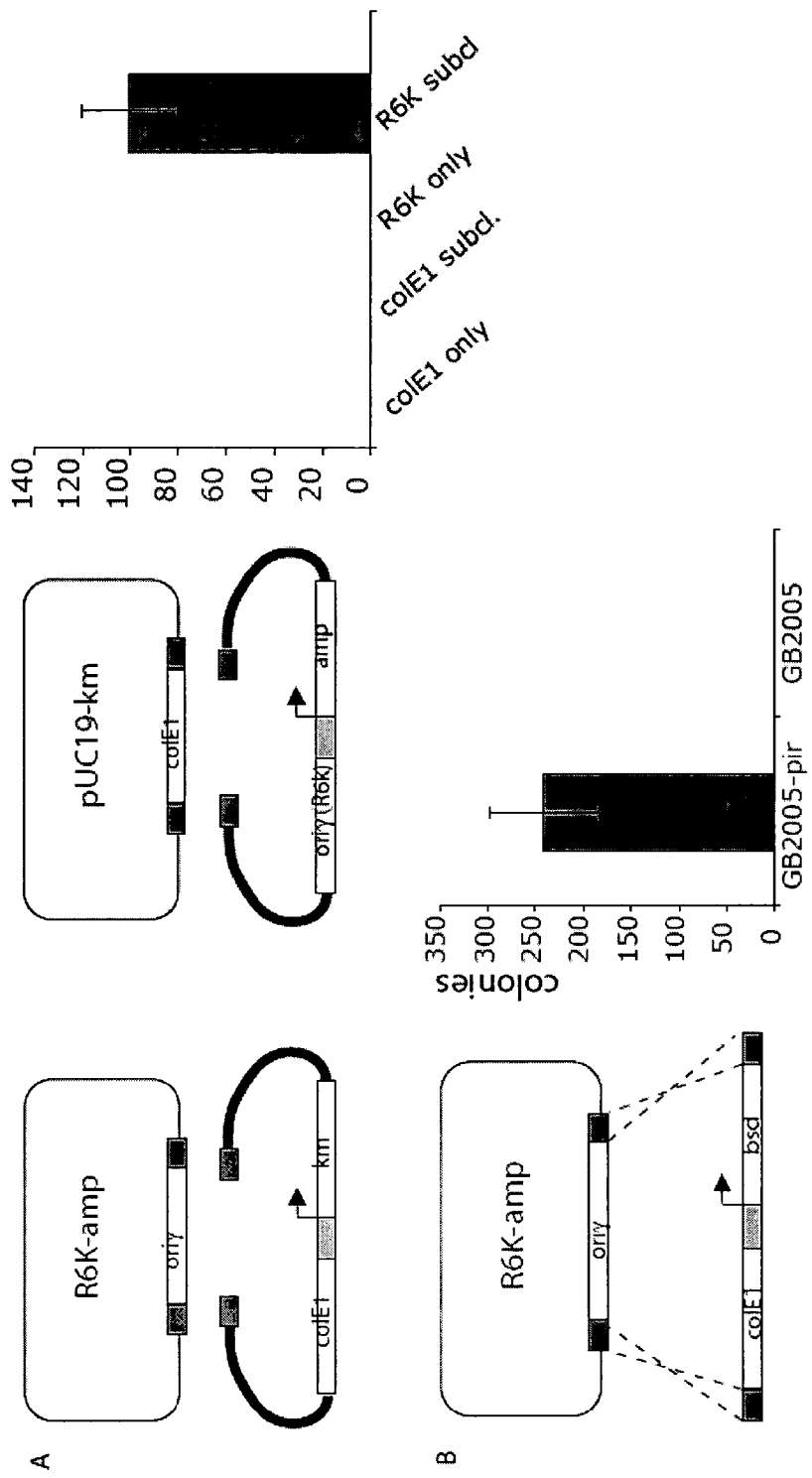
FIG. 18: Recombination with a replicating substrate; panel A illustrated an experiment in which an attempt was made to subclone a replication origin, either the on gamma of R6K plasmid or colE1 of a standard pUC plasmid into the converse vector by gap repair; panel B illustrates an experiment, in which an R6K plasmid, which requires the Pir protein to replicate, as well as a linear DNA fragment which included a colE1 origin and the blasticidin resistance gene were used.
Figure 24:
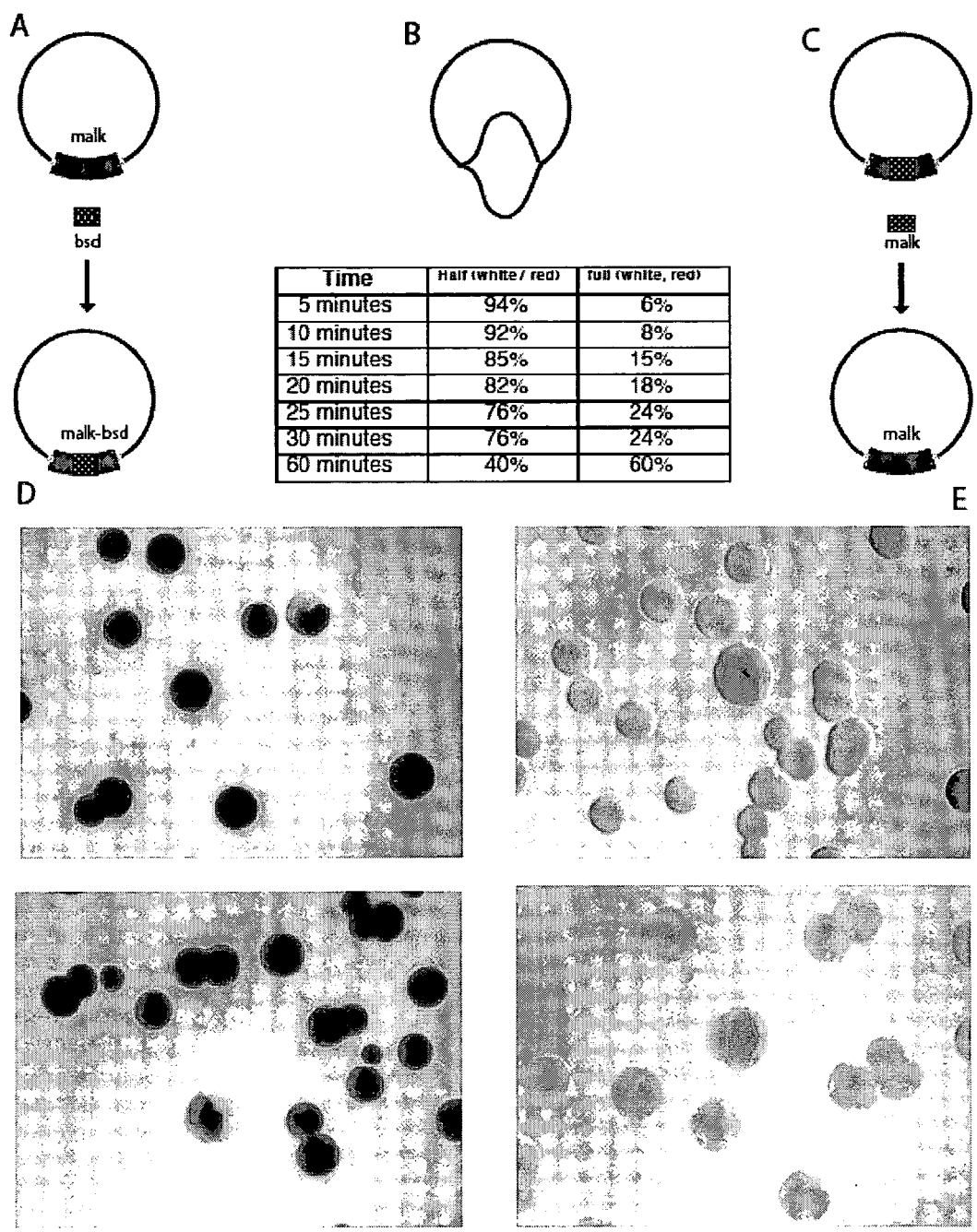
FIG. 24: Evidence in favour of a heteroduplex recombination intermediate; a schematic representation of an assay to mutate and restore the malK gene is shown in panels A and C, respectively; panel B top shows a schematic representation of the heteroduplex model in which the recombination intermediate includes both the parental region at the site of recombination as well as the new mutant strand; an in situ recombination assay based on colony colour was performed, with the results shown in panel B bottom; panels D and E show cells plated out at single cell dilution and cultured until the colony colour was apparent.

Further Evidence for a Single Stranded Intermediate in Homologous Recombination Reactions All recombination experiments described in FIG. 18 employed linear substrates that included 50 nt/bp continuous identity to the target at each end (the 'homology arms'), flanking a gene encoding resistance to an antibiotic (except for the experiment of FIG. 24C). Hence recombination was readily scored as colonies that acquired resistance to the corresponding antibiotic. The recombination reactions were carried out with our standard protocol (described supra), which has been optimized for convenience and productivity.

Replication is Required for Red Recombination with dsDNA Substrates

The experiments shown in FIG. 18 were performed to evaluate whether dsDNA recombination mediated by Red alpha and Red beta depends upon replication. In the first variation, an attempt was made to subclone a replication origin, either the on gamma of R6K plasmid or colE1 of a standard pUC plasmid into the converse vector by gap repair. As expected, neither linear vector alone produced any colonies (FIG. 18A, colE1 only, R6K only). The only productive recombination event to generate resistant colonies occurred when the intact plasmid was replicating. In the cells used in this experiment, the colE1 plasmid replicated but the R6K plasmid did not (because the Pir protein, which is essential for R6K replication was not supplied). This result indicates that the target plasmid must be replicating to permit productive recombination.

In a second test, an R6K plasmid, which requires the Pir protein to replicate, as well as a linear DNA fragment which included a colE1 origin and the blasticidin resistance gene were used. In this test, the homology arms were chosen so that recombination would replace the R6K origin with the colE1 origin. Thereby the recombination product would have an operational replication origin. The two DNAs were co-electroporated into an *E. coli* strain that contained Red alpha, beta and gamma with or without Pir. Recombination only occurred in the presence of Pir, demonstrating a need for replication of the R6K plasmid before recombination.

Rethinking the dsDNA Intermediate in Red Recombination

Figure 19:
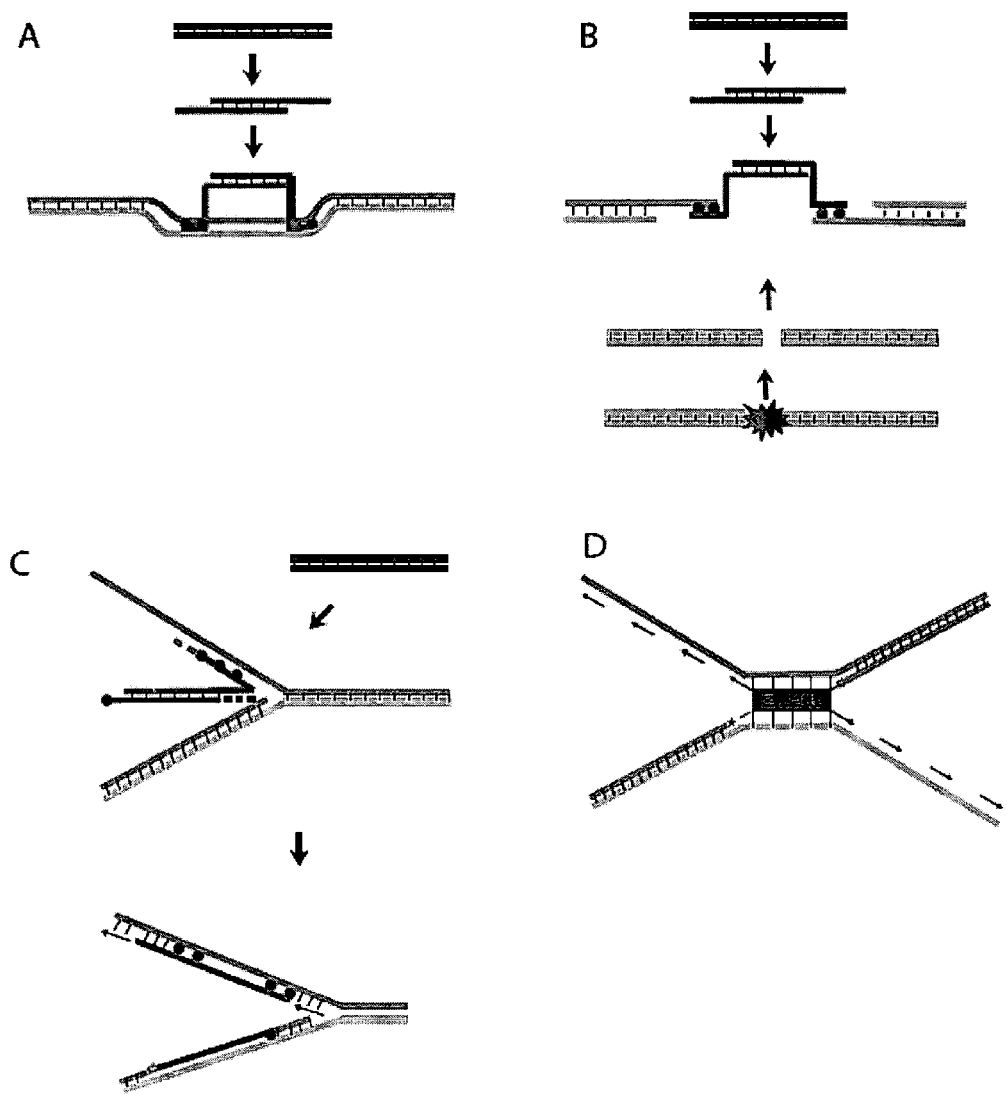
FIG. 19: Proposed recombination models based on a linear dsDNA substrate; panel A illustrates a strand invasion intermediate; panel B illustrates an annealing intermediate; panel C illustrates a chicken-foot intermediate and panel D illustrates a double replication fork intermediate.

Previous ideas about Red recombination with dsDNA substrates have assumed that the reaction initiates with action by the exonuclease, Red alpha, to resect the dsDNA ends and create a symmetrically resected, ssDNA/dsDNA intermediate (as illustrated in FIG. 19A) that then hybridizes to form some kind of joint molecule. Four types of joint molecule intermediates have been proposed (Muyrers et al, 2000; Court et al, 2002), as illustrated in FIG. 19, including (A) a strand invasion intermediate; (B) an annealing intermediate; (C) a chicken-foot intermediate and (D) a double replication fork intermediate. Each of these propositions has certain weaknesses, including (A) single strand annealing proteins (SSAPs) like Red beta do not appear to possess strand invasion activity (Kuzminov, 1999); (B) a fortuitous double strand break is required close to the recombination site; (C) a chicken foot intermediate does not explain the efficiencies of very large deletions achievable by Red recombination; (D) the proposed double replication fork is hypothetical and has never been documented.

In contrast to the assumption that Red recombination is initiated by symmetrical resection of the linear dsDNA substrate, evidence is presented herein that the intermediate is full length ssDNA.

Figure 20:
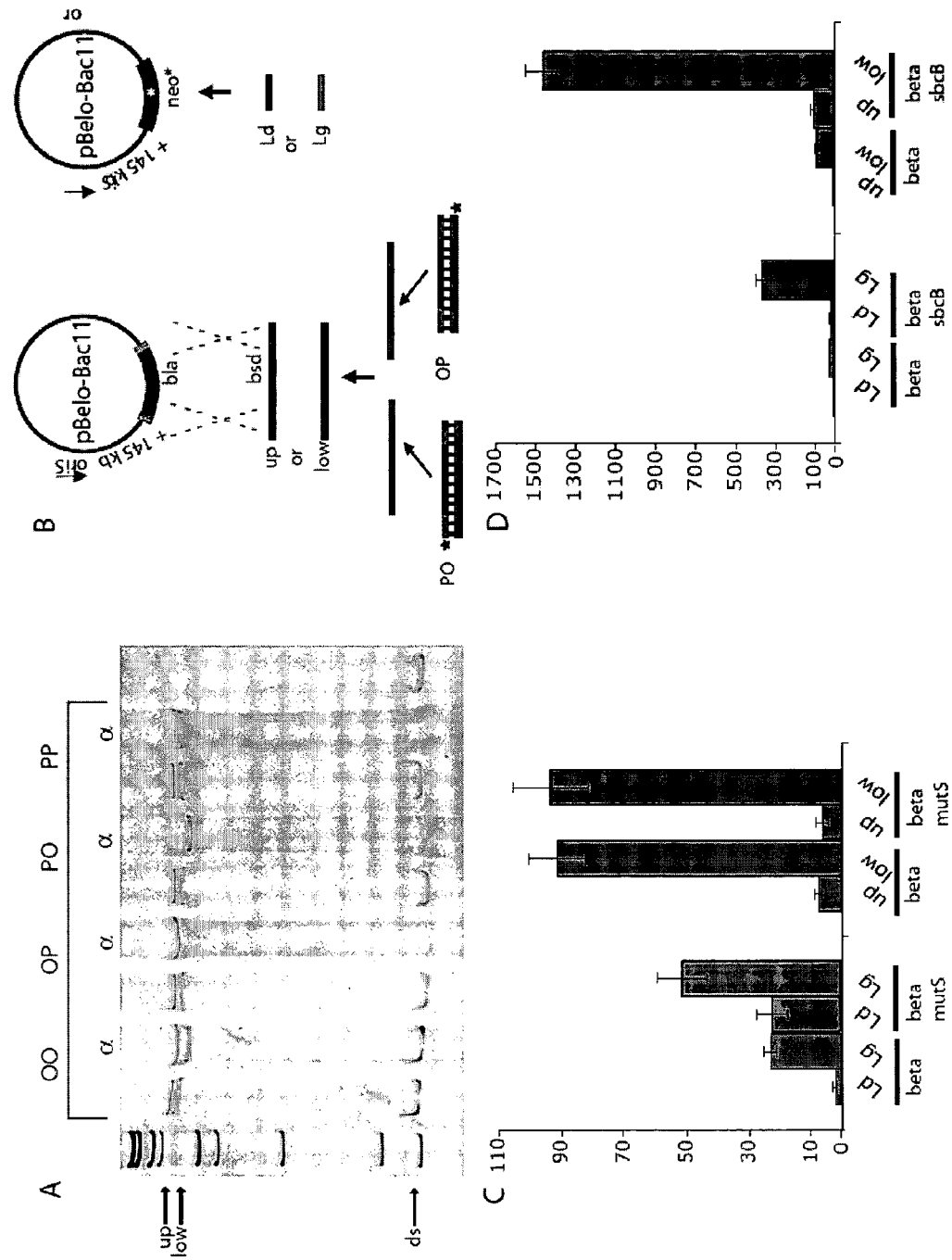
FIG. 20: Recombination and oligonucleotide mediated repair with ssDNA; a dsDNA substrate was prepared carrying either phosphorylated (P) or hydroxylated (O) 5' ends in all four combinations (OO, OP, PO, PP); these substrates were digested with Red alpha in vitro and the products analyzed by SSCP (single strand conformation polyacrylamide gel electrophoresis), the results of which are shown in panel A; the OP and PO ssDNA products were used in a recombination reaction to insert the blasticidin (bsd) resistance gene into a BAC, as schematically illustrated in panel B; in parallel, a recombination reaction with single stranded oligonucleotides, to repair a mutation in the neomycin (neo) resistance gene and so restore kanamycin resistance was performed, as a positive control; the results of the recombination reactions are illustrated by the bar graph shown in panel C; the same experiment as in panel C was carried out but using a sbcB mutation instead of a mutS mutation and the results are illustrated by the bar graph shown in panel D.

To test this idea, the fact that Red alpha prefers to begin exonuclease activity on a 5' phosphorylated rather than hydroxylated (dephosphorylated) end was exploited. Consequently, a dsDNA substrate was prepared carrying either phosphorylated (P) or hydroxylated (O) 5' ends in all four combinations (OO, OP, PO, PP) as illustrated in FIG. 3. These substrates were digested with Red alpha in vitro and the products analyzed by SSCP (single strand conformation polyacrylamide gel electrophoresis). As can be seen in FIG. 20A, Red alpha digested only the phosphorylated strand in the OP and PO substrates, whereas the OO substrate was not digested on either strand and the PP substrate was digested on both, producing some smaller ssDNA products.

Consequently, the OP and PO ssDNA products were used in a recombination reaction to insert the blasticidin (bsd) resistance gene into a BAC (FIG. 20B). Because Red alpha is not required for Red beta mediated recombination with single stranded oligonucleotides (Zhang et al, 2003), the cells harbouring the BAC contained only expressed Red beta. In parallel, a recombination reaction with single stranded oligonucleotides, to repair a mutation in the neomycin (neo) resistance gene and so restore kanamycin resistance was performed, as a positive control. As expected from previous observations, the oligonucleotide that served as a primer for lagging strand synthesis (Lg) produced more recombinants than the complementary oligo (Ld) (FIG. 20C). The same effect was observed with the ssDNA substrates. That is, the ssDNA that could hybridize with the lagging strand template to prime lagging strand synthesis (low) delivered many more recombinants than the complementary strand. Notably, the two assays could be distinguished by mutations in the mismatch repair pathway (mutS), indicating the two reactions were not identical. As shown before (Court, Hong Kong), mutations in the mismatch repair pathway enhanced oligonucleotide directed mutagenesis and the enhancement was greater for the leading strand oligo (Ld). However, no mutS effect on ssDNA recombination was found (FIG. 20C). Conversely, an sbcB mutation significantly enhanced both oligonucleotide and ssDNA directed recombination.

Testing the ssDNA Intermediate In Vivo

To determine whether dsDNA recombination can be processed through a full length ssDNA intermediate in vivo, the four linear dsDNA substrates (OO, OP, PO, PP) were employed in a recombination assay in the presence of Red alpha (and Red gamma) as well as Red beta. The purpose of this experiment was to test if Red alpha could asymmetrically degrade the substrates and what effect this may have on recombination efficiencies. The experimental design is shown in FIG. 21A. Recombination was directed to either a BAC or the *E. coli* chromosome. In both cases, the target was established in both orientations (bla and inv-bla), which alters the recombination reaction with respect to the origin of replication. Using an asymmetric substrate (OP), SSCP revealed that Red alpha rapidly generated the ssDNA intermediate in vivo (FIG. 21B). Recombination was most efficient with the asymmetrically phosphorylated substrate whose hydroxylated 5' strand could prime lagging strand synthesis, henceforth referred to as the 'lagging strand primer'. Inverting the target inverted the strand preference, demonstrating that the PO and OP substrates were both proficient. The same conclusions could be drawn from both the BAC and chromosomal assays (FIG. 21C,D). Notably, the next best substrate in all configurations was the doubly hydroxylated one (OO) and in this case inverting the target had no effect.

To challenge these findings in an additional way, substrates with phosphothioated bonds at the 5' ends were made. Previously it has been reported that phosphothioated bonds have no beneficial effect for Red recombination. However this study employed five consecutive phosphothioated bonds at the 5' end. This issue was examined using an oligonucleotide assay and found that two consecutive phosphothioate bonds are optimally beneficial (not shown). Hence the experiment of FIG. 21E employed this configuration to generate substrate variations combining phosphothioate (S) with phosphorylated (P) and hydroxylated (O) 5' ends. Notably the asymmetrically phosphothioated/phosphorylated (SP, PS) substrates were more efficient than the hydroxylated/phosphorylated (OP, PO) substrates (compare D and E). Again, the most efficient SP orientation had the phosphothioate at the 5' end of the lagging strand primer. Furthermore permutations of S and O, like the OO substrate, delivered reasonable recombination efficiencies. The SO substrates displayed a limited strand preference, whereas the SS substrate showed none. All of these results are consistent with the following conclusions; (i) a pair of phosphothioates or a hydroxylation enhanced recombination when placed at the 5' end of the lagging strand primer; (ii) this enhancement was amplified when the 5' end of the other strand was phosphorylated, presumably because the phosphorylated strand was rapidly degraded by Red alpha producing full length single stranded, lagging strand primer; (iii) when both 5' ends were completely blocked to the exonculease, another activity such as a helicase must separate the strands so that the full length lagging strand primer can initiate recombination.

Figure 21:
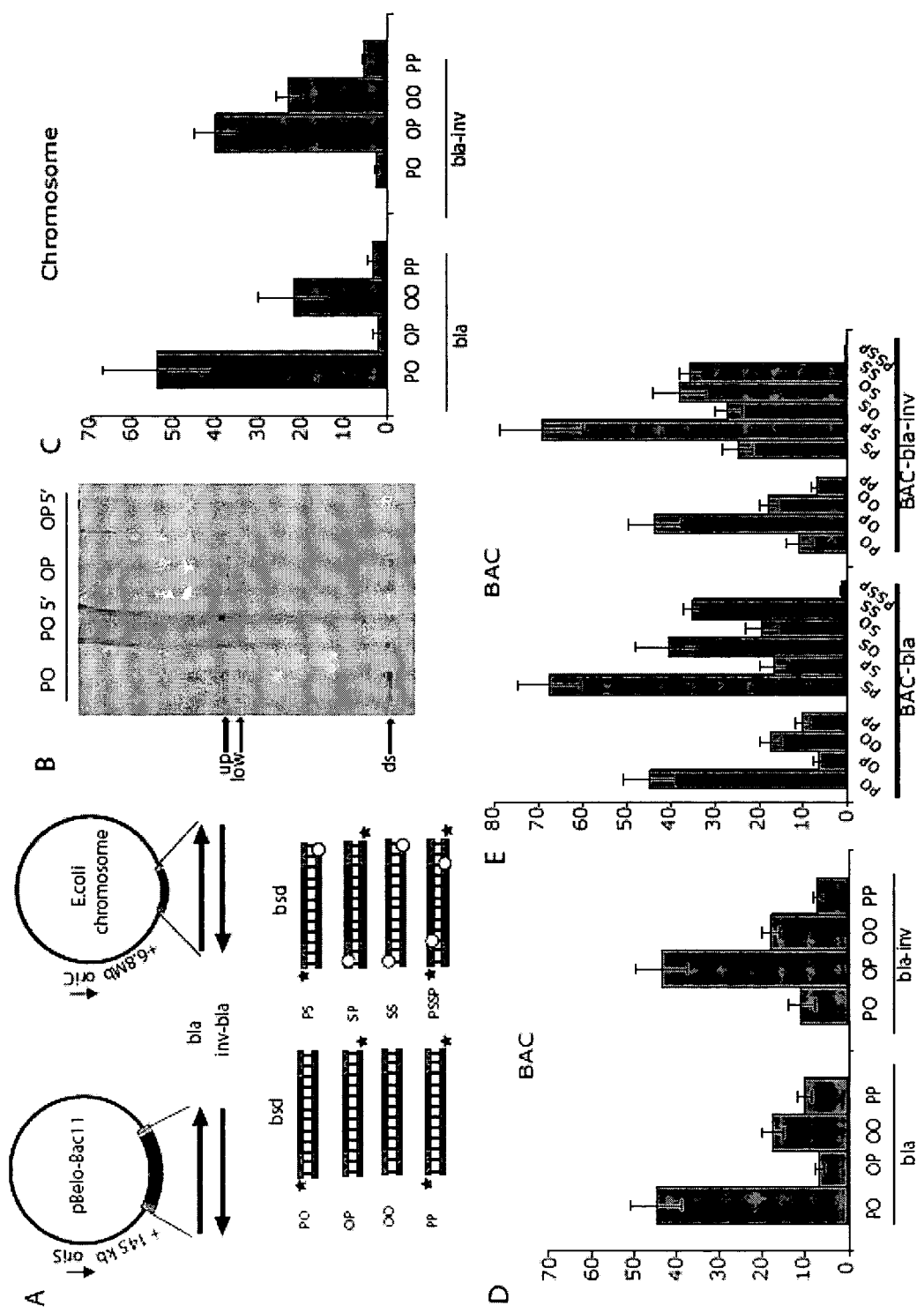
FIG. 21: Effect of modifications at 5' ends on recombination efficiencies; the experimental design is shown in panel A; recombination was directed to either a BAC or the *E. coli* chromosome; in both cases, the target was established in both orientations (bla and inv-bla), which alters the recombination reaction with respect to the origin of replication; using an asymmetric substrate (OP), SSCP revealed that Red alpha rapidly generated the ssDNA intermediate in vivo, as illustrated by panel B; the results of BAC and chromosomal assays are illustrated by the bar graphs shown in panels C and D; panel E shows a bar graph illustrating the experimental results with substrate variations combining phosphothioate (S) with phosphorylated (P) and hydroxylated (O) 5' ends.
Figure 22:
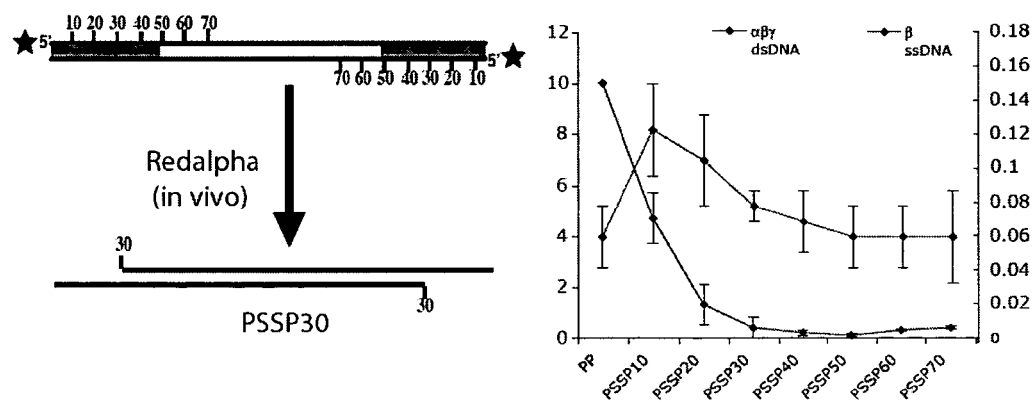
FIG. 22: Evidence against a symmetrically resected dsDNA intermediate in recombination.

As a further test, an experiment to evaluate the recombination efficiencies of symmetrically resected dsDNA intermediates was designed. This experiment relied on the observations that phosphothioates block Red alpha exonuclease activity but are permissive for recombination (FIG. 21). A pair of phosphothioates were symmetrically placed at increasing distances from the 5' ends of a substrate as illustrated in FIG. 22. That is, the phosphothioates were either 10, 20, 30, 40, 50, 60 or 70 nucleotides from each 5' end. Both 5' ends were phosphorylated to promote Red alpha exonuclease activity. It was reasoned that Red alpha would resect both ends until reaching the phosphothioate bonds, thereby generating the symmetrically resected substrates that were previously believed to be the optimal recombination intermediates. By this previous logic, the series of phosphothiolated substrates up to 70 was chosen to include the presumptive best intermediates that have both homology arms exposed as ssDNA and the region in between as double stranded. However, it was found that these substrates were very inefficient (FIG. 22B), particularly when compared to the SS substrate (FIG. 21E). To control for the quality of the substrates, they were boiled to separate the strands and used in a recombination assay mediated by Red beta only. Although this Red beta-only recombination reaction was very inefficient, all of the internally phosphothioated substrates were equivalent for recombination after boiling.

Figure 23:
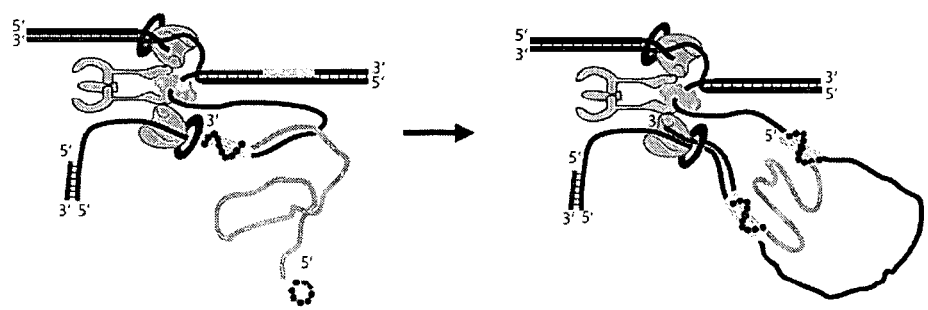
FIG. 23: Proposed model for single stranded DNA intermediates in recombination.

Taken together, this evidence supports a new model for homologous recombination mediated through a single strand that forms a heteroduplex at the replication fork, as illustrated in FIG. 23.

This heteroduplex model predicts that the recombination intermediate includes both the parental region at the site of recombination as well as the new mutant strand. If the heteroduplex gets replicated, the product should be one daughter that is parental and one that is mutant. To look for this possibility, an in situ recombination assay based on colony colour was developed. Parental cells carrying the intact malK gene give a red colour whereas mutants for malK are white. The assay was performed in two directions, one to mutate the malK gene and the other to restore it. After incubation to permit recombination, cells were plated out at single cell dilution and cultured until the colony colour was apparent. Because an *E. coli* cell can harbour two copies of any gene (after it has been replicated, before cell division), these experiments were performed as a time course of recombination. As presented in FIG. 24B, almost all recombination events at the earliest time point resulted in two-colour colonies, indicating that the cell in which the recombination occurred harboured a heteroduplex as predicted.

In conclusion, a novel homologous recombination pathway via an intermediate that includes only one strand invading the replication fork to form a heteroduplex that appears to be insensitive to the mismatch repair pathway is described in this example. This new pathway is therefore distinct from previous descriptions of oligonucleotide-directed mutagenesis, which can introduce small mutations, whereas the recombination reaction discussed here can support large mutagenesis. The evidence for the novelty of this mechanism and differences from oligonucleotide directed mutagenesis recapitulates, complements and extends the evidence presented in FIGS. 3 to 7.

REFERENCES

Muyrers, J. P. P., Zhang, Y., Buchholz, F. and Stewart, A. F. (2000) RecE/RecT and Reda/Redb initiate double stranded break repair by specifically interacting with their respective partners Genes and Development, 14, 1971-1982.

Zhang, Y., Muyrers, J. P. P., Rientjes, J. and Stewart, A. F. (2003) Phage annealing proteins promote oligonucleotide-directed mutagenesis in *E. coli* and mouse ES cells BMC Mol Biol, 4 (1) 1.

Kuzminov A (1999) Microbiol Mol Biol Rev. 63:751-81-3

Court D L, Sawitzke J A, Thomason L C. (2002) Genetic engineering using homologous recombination. Annu Rev Genet. 36:361-88.

It will be evident that the above examples are purely illustrative of the invention and that modification in detail can be made within the scope of the invention.

The invention claimed is:

1. A method for inserting a single stranded replacement nucleic acid intermediate produced from a double stranded nucleic acid substrate into a target nucleic acid, said method comprising the steps of:
   a) generating a single stranded replacement nucleic acid intermediate from a double stranded nucleic acid substrate, wherein the double stranded nucleic acid substrate is adapted at one or both of its 5' ends such that preferential degradation of one strand and/or strand separation generates the single stranded replacement nucleic acid intermediate, wherein the single stranded replacement nucleic acid intermediate comprises a 5' region that is identical to sequence on the target nucleic acid, a 3' region that is identical to sequence on the target nucleic acid and optionally a replacement region between the 5' and 3' regions that is not identical to sequence on the target nucleic acid,
   b) exposing the target nucleic acid to the single stranded replacement nucleic acid intermediate under conditions suitable for recombination to occur between the single stranded replacement nucleic acid intermediate and the target nucleic acid, and
   c) selecting a target nucleic acid whose sequence has been altered by inclusion of said single stranded replacement nucleic acid intermediate;
wherein steps (a) and (b) take place within the same recombination reaction; wherein steps (a) and (b) are carried out in the presence of Red beta; wherein the Red beta comprises an amino acid sequence that is at least 95% identical to the sequence of SEQ ID NO: 2 and is capable of mediating recombination between the single stranded replacement nucleic acid intermediate and the target nucleic acid; and wherein the double stranded nucleic acid substrate is adapted so that it is asymmetric at its 5' ends, wherein the asymmetry causes one strand to be preferentially degraded.

2. The method of claim 1, wherein the asymmetry of the double stranded nucleic acid substrate is conferred by a modification that affects the progression of a 5'-3' exonuclease on one strand but does not affect the progression of the 5'-3' exonuclease on the other strand.

3. The method of claim 1, wherein the asymmetry of the double stranded nucleic acid substrate is conferred by a modification that prevents a 5'-3' exonuclease binding to one strand but does not affect the 5'-3' exonuclease binding to the other strand.

4. The method of claim 1, wherein the asymmetry of the double stranded nucleic acid substrate is a covalent modification that is present at or in close proximity to the 5' end of one strand but is not present at or in close proximity to the 5' end of the other strand.

5. The method of claim 4, wherein the covalent modification is selected from the group consisting of a phosphothioate bond, a phosphoacetate bond, a locked nucleotide, a hydroxyl group and a 5' protruding end.

6. The method of claim 4, wherein the covalent modification is selected from the group consisting of a 5' phosphate group, a flush or recessed 5' end, a 5' end that carries a stretch of DNA sequence that is not identical to the target DNA, or a 5' end that includes deoxy uridine nucleotides in place of deoxy thymidine nucleotides in the DNA strand.

7. The method of claim 1, wherein one strand of the double stranded nucleic acid substrate is adapted at its 5' end to comprise a covalent modification selected from the group consisting of a phosphothioate bond, a phosphoacetate bond, a locked nucleotide, a hydroxyl group and a 5' protruding end; and wherein the other strand is adapted at its 5' end to comprise a covalent modification selected from the group consisting of a 5' phosphate group, a flush or recessed 5' end, a 5' end that carries a stretch of DNA sequence that is not identical to the target DNA, or a 5' end that includes deoxy uridine nucleotides in place of deoxy thymidine nucleotides in the DNA strand.

8. The method of claim 4, wherein one strand of the double stranded nucleic acid substrate is adapted to comprise a Red alpha exonuclease pause sequence or a cos site at or in close proximity to the 5' end of one strand but not at or in close proximity to the 5' end of the other strand.

9. The method of claim 1, wherein steps (a) and (b) are carried out in the presence of Red beta and Red alpha.

10. The method of claim 1, wherein steps (a) and (b) are carried out in the presence of Red beta and in the presence of Red gamma and in the absence of Red alpha.

11. The method of claim 1, wherein steps (a) and (b) are carried out in the presence of Red beta, Red gamma and Red alpha.

12. The method of claim 1, wherein the double stranded nucleic acid substrate is adapted to comprise a covalent modification at both of its 5' ends.

13. The method of claim 12, wherein the covalent modification is the presence of a biotin molecule or a phosphothioate.

14. The method of claim 12, wherein steps (a) and (b) are carried out in the presence of Red beta and a helicase.

15. The method of claim 1, wherein the method comprises making the double stranded nucleic acid substrate from two or more double stranded nucleic acids or from one or more double stranded nucleic acids together with one or more single stranded oligonucleotides.

16. The method of claim 1, wherein the single stranded replacement nucleic acid intermediate in steps a)-c) is a first single stranded replacement nucleic acid intermediate as defined in step a), specifically comprising a replacement region between the 5' and 3' regions, and the method comprises additional steps d)-f):
- d) generating a second single stranded replacement nucleic acid intermediate from a second double stranded nucleic acid substrate, wherein the second double stranded nucleic acid substrate is adapted at one or both of its 5' ends such that preferential degradation of one strand and/or strand separation generates the second single stranded replacement nucleic acid intermediate, wherein the second single stranded replacement nucleic acid intermediate comprises:
  - i) either a 5' region that is identical to a first sequence on the replacement region of the first single stranded replacement nucleic acid intermediate and a 3' region that is identical to a second sequence on the replacement region of the first single stranded replacement nucleic acid intermediate, or a 5' region that is complementary to a first sequence on the replacement region of the first single stranded replacement nucleic acid intermediate and a 3' region that is complementary to a second sequence on the replacement region of the first single stranded replacement nucleic acid intermediate; and
  - ii) optionally a replacement region between the 5' and 3' regions that is not identical to sequence on the target nucleic acid,
- e) exposing the selected target nucleic acid of step c) to the second single stranded replacement nucleic acid intermediate under conditions suitable for recombination to occur between the second single stranded replacement nucleic acid intermediate and the selected target nucleic acid, wherein steps (d) and (e) are carried out in the presence of Red beta; wherein the Red beta comprises an amino acid sequence that is at least 95% identical to the sequence of SEQ ID NO: 2 and is capable of mediating recombination between the second single stranded replacement nucleic acid intermediate and the selected target nucleic acid, and
- f) selecting a target nucleic acid whose sequence has been altered by inclusion of said second single stranded replacement nucleic acid intermediate.

17. The method of claim 1, wherein steps a)-c) are:
- a) generating
  - i) a first single stranded replacement nucleic acid intermediate from a first double stranded nucleic acid substrate, wherein the first double stranded nucleic acid substrate is adapted at one or both of its 5' ends such that preferential degradation of one strand and/or strand separation generates the first single stranded replacement nucleic acid intermediate, wherein the first single stranded replacement nucleic acid intermediate comprises a 5' region that is identical to sequence on the target nucleic acid, a 3' region that is identical to sequence on the target nucleic acid and a replacement region between the 5' and 3' regions that is not identical to sequence on the target nucleic acid, and
  - ii) a second single stranded replacement nucleic acid intermediate from a second double stranded nucleic acid substrate, wherein the second double stranded nucleic acid substrate is adapted at one or both of its 5' ends such that preferential degradation of one strand and/or strand separation generates the second single stranded replacement nucleic acid intermediate, wherein the second single stranded replacement nucleic acid intermediate comprises a 5' region that is complementary to a first sequence on the replacement sequence of the first single stranded nucleic acid intermediate, a 3' region that is complementary to a second sequence on the replacement sequence of the first single stranded nucleic acid intermediate and optionally a replacement region between the 5' and 3' regions that is not identical to sequence on the target nucleic acid,
- b) exposing the target nucleic acid to the first and second single stranded replacement nucleic acid intermediates under conditions suitable for recombination to occur between the first and second single stranded replacement nucleic acid intermediates and the target nucleic acid, and
- c) selecting a target nucleic acid whose sequence has been altered by inclusion of said first and second single stranded replacement nucleic acid intermediates.

18. The method of claim 1, wherein the single stranded replacement nucleic acid intermediate comprises a replacement region of at least 61 nucleotides in length.

19. The method of claim 1, wherein the single stranded replacement nucleic acid intermediate comprises a replacement region of at least 200 nucleotides in length.

20. The method of claim 1, wherein the single stranded replacement nucleic acid intermediate comprises a replacement region of at least 1500 nucleotides in length.

21. The method of claim 18, wherein the single stranded replacement nucleic acid intermediate comprises a replacement region comprises a whole gene.

22. The method of claim 21, wherein the gene acts as a selectable marker and the selection step involves selection of the gene.

23. The method of claim 1, wherein inclusion of the single stranded replacement nucleic acid intermediate in the target nucleic acid results in one or more mutations selected from the group consisting of substitutions, insertions, and deletions.

24. The method of claim 23, wherein the mutation is an insertion mutation.

25. The method of claim 1, wherein the 3' region on the single stranded replacement nucleic acid intermediate that is identical to sequence on the target nucleic acid is longer than the 5' region on the single stranded replacement nucleic acid intermediate that is identical to sequence on the target nucleic acid.

26. The method of claim 1, wherein the method is effected in a eukaryote.

27. The method of claim 1, wherein the selection step comprises antibiotic selection using antibiotic at a concentration between 5 to 70% above the lowest effective dose and incubating the host cell in which the single stranded replacement nucleic acid intermediate was exposed to the target nucleic acid at a temperature between 19° C. and 33° C. for a period of 1 to 7 days.

28. The method of claim 1, wherein the Red beta has a substitution mutation at E 176.

29. The method of claim 1, wherein the Red beta contains one or more mutations selected from the group consisting of E176A, E187A, A246V, Q252A, A255T, A255S, E256A and K258A.

30. The method of claim 1, wherein the Red beta further comprises one or more epitope tags.

* * * * *

SEQUENCE LISTING

<160> NUMBER OF SEQ ID NOS: 2

<210> SEQ ID NO 1
<211> LENGTH: 166
<212> TYPE: PRT
<213> ORGANISM: Lambda phage

```
<400> SEQUENCE: 1

Met Ser Thr Ala Ala Thr Ala Gly Lys Ala Arg Val Gly Met Asp Ser
1               5                   10                  15

Val Asp Thr Thr Arg Thr Ala Lys Gly Asp Ala Ser Asp Ala Ala Val
            20                  25                  30

Ala Asn Tyr Gly Asn Trp Thr Lys Tyr Ala Asp Lys Asn Gly Val Val
        35                  40                  45

Val Gly Val Asp Gly Trp Ser Arg Asn Asn Asp Gly Met Asp Asp Asn
    50                  55                  60

Ser Cys Thr Cys Arg Tyr Arg Lys Asp Arg Asn His Cys Val Thr Trp
65                  70                  75                  80

Met Asp Cys Arg Arg Lys Thr Arg Gly Arg Thr Gly Trp Ser His Lys
                85                  90                  95

Arg Met Arg His Lys Ala Met Cys Ala Arg Ala Gly Ala Gly Tyr Asp
            100                 105                 110

Lys Asp Ala Arg Val Asn Thr Ala Tyr Thr Ala Arg Arg Asp Thr Val
        115                 120                 125

Asn Asp Thr Met Asn Thr Ala Asp Lys Thr Trp Asp Asp Cys Ser
130                 135                 140

Arg Arg Asp Arg Ala Ser Ser Thr Ala Val Lys Ala Gly Lys Lys
145                 150                 155                 160

Ala Ala Lys Val Ala Ala
                165

<210> SEQ ID NO 2
<211> LENGTH: 261
<212> TYPE: PRT
<213> ORGANISM: Lambda phage

<400> SEQUENCE: 2

Met Ser Thr Ala Leu Ala Thr Leu Ala Gly Lys Leu Ala Glu Arg Val
1               5                   10                  15

Gly Met Asp Ser Val Asp Pro Gln Glu Leu Ile Thr Thr Leu Arg Gln
            20                  25                  30

Thr Ala Phe Lys Gly Asp Ala Ser Asp Ala Gln Phe Ile Ala Leu Leu
        35                  40                  45

Ile Val Ala Asn Gln Tyr Gly Leu Asn Pro Trp Thr Lys Glu Ile Tyr
    50                  55                  60

Ala Phe Pro Asp Lys Gln Asn Gly Ile Val Pro Val Val Gly Val Asp
65                  70                  75                  80

Gly Trp Ser Arg Ile Ile Asn Glu Asn Gln Gln Phe Asp Gly Met Asp
                85                  90                  95

Phe Glu Gln Asp Asn Glu Ser Cys Thr Cys Arg Ile Tyr Arg Lys Asp
            100                 105                 110

Arg Asn His Pro Ile Cys Val Thr Glu Trp Met Asp Glu Cys Arg Arg
        115                 120                 125

Glu Pro Phe Lys Thr Arg Glu Gly Arg Glu Ile Thr Gly Pro Trp Gln
    130                 135                 140

Ser His Pro Lys Arg Met Leu Arg His Lys Ala Met Ile Gln Cys Ala
145                 150                 155                 160

Arg Leu Ala Phe Gly Phe Ala Gly Ile Tyr Asp Lys Asp Glu Ala Glu
                165                 170                 175

Arg Ile Val Glu Asn Thr Ala Tyr Thr Ala Glu Arg Gln Pro Glu Arg
            180                 185                 190

Asp Ile Thr Pro Val Asn Asp Glu Thr Met Gln Glu Ile Asn Thr Leu
```

-continued

```
                195                 200                 205
Leu Ile Ala Leu Asp Lys Thr Trp Asp Asp Leu Leu Pro Leu Cys
        210                 215                 220

Ser Gln Ile Phe Arg Arg Asp Ile Arg Ala Ser Ser Glu Leu Thr Gln
225                 230                 235                 240

Ala Glu Ala Val Lys Ala Leu Gly Phe Leu Lys Gln Lys Ala Ala Glu
                245                 250                 255

Gln Lys Val Ala Ala
            260
```